US012624077B2

(12) United States Patent
Yamamoto et al.

(10) Patent No.: US 12,624,077 B2
(45) Date of Patent: May 12, 2026

(54) CXCR3 LIGAND

(71) Applicant: Chugai Seiyaku Kabushiki Kaisha, Tokyo (JP)

(72) Inventors: Yohei Yamamoto, Shizuoka (JP); Mika Sakurai, Shizuoka (JP); Kenta Haraya, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 1243 days.

(21) Appl. No.: 17/299,629

(22) PCT Filed: Dec. 4, 2019

(86) PCT No.: PCT/JP2019/047382
§ 371 (c)(1),
(2) Date: Jun. 3, 2021

(87) PCT Pub. No.: WO2020/116498
PCT Pub. Date: Jun. 11, 2020

(65) Prior Publication Data
US 2022/0017585 A1 Jan. 20, 2022

(30) Foreign Application Priority Data
Dec. 4, 2018 (JP) ................................. 2018-227353

(51) Int. Cl.
| | |
|---|---|
| *A61P 29/00* | (2006.01) |
| *A61P 37/02* | (2006.01) |
| *A61P 43/00* | (2006.01) |
| *C07K 1/113* | (2006.01) |
| *C07K 14/52* | (2006.01) |
| *C07K 19/00* | (2006.01) |
| *C12P 21/00* | (2006.01) |
| *A61K 38/00* | (2006.01) |

(52) U.S. Cl.
CPC ............ *C07K 14/521* (2013.01); *C07K 1/113* (2013.01); *A61K 38/00* (2013.01); *C07K 2319/30* (2013.01)

(58) Field of Classification Search
CPC .. C07K 14/521; C07K 1/113; C07K 2319/30; A61K 38/00
See application file for complete search history.

(56) References Cited

U.S. PATENT DOCUMENTS

| | | | |
|---|---|---|---|
| 6,534,626 B1 | 3/2003 | Oravecz et al. | |
| 6,562,347 B1 | 5/2003 | Kwak et al. | |
| 2004/0197303 A1* | 10/2004 | Merzouk .................. | A61P 9/00 424/85.1 |
| 2005/0119174 A1 | 6/2005 | Sugaru et al. | |
| 2008/0095758 A1 | 4/2008 | Lee et al. | |
| 2020/0207846 A1* | 7/2020 | Igawa .................. | C07K 16/24 |
| 2025/0073307 A1 | 3/2025 | Yamamoto et al. | |

FOREIGN PATENT DOCUMENTS

| | | |
|---|---|---|
| JP | 2007525188 A | 9/2007 |
| JP | 2008545396 A | 12/2008 |
| WO | WO 03082335 A1 | 10/2003 |
| WO | WO 2005016241 A2 | 2/2005 |
| WO | WO2006125077 A2 | 11/2006 |
| WO | WO 2012172336 A2 | 12/2012 |
| WO | WO 2015112505 A1 | 7/2015 |
| WO | WO 2018097308 A1 | 5/2018 |
| WO | WO2020116498 A1 | 6/2020 |
| WO | WO2021038033 A1 | 3/2021 |
| WO | WO2023120643 A1 | 6/2023 |

OTHER PUBLICATIONS

UniProt Accession No. P02778, human CXCL10 protein, accessed Nov. 13, 2024 at URL rest.uniprot.org/uniprotkb/P02778.txt, pp. 1-7 (Year: 2024).*
Drumm et al, Genetic Variation and Clinical Heterogeneity in Cystic Fibrosis, Annu. Rev. Pathol. Mech. Dis., 2012, 7, pp. 267-282 (Year: 2012).*
Yampolsky et al., The Exchangeability of Amino Acids in Proteins, Genetics, 2005, 170, pp. 1459-1472. (Year: 2005).*
Booth, V., et al., "The CXCR3 binding chemokine IP-10/CXCL10: structure and receptor interactions," Biochem., 41(33):10418-10425 (2002).
Cole, K. E., et al., "Interferon-inducible T cell alpha chemoattractant (I-TAC): a novel non-ELR CXC chemokine with potent activity on activated T cells through selective high affinity binding to CXCR3," J Exp Med., 187(12):2009-2021 (1998).
Decalf, J., et al., "Inhibition of DPP4 activity in humans establishes its in vivo role in CXCL10 post-translational modification: prospective placebo-controlled clinical studies," EMBO Mol Med., 8(6):679-683 (2016).
Proost, P., et al., "Amino-terminal truncation of $CXCR_3$ agonists impairs receptor signaling and lymphocyte chemotaxis, while preserving antiangiogenic properties," Blood, 98(13):3554-3561 (2001).
Rainczuk, A., et al., "Evidence for the antagonistic form of CXC-motif chemokine CXCL10 in serous epithelial ovarian tumours," Int J Cancer, 134(3):530-541 (2014).
Swaminathan, G. J., et al., "Crystal structures of oligomeric forms of the IP-10/CXCL10 chemokine," Structure, 11(5):521-532 (2003).
Tensen, C. P., et al., "Human IP-9: A keratinocyte-derived high affinity CXC-chemokine ligand for the IP-10/Mig receptor (CXCR3)," J Invest Dermatol., 112(5):716-722 (1999).

(Continued)

*Primary Examiner* — Julie Ha
*Assistant Examiner* — Kristina M Hellman
(74) *Attorney, Agent, or Firm* — Nixon & Vanderhye P.C.

(57) ABSTRACT

The present disclosure relates to CXCR3 ligands having resistance to DPPIV and having CXCR3-expressing cell migration-inducing activity. The present disclosure specifically relates to N-terminal amino acid modifications and N-terminal amino acid sequences important for resistance to DPPIV and CXCR3-expressing cell migration-inducing activity.

10 Claims, 12 Drawing Sheets

Specification includes a Sequence Listing.

(56) References Cited

OTHER PUBLICATIONS

Trotta, T., et al., "Modelling of the membrane receptor CXCR3 and its complexes with CXCL9, CXCL10 and CXCL11 chemokines: putative target for new drug design," Mol Immunol., 47(2-3):332-339 (2009).

Wang, P., et al., "Integrating individual functional moieties of CXCL10 and CXCL11 into a novel chimeric chemokine leads to synergistic antitumor effects: a strategy for chemokine-based multi-target-directed cancer therapy," Cancer Immunol Immunother., 59(11):1715-1726 (2010).

U.S. Appl. No. 09/646,028, 371(c) date Sep. 12, 2000, Kwak et al.

U.S. Appl. No. 09/555,663, 371(c) date Sep. 14, 2000, Oravecz et al.

U.S. Appl. No. 10/510,121, 371(c) date Nov. 3, 2004, Sugaru et al.

Aguilera-Durán, G. and Romo-Mancillas, A., "Computational Study of C-X-C Chemokine Receptor (CXCR)3 Binding with Its Natural Agonists Chemokine (C-X-C Motif) Ligand (CXCL)9, 10 and 11 and with Synthetic Antagonists: Insights of Receptor Activation towards Drug Design for Vitiligo," Molecules, 25:4413 (2020).

Campanella, G. S. V., et al., "CXCR3 and Heparin Binding Sites of the Chemokine IP-10 (CXCL10)," J Biol Chem., 278(19):17066-17074 (2003).

Gerlza, T., et al., "Designing an improved T-cell mobilizing CXCL10 mutant through enhanced GAG binding affinity," Protein Eng Des Sel., 32(8):367-373 (2020).

Graham, G. J., et al., "Leukocyte Adhesion: Reconceptualizing Chemokine Presentation by Glycosaminoglycans," Trends Immunol., 40(6):472-481 (2019).

Tokunaga, R., et al., "CXCL9, CXCL10, CXCL11/CXCR3 axis for immune activation—a target for novel cancer therapy," Cancer Treat Rev., 63:40-47 (2018).

U.S. Appl. No. 18/722,266, filed Jun. 20, 2024, Yamamoto et al., related application.

Jazayeri, J. A. and Carroll, G. J., "Fc-based cytokines: prospects for engineering superior therapeutics," BioDrugs, 22(1):11-26 (2008).

Metzemaekers, M., et al., "Regulation of Chemokine Activity—A Focus on the Role of Dipeptidyl Peptidase IV/CD26," Front Immunol., 7:483 (2016).

* cited by examiner

FIG. 3B

N-terminal DPPIV
recognition site hCXCL11
or
hITIP hIgG1 Fc

DPPIV recognition site, cleavage after Pro

Signal sequence

CXCL11/hITIP sequence

-9  -8  -7  -6  -5  -4  -3  -2  -1  1  2  3  4  5  6  7  8  9

···V  A  T  A  T  G  V  H  S/F  P  M  F  K  R  G  R  C···

(SEQ ID NO:217)

Modification sites { Substitution a

Insertion: b  c

CXCR3 LIGAND

CROSS-REFERENCE TO RELATED APPLICATIONS

This application is a U.S. National Phase of PCT Application No. PCT/JP2019/047382, filed Dec. 4, 2019, which claims the benefit of Japanese Patent Application No. 2018-227353, filed Dec. 4, 2018, each of which is incorporated herein by reference in its entirety.

REFERENCE TO SEQUENCE LISTING SUBMITTED ELECTRONICALLY

The content of the electronically submitted sequence listing (Name: 6663_0175 Substitute_Sequence_Listing.txt; Size: 178 kilobytes; and Date of Creation: May 24, 2024) filed with the application is incorporated herein by reference in its entirety.

TECHNICAL FIELD

The present disclosure relates to CXCR3 ligands, methods of producing CXCR3 ligands, use of CXCR3 ligands, and methods of conferring resistance to DPPIV on CXCR3 ligands.

BACKGROUND ART

Chemokine receptor CXCR3 (also called G Protein-coupled Receptor 9 (GPR9) and CD183) belongs to the CXC chemokine receptor family and is a G protein-coupled receptor that binds to chemokines CXCL9, CXCL10, and CXCL11. CXCR3 is expressed primarily in activated T-helper type 1 (Th1) lymphocytes and cytoxic T cells, but is also present in natural killer cells, macrophages, dendritic cells, and B lymphocyte subsets. The chemokines CXCL9, CXCL10, and CXCL11 are three naturally-occurring CXCR3 ligands. The interaction of CXCR3 and its ligands is involved in guiding receptor-bearing cells to specific parts of the body, especially sites of inflammation, immune impairment, and immune dysfunction.

CXCL10 (C-X-C motif chemokine 10) is also called "IP10 (interferon gamma-induced protein 10)" or "small inducible cytokine B10" and is a chemokine belonging to the CXC subfamily.

C-X-C motif chemokine 10 (CXCL10) is known to promote T cell migration activity via CXCR3 (NPL 1). Furthermore, it has been reported that direct administration of CXCL10 into a mouse tumor increases T cells in the tumor (NPL 2).

On the other hand, it is known that the two amino acids from N-terminal of CXCL10 are cleaved by Dipeptidyl Peptidase-4 (DPPIV, DPP4) (NPL 1). Cleaved CXCL10 is present even in human blood and is also reported to be present in human tumors, indicating that CXCL10 is cleaved by DPPIV in human blood and tumors (NPLs 3 and 4). Furthermore, since it has been reported that the migration-inducing activity of DPPIV-cleaved CXCL10 is significantly reduced, it is thought that the cleavage could be one of the CXCL10-inactivating mechanisms (NPL 1). The three-dimensional structure of CXCL10 has been elucidated (NPLs 5 and 6), and a predicted structure of a model of a complex with CXCR3 has also been reported (NPL 7). In this complex model, the N-terminus of CXCL10 is arranged in such a way that it penetrates into the inside of CXCR3, and this interaction is thought to be important for CXCR3 activation.

C-X-C motif chemokine 11 (C-X-C motif chemokine ligand 11, CXCL11) is a C-X-C chemokine which is also called I-TAC (Interferon-inducible T-cell alpha chemoattractant) or IP-9 (Interferon-gamma-inducible protein 9), and naturally-occurring CXCL11 is said to bind to CXCR3 more strongly than naturally-occurring CXCL10 and naturally-occurring CXCL9 (NPLs 8 and 9). It is known that the N-terminal sequence of naturally-occurring human CXCL11 is also cleaved by DPPIV (NPL 1).

C-X-C motif chemokine 9 (C-X-C motif chemokine ligand 9, CXCL9) is a C-X-C chemokine which is also called Monokine induced by gamma-interferon (MIG), and the N-terminal sequence of naturally-occurring human CXCL9 is also known to be cleaved by DPPIV (NPL 1).

CITATION LIST

Non-Patent Literature

[NPL 1] Proost P, Blood. 2001 Dec. 15; 98(13):3554-61.
[NPL 2] Wang P, Cancer Immunol Immunother. 2010 November; 59(11):1715-26.
[NPL 3] Decalf J, EMBO Mol Med. 2016 Jun. 1; 8(6):679-83.
[NPL 4] Rainczuk A, Int J Cancer. 2014 Feb. 1; 134(3):530-41.
[NPL 5] Booth V, Biochemistry. 2002 Aug. 20; 41(33):10418-25.
[NPL 6] Swaminathan G J, Structure. 2003 May; 11(5):521-32.
[NPL 7] Trotta T, Mol Immunol. 2009 December;47(2-3):332-9.
[NPL 8] Cole K E, The Journal of Experimental Medicine. 187 (12): 2009-21.
[NPL 9] Tensen CP, The Journal of Investigative Dermatology. 112 (5): 716-22.

SUMMARY OF INVENTION

Technical Problem

The present disclosure provides CXCR3 ligands having resistance to DPPIV and having CXCR3-expressing cell migration-inducing activity, methods of using these CXCR3 ligands, and methods of producing these CXCR3 ligands. The present disclosure also provides methods of conferring DDPIV resistance on CXCR3 ligands.

Solution to Problem

The present inventors discovered CXCR3 ligands having resistance to DPPIV and CXCR3-expressing-cell migration-inducing activity, and completed the present disclosure. Specifically, the inventors discovered N-terminal amino acid modifications and N-terminal amino acid sequences that are important for resistance to DPPIV and CXCR3-expressing-cell migration-inducing activity.

The present disclosure specifically includes the embodiments exemplified below:

[A-1] a CXCR3 ligand having resistance to DPPIV and having an activity to cause migration of cells expressing CXCR3;

[A-2] the CXCR3 ligand according to [A-1], wherein the CXCR3 ligand has a C-X-C motif;

[A-3] the CXCR3 ligand according to [A-2], wherein the two cysteines comprised in the C-X-C motif each form a disulfide bond with a cysteine other than that in the C-X-C motif comprised in the CXCR3 ligand;

[A-4] the CXCR3 ligand according to any one of [A-1] to [A-3], wherein the CXCR3 ligand has any of the following sequences (a1) to (a7) at the N-terminus:
(a1) V-X1-L (X1 is F, G, I, K, L, M, T, V, W, or Y);
(a2) X2-V-P (X2 is A, F, G, H, I, K, L, M, N, P, Q, R, S, T, V, W, or Y);
(a3) V-X3-P (X3 is A, F, G, H, I, K, L, M, P, Q, R, S, T, V, W, or Y);
(a4) P-L-S;
(a5) X4-F-P (X4 is A, D, E, F, G, H, I, K, L, M, N, P, Q, S, T, V, W, or Y);
(a6) F-X5-M (X5 is A, D, E, G, H, I, M, N, Q, R, S, T, V, W, or Y); and
(a7) F-X6-P (X6 is A, D, E, F, G, H, L, M, N, P, Q, S, T, W, or Y);

[A-5] the CXCR3 ligand according to any one of [A-1] to [A-4], wherein the CXCR3 ligand has any of the following sequences (b1) to (b7) at the N-terminus:
(b1) V-X1-L-S-R-T-V-R (X1 is F, G, I, K, L, M, T, V, W, or Y) (SEQ ID NO: 205);
(b2) X2-V-P-L-S-R-T-V-R (X2 is A, F, G, H, I, K, L, M, N, P, Q, R, S, T, V, W, or Y) (SEQ ID NO: 206);
(b3) V-X3-P-L-S-R-T-V-R (X3 is A, F, G, H, I, K, L, M, P, Q, R, S, T, V, W, or Y) (SEQ ID NO: 207);
(b4) P-L-S-R-T-V-R (SEQ ID NO: 208);
(b5) X4-F-P-M-F-K-R-G-R (X4 is A, D, E, F, G, H, I, K, L, M, N, P, Q, S, T, V, W, or Y) (SEQ ID NO: 209);
(b6) F-X5-M-F-K-R-G-R (X5 is A, D, E, G, H, I, M, N, Q, R, S, T, V, W, or Y) (SEQ ID NO: 210); and
(b7) F-X6-P-M-F-K-R-G-R (X6 is A, D, E, F, G, H, L, M, N, P, Q, S, T, W, or Y) (SEQ ID NO: 211);

[A-6] the CXCR3 ligand according to any one of [A-1] to [A-3], wherein the CXCR3 ligand has any of the following sequences (a1) to (a5) at the N-terminus:
(a1) V-X1-L (X1 is F, G, I, L, M, T, V, W, or Y);
(a2) X2-V-P (X2 is A, G, I, L, N, Q, S, T, or W);
(a3) V-X3-P (X3 is A, F, G, I, M, P, T, or V);
(a4) P-L-S; and
(a5) X4-F-P (X4 is A, D, E, G, M, N, Q, S, T, V, or Y);

[A-7] the CXCR3 ligand according to any of [A-1] to [A-3] or [A-6], wherein the CXCR3 ligand has any of the following sequences (b1) to (b5) at the N-terminus:
(b1) V-X1-L-S-R-T-V-R (X1 is F, G, I, L, M, T, V, W, or Y) (SEQ ID NO: 212); (b2) X2-V-P-L-S-R-T-V-R (X2 is A, G, I, L, N, Q, S, T, or W) (SEQ ID NO: 213); (b3) V-X3-P-L-S-R-T-V-R (X3 is A, F, G, I, M, P, T, or V) (SEQ ID NO: 214); (b4) P-L-S-R-T-V-R (SEQ ID NO: 208); and (b5) X4-F-P-M-F-K-R-G-R (X4 is A, D, E, G, M, N, Q, S, T, V, or Y) (SEQ ID NO: 215);

[A-8] the CXCR3 ligand according to any one of [A-2] to [A-7], wherein the C-X-C motif is C-T-C(Cys-Thr-Cys), C-L-C(Cys-Leu-Cys), or C-S-C(Cys-Ser-Cys);

[A-9] the CXCR3 ligand according to any one of [A-2] to [A-8], wherein the CXCR3 ligand further has any of the following (c1) to (c5) at the C-terminus of the C-X-C motif:
(c1) the sequence from the 12th amino acid to the 77th amino acid of SEQ ID NO: 60;
(c2) the sequence from the 12th amino acid to the 73rd amino acid of SEQ ID NO: 61;
(c3) the sequence from the 12th amino acid to the 103rd amino acid of SEQ ID NO: 62;

(c4) the sequence from the 12th amino acid to the 77th amino acid of SEQ ID NO: 1; and
(c5) the sequence from the $12^{th}$ amino acid to the $77^{th}$ amino acid of SEQ ID NO: 63;

[A-10] the CXCR3 ligand according to any one of [A-1] to [A-9], wherein the sequence of the CXCR3 ligand is any of the following (d1) to (d7):
(d1) a sequence shown by any one of SEQ ID NOs: 2 to 57, 92 to 147, and 149 to 204;
(d2) a sequence showing 90% or more sequence identity to SEQ ID NO: 60;
(d3) a sequence showing 90% or more sequence identity to SEQ ID NO: 61;
(d4) a sequence showing 90% or more sequence identity to SEQ ID NO: 62;
(d5) a sequence showing 90% or more sequence identity to SEQ ID NO: 63;
(d6) a sequence showing 90% or more sequence identity to SEQ ID NO: 1; and
(d7) a sequence comprising 10 or less amino acid substitutions, insertions, or deletions to a sequence selected from SEQ ID NOs: 1 to 57, 60 to 63, 92 to 147, and 149 to 204;

[A-11] the CXCR3 ligand according to any one of [A-1] to [A-10], wherein resistance to DPPIV indicates that, after treatment at 37° C. for 1 hour in the presence of 0.2 mg/ml of the CXCR3 ligand or CXCR3 ligand-human Fc fusion protein and 200 nM human DPPIV, the two N-terminal residues of the CXCR3 ligand are not lost;

[A-12] the CXCR3 ligand according to any one of [A-1] to [A-11], wherein the activity of the CXCR3 ligand to cause migration of cells expressing CXCR3 is 30% or more of the activity of a naturally-occurring human CXCL10 to cause migration of cells expressing CXCR3, or 25% or more of the activity of a naturally-occurring human CXCL11 to cause migration of cells expressing CXCR3;

[A-13] the CXCR3 ligand according to any one of [A-1] to [A-12], wherein the CXCR3 ligand concentration when the activity of the CXCR3 ligand to cause migration of cells expressing CXCR3 is at maximum is lower than the concentration of a naturally-occurring human CXCL10 and/or naturally-occurring human CXCL11 when the activity of the naturally-occurring human CXCL10 and/or the naturally-occurring human CXCL11 to cause migration of cells expressing CXCR3 is at maximum; and

[A-14] the CXCR3 ligand according to any one of [A-1] to [A-13], wherein the cells expressing CXCR3 are cells isolated from a transfectant or a living body expressing CXCR3.

The present disclosure also includes the embodiments exemplified below:
[B-1] a CXCR3 ligand having any of the following sequences (a1) to (a7) at the N-terminus:
(a1) V-X1-L (X1 is F, G, I, K, L, M, T, V, W, or Y);
(a2) X2-V-P (X2 is A, F, G, H, I, K, L, M, N, P, Q, R, S, T, V, W, or Y);
(a3) V-X3-P (X3 is A, F, G, H, I, K, L, M, P, Q, R, S, T, V, W, or Y);
(a4) P-L-S;
(a5) X4-F-P (X4 is A, D, E, F, G, H, I, K, L, M, N, P, Q, S, T, V, W, or Y);
(a6) F-X5-M (X5 is A, D, E, G, H, I, M, N, Q, R, S, T, V, W, or Y); and

5

(a7) F-X6-P (X6 is A, D, E, F, G, H, L, M, N, P, Q, S, T, W, or Y);

[B-2] the CXCR3 ligand according to [B-1], which has any of the following sequences (b1) to (b7) at the N-terminus:

(b1) V-X1-L-S-R-T-V-R (X1 is F, G, I, K, L, M, T, V, W, or Y) (SEQ ID NO: 205);

(b2) X2-V-P-L-S-R-T-V-R (X2 is A, F, G, H, I, K, L, M, N, P, Q, R, S, T, V, W, or Y) (SEQ ID NO: 206);

(b3) V-X3-P-L-S-R-T-V-R (X3 is A, F, G, H, I, K, L, M, P, Q, R, S, T, V, W, or Y) (SEQ ID NO: 207);

(b4) P-L-S-R-T-V-R (SEQ ID NO: 208);

(b5) X4-F-P-M-F-K-R-G-R (X4 is A, D, E, F, G, H, I, K, L, M, N, P, Q, S, T, V, W, or Y) (SEQ ID NO: 209);

(b6) F-X5-M-F-K-R-G-R (X5 is A, D, E, G, H, I, M, N, Q, R, S, T, V, W, or Y) (SEQ ID NO: 210); and (b7) F-X6-P-M-F-K-R-G-R (X6 is A, D, E, F, G, H, L, M, N, P, Q, S, T, W, or Y) (SEQ ID NO: 211);

[B-3] the CXCR3 ligand according to [B-1] or [B-2], which has a C-X-C motif on the C-terminal side of the sequences (a1) to (a7);

[B-4] the CXCR3 ligand according to [B-2], which has a C-X-C motif at the C-terminus of the sequences (b1) to (b7);

[B-5] a CXCR3 ligand having any of the following sequences (a1) to (a5) at the N-terminus:

(a1) V-X1-L (X1 is F, G, I, L, M, T, V, W, or Y);

(a2) X2-V-P (X2 is A, G, I, L, N, Q, S, T, or W);

(a3) V-X3-P (X3 is A, F, G, I, M, P, T, or V);

(a4) P-L-S; and (a5) X4-F-P (X4 is A, D, E, G, M, N, Q, S, T, V, or Y);

[B-6] the CXCR3 ligand according to [B-5], which has any of the following sequences (b1) to (b5) at the N-terminus:

(b1) V-X1-L-S-R-T-V-R (X1 is F, G, I, L, M, T, V, W, or Y) (SEQ ID NO: 212);

(b2) X2-V-P-L-S-R-T-V-R (X2 is A, G, I, L, N, Q, S, T, or W) (SEQ ID NO: 213);

(b3) V-X3-P-L-S-R-T-V-R (X3 is A, F, G, I, M, P, T, or V) (SEQ ID NO: 214);

(b4) P-L-S-R-T-V-R (SEQ ID NO: 208); and (b5) X4-F-P-M-F-K-R-G-R (X4 is A, D, E, G, M, N, Q, S, T, V, or Y) (SEQ ID NO: 215);

[B-7] the CXCR3 ligand according to [B-5] or [B-6], which has a C-X-C motif on the C-terminal side of the sequences (a1) to (a5);

[B-8] the CXCR3 ligand according to [B-6], which has a C-X-C motif at the C-terminus of the sequences (b1) to (b5);

[B-9] the CXCR3 ligand according to any one of [B-3], [B-4], [B-7], and [B-8], wherein the C-X-C motif is C-T-C(Cys-Thr-Cys), C-L-C(Cys-Leu-Cys), or C-S-C (Cys-Ser-Cys);

[B-10] the CXCR3 ligand according to any one of [B-3], [B-4], [B-7], [B-8], and [B-9], wherein the CXCR3 ligand further has any of the following (c1) to (c5) at the C-terminus of the C-X-C motif:

(c1) the sequence from the 12th amino acid to the 77th amino acid of SEQ ID NO: 60;

(c2) the sequence from the 12th amino acid to the 73rd amino acid of SEQ ID NO: 61;

(c3) the sequence from the 12th amino acid to the 103rd amino acid of SEQ ID NO: 62;

(c4) the sequence from the 12th amino acid to the 77th amino acid of SEQ ID NO: 1; and

(c5) the sequence from the $12^{th}$ amino acid to the $77^{th}$ amino acid of SEQ ID NO: 63; and

[B-11] the CXCR3 ligand according to any one of [B-1] to [B-10], wherein the sequence of the CXCR3 ligand is any of the following (d1) to (d7): (d1) a sequence shown by any one of SEQ ID NOs: 2 to 57, 92 to 147, and 149 to 204;

(d2) a sequence showing 90% or more sequence identity to SEQ ID NO: 60;

(d3) a sequence showing 90% or more sequence identity to SEQ ID NO: 61;

(d4) a sequence showing 90% or more sequence identity to SEQ ID NO: 62;

(d5) a sequence showing 90% or more sequence identity to SEQ ID NO: 63;

(d6) a sequence showing 90% or more sequence identity to SEQ ID NO: 1; and (d7) a sequence comprising 10 or less amino acid substitutions, insertions, or deletions to a sequence selected from SEQ ID NOs: 1 to 57, 60 to 63, 92 to 147, and 149 to 204.

The present disclosure also encompasses the embodiments exemplified below:

[C-1] an isolated nucleic acid encoding the CXCR3 ligand according to any one of [A-1] to [B-11];

[C-2] a host cell comprising the nucleic acid according to [C-1];

[C-3] a method of producing the CXCR3 ligand according to any one of [A-1] to [B-11], wherein the method comprises culturing the host cell according to [C-2] such that the CXCR3 ligand is produced;

[C-4] the method according to [C-3], further comprising recovering the CXCR3 ligand from the host cell;

[C-5] a fusion protein comprising the CXCR3 ligand according to any one of [A-1] to [B-11];

[C-6] the fusion protein according to [C-5], wherein the CXCR3 ligand according to any one of [A-1] to [B-11] and an antibody Fc region are fused;

[C-7] the fusion protein according to [C-5], wherein the CXCR3 ligand according to any one of [A-1] to [B-11] and an intact antibody or an antibody fragment are fused;

[C-8] the fusion protein according to [C-6] or [C-7], wherein the CXCR3 ligand and the antibody Fc region, or the CXCR3 ligand and the intact antibody or antibody fragment are fused via a linker; and

[C-9] a pharmaceutical composition comprising the CXCR3 ligand according to any one of [A-1] to [B-11] or the fusion protein according to any one of [C-5] to [C-8].

The present disclosure also encompasses the embodiments exemplified below:

[D-1] a method of conferring resistance to DPPIV on a parent CXCR3 ligand in which the $2^{nd}$ amino acid from the N-terminus is P or A, wherein the method comprises any of the following:

(1) substituting the $2^{nd}$ amino acid from the N-terminus of the parent CXCR3 ligand from P or A to F, G, I, K, L, M, T, V, W, or Y;

(2) further adding A, F, G, H, I, K, L, M, N, P, Q, R, S, T, V, W, or Y to the N-terminus of the parent CXCR3 ligand;

(3) inserting A, F, G, H, I, K, L, M, P, Q, R, S, T, V, W, or Y between the $1^{st}$ and $2^{nd}$ amino acids at the N-terminus of the parent CXCR3 ligand; and (4) deleting V at the N-terminus of the parent CXCR3 ligand;

[D-2] a method of conferring resistance to DPPIV on a parent CXCR3 ligand in which the $2^{nd}$ amino acid from the N-terminus is P or A, wherein the method comprises any of the following:

(1) substituting the $2^{nd}$ amino acid from the N-terminus of the parent CXCR3 ligand from P or A to F, G, I, L, M, T, V, W, or Y;

(2) further adding A, G, I, L, N, Q, S, T, or W to the N-terminus of the parent CXCR3 ligand;

(3) inserting A, F, G, I, M, P, T, or V between the $1^{st}$ and $2^{nd}$ second amino acids at the N-terminus of the parent CXCR3 ligand; and (4) deleting V at the N-terminus of the parent CXCR3 ligand;

[D-3] the method according to [D-1] or [D-2], wherein the parent CXCR3 ligand further has a C-X-C motif;

[D-4] the method according to [D-3], wherein the C-X-C motif is C-T-C(Cys-Thr-Cys), C-L-C(Cys-Leu-Cys), or C-S-C(Cys-Ser-Cys);

[D-5] the method according to any one of [D-1] to [D-4], wherein the parent CXCR3 ligand is either a naturally-occurring human CXCL10 or a variant thereof, a naturally-occurring human CXCL11 or a variant thereof, or a naturally-occurring human CXCL9 or a variant thereof;

[D-6] the method according to [D-1] to [D-5], wherein the $1^{st}$ amino acid at the N-terminus of the parent CXCR3 ligand is V;

[D-7] the method according to any one of [D-1] to [D-6], wherein the N-terminal sequence of the parent CXCR3 ligand is V-P-L-S-R-T-V-R (SEQ ID NO: 86) or V-A-L-S-R-T-V-R (SEQ ID NO: 87); and

[D-8] the method according to [D-7], wherein the C-X-C motif is located at the C-terminus of the N-terminal sequence "V-P-L-S-R-T-V-R (SEQ ID NO: 86)" or "V-A-L-S-R-T-V-R (SEQ ID NO: 87)".

The present disclosure also encompasses the embodiments exemplified below:

[E-1] a method of producing a CXCR3 ligand having resistance to DPPIV, wherein the method carries out any of the following modifications to a parent CXCR3 ligand in which the $2^{nd}$ amino acid from the N-terminus is P or A:

(1) substituting the $2^{nd}$ amino acid from the N-terminus of the parent CXCR3 ligand from P or A to F, G, I, K, L, M, T, V, W, or Y;

(2) further adding A, F, G, H, I, K, L, M, N, P, Q, R, S, T, V, W, or Y to the N-terminus of the parent CXCR3 ligand;

(3) inserting A, F, G, H, I, K, L, M, P, Q, R, S, T, V, W, or Y between the $1^{st}$ and $2^{nd}$ amino acids at the N-terminus of the parent CXCR3 ligand; and (4) deleting the V at the N-terminus of the parent CXCR3 ligand;

[E-2] a method of producing a CXCR3 ligand having resistance to DPPIV, wherein the method carries out any of the following modifications to a parent CXCR3 ligand in which the $2^{nd}$ amino acid from the N-terminus is P or A:

(1) substituting the $2^{nd}$ amino acid from the N-terminus of the parent CXCR3 ligand from P or A to F, G, I, L, M, T, V, W, or Y;

(2) further adding A, G, I, L, N, Q, S, T, or W to the N-terminus of the parent CXCR3 ligand;

(3) inserting A, F, G, I, M, P, T, or V between the $1^{st}$ and $2^{nd}$ second amino acids at the N-terminus of the parent CXCR3 ligand; and (4) deleting V at the N-terminus of the parent CXCR3 ligand;

[E-3] the method according to [E-1] or [E-2], wherein the parent CXCR3 ligand further has a C-X-C motif;

[E-4] the method according to [E-3], wherein the C-X-C motif is C-T-C(Cys-Thr-Cys), C-L-C(Cys-Leu-Cys), or C-S-C(Cys-Ser-Cys);

[E-5] the method according to any one of [E-1] to [E-4], wherein the parent CXCR3 ligand is either a naturally-occurring human CXCL10 or a variant thereof, a naturally-occurring human CXCL11 or a variant thereof, or a naturally-occurring human CXCL9 or a variant thereof;

[E-6] the method according to [E-1] to [E-5], wherein the $1^{st}$ amino acid at the N-terminus of the parent CXCR3 ligand is V;

[E-7] the method according to any one of [E-1] to [E-6], wherein the N-terminal sequence of the parent CXCR3 ligand is V-P-L-S-R-T-V-R (SEQ ID NO: 86) or V-A-L-S-R-T-V-R (SEQ ID NO: 87);

[E-8] the method according to [E-7], wherein the parent C-X-C motif is located at the C-terminus of the N-terminal sequence "V-P-L-S-R-T-V-R (SEQ ID NO: 86)" or "V-A-L-S-R-T-V-R (SEQ ID NO: 87)"; and

[E-9] a CXCR3 ligand produced by a method of any one of [E-1] to [E-8].

The present disclosure also encompasses the embodiments exemplified below:

[F-1] a method of conferring resistance to DPPIV on a parent CXCR3 ligand in which the $2^{nd}$ amino acid from the N-terminus is P, wherein the method comprises any of the following:

(1) further adding A, D, E, F, G, H, I, K, L, M, N, P, Q, S, T, V, W, or Y to the N-terminus of the parent CXCR3 ligand;

(2) substituting the $2^{nd}$ amino acid from the N-terminus of the parent CXCR3 ligand from P to A, D, E, G, H, I, M, N, Q, R, S, T, V, W, or Y; and (3) inserting A, D, E, F, G, H, L, M, N, P, Q, S, T, W, or Y between the $1^{st}$ and $2^{nd}$ amino acids at the N-terminus of the parent CXCR3 ligand;

[F-2] a method of conferring resistance to DPPIV on a parent CXCR3 ligand in which the $2^{nd}$ amino acid from the N-terminus is P, wherein the method comprises further adding A, D, E, G, M, N, Q, S, T, V, or Y to the N-terminus of the parent CXCR3 ligand;

[F-3] the method according to [F-1] or [F-2], wherein the parent CXCR3 ligand further has a C-X-C motif;

[F-4] the method according to [F-3], wherein the C-X-C motif is C-T-C(Cys-Thr-Cys), C-L-C(Cys-Leu-Cys), or C-S-C(Cys-Ser-Cys);

[F-5] the method according to any one of [F-1] to [F-4], wherein the parent CXCR3 ligand is either a naturally-occurring human CXCL10 or a variant thereof, a naturally-occurring human CXCL11 or a variant thereof, or a naturally-occurring human CXCL9 or a variant thereof;

[F-6] the method according to [F-1] to [F-5], wherein the $1^{st}$ amino acid at the N-terminus of the parent CXCR3 ligand is F;

[F-7] the method according to any one of [F-1] to [F-6], wherein the N-terminal sequence of the parent CXCR3 ligand is F-P-M-F-K-R-G-R (SEQ ID NO: 91); and

[F-8] the method according to [F-7], wherein the C-X-C motif is located at the C-terminus of the N-terminal sequence "F-P-M-F-K-R-G-R (SEQ ID NO: 91)".

The present disclosure also encompasses the embodiments exemplified below:

[G-1] a method of producing a CXCR3 ligand having resistance to DPPIV, wherein the method carries out any of the following modifications to a parent CXCR3 ligand in which the $2^{nd}$ amino acid from the N-terminus is P:

(1) further adding A, D, E, F, G, H, I, K, L, M, N, P, Q, S, T, V, W, or Y to the N-terminus of the parent CXCR3 ligand;

(2) substituting the $2^{nd}$ amino acid from the N-terminus of the parent CXCR3 ligand from P to A, D, E, G, H, I, M, N, Q, R, S, T, V, W, or Y; and (3) inserting A, D, E, F, G, H, L, M, N, P, Q, S, T, W, or Y between the $1^{st}$ and $2^{nd}$ amino acids at the N-terminus of the parent CXCR3 ligand;

[G-2] a method of producing a CXCR3 ligand having resistance to DPPIV, wherein the method carries out, to a parent CXCR3 ligand in which the $2^{nd}$ amino acid from the N-terminus is P, the modification of further adding A, D, E, G, M, N, Q, S, T, V, or Y to the N-terminus of the parent CXCR3 ligand;

[G-3] the method according to [G-1] or [G-2], wherein the parent CXCR3 ligand further has a C-X-C motif;

[G-4] the method according to [G-3], wherein the C-X-C motif is C-T-C(Cys-Thr-Cys), C-L-C(Cys-Leu-Cys), or C-S-C(Cys-Ser-Cys);

[G-5] the method according to any one of [G-1] to [G-4], wherein the parent CXCR3 ligand is either a naturally-occurring human CXCL10 or a variant thereof, a naturally-occurring human CXCL11 or a variant thereof, or a naturally-occurring human CXCL9 or a variant thereof;

[G-6] the method according to [G-1] to [G-5], wherein the $1^{st}$ amino acid at the N-terminus of the parent CXCR3 ligand is F;

[G-7] the method according to any one of [G-1] to [G-6], wherein the N-terminal sequence of the parent CXCR3 ligand is F-P-M-F-K-R-G-R (SEQ ID NO: 91);

[G-8] the method according to [G-7], wherein the parent C-X-C motif is located at the C-terminus of the N-terminal sequence "F-P-M-F-K-R-G-R (SEQ ID NO: 91)"; and

[G-9] a CXCR3 ligand produced by a method of any one of [G-1] to [G-8].

BRIEF DESCRIPTION OF DRAWINGS

Figure 3B:
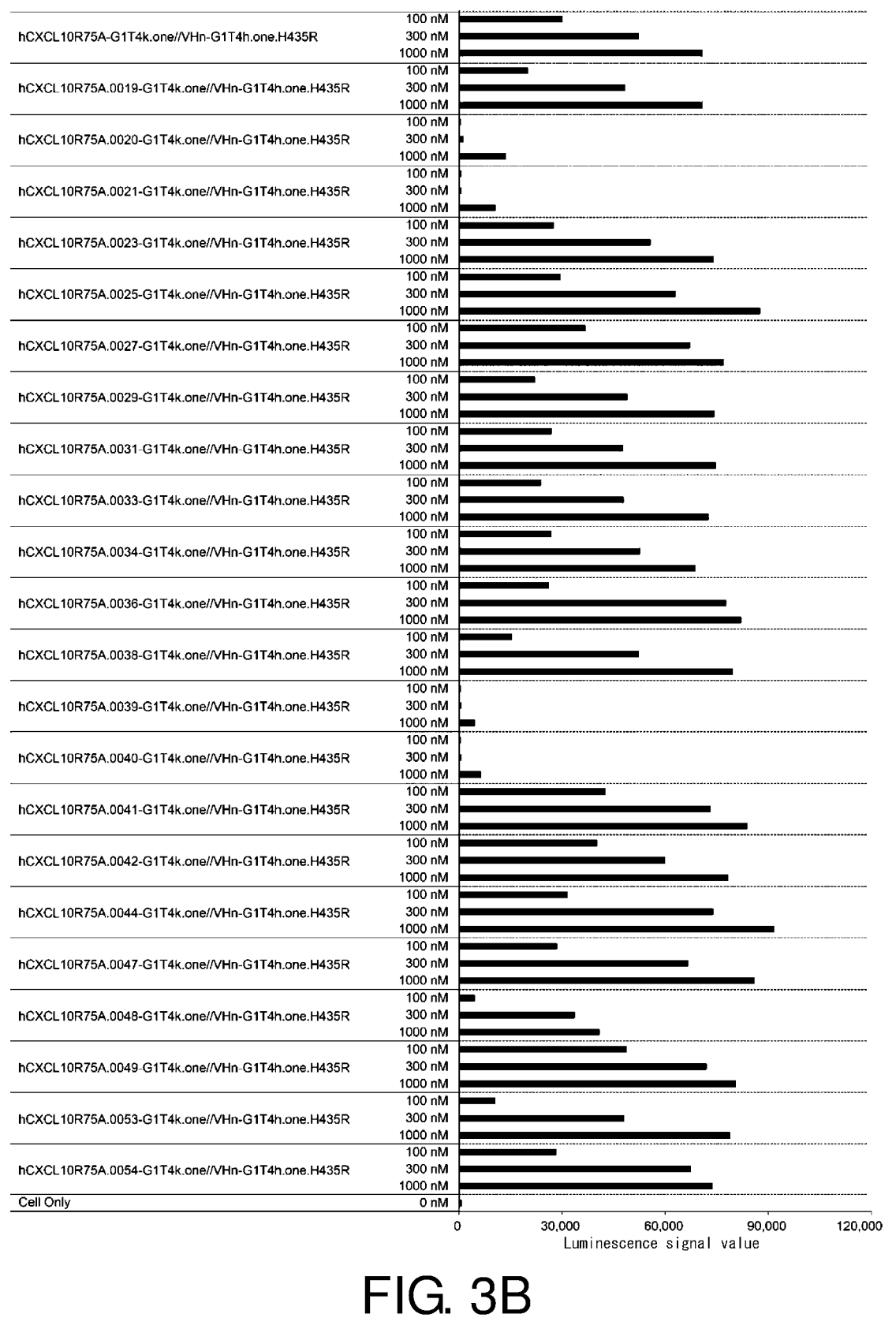

FIG. 3b shows the cell migration-inducing activity of each hCXCL10 variant Fc fusion.

FIG. 6-2 shows a continuation of FIG. 6-1.

FIG. 6-3 shows a continuation of FIG. 6-2. The activities shown in FIG. 6-1 to FIG. 6-3 are from the same experiment round.

DESCRIPTION OF EMBODIMENTS

Figure 1A:
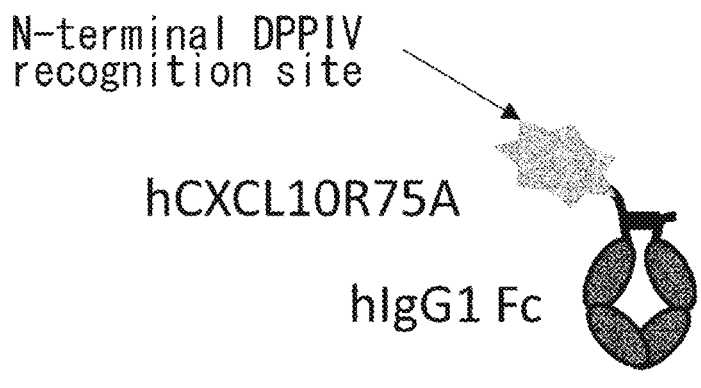
FIG. 1A shows a schematic diagram of an hCXCL10 variant Fc fusion.

The following definitions and detailed descriptions are provided to facilitate the understanding of the present disclosure explained herein.

Amino Acids

In the present specification, each amino acid is indicated by one-letter code or three-letter code, or both, as represented by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Amino Acid Modifications

For the modification of an amino acid in the amino acid sequence of a CXCR3 ligand, a method known in the art such as site-directed mutagenesis (Kunkel et al. (Proc. Natl. Acad. Sci. USA (1985) 82, 488-492)) or overlap extension PCR can be appropriately used. Several methods known in the art can also be used as amino acid modification methods for substituting an amino acid with an amino acid other than a naturally-occurring amino acid (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express)) in which a non-naturally-occurring amino acid is bound to an amber suppressor tRNA complementary to the UAG codon (amber codon), which is a stop codon, is also preferably used.

In the present specification, the term "and/or" used to represent amino acid modification sites is meant to include every combination in which "and" and "or" are appropriately combined. Specifically, for example, the phrase "amino acids at positions 33, 55, and/or 96 are substituted" includes the following variations of amino acid modification: (a) position 33, (b) position 55, (c) position 96, (d) positions 33 and 55, (e) positions 33 and 96, (f) positions 55 and 96, and (g) positions 33, 55, and 96. Alternatively, the phrase "amino acids at positions 33, 55, and/or 96 are substituted" is synonymous to the phrase "an amino acid at least one (one, two, or three) position selected from the group consisting of positions 33, 55, and 96 is substituted".

In the present specification, an expression in which the one-letter codes or three-letter-codes of amino acids before and after modification are written prior to and subsequent to a number representing a particular position can be appropriately used for representing an amino acid substitution. For example, the modification P2A or Pro2Ala used for substituting an amino acid contained in a CXCR3 ligand represents the substitution of Pro at position 2 from the N-terminus of the CXCR3 ligand with Ala. Specifically, the number represents an amino acid position as counted from the N-terminus of the CXCR3 ligand; the one-letter code or three-letter code of the amino acid written prior to the number represents the amino acid before the substitution; and the one-letter code or three-letter code of the amino acid subsequent to the number represents the amino acid after the substitution.

In the present specification, an expression showing "ins" and a one-letter code or three-letter-code of an inserted amino acid subsequent to a particular position of insertion can be appropriately used for representing an amino acid insertion. In order to express the position of insertion, an expression showing the one-letter code or three-letter code of the amino acid before and after the position of insertion and the position can be appropriately used. For example, the modification V1_P2insA or Vall_Pro2insAla, which is used when inserting an amino acid into the amino acid sequence contained in a CXCR3 ligand, represents the insertion of Ala between the amino acid Val at position 1 and the amino acid Pro at position 2 from the N-terminus of the CXCR3 ligand. When inserting an amino acid to the N-terminal side of the amino acid Val at position 1 from the N-terminus of the CXCR3 ligand, for example, the expression G-1_VlinsA or Gly-1_VallinsAla is used to show the insertion of Ala between Val at position 1 from the N-terminus of the CXCR3 ligand and Gly in the signal sequence positioned next to said Val at the N-terminal side, and since Gly in the signal sequence is the amino acid at position 1 further at the N-terminal side than the N-terminus of the CXCR3 ligand, the position is expressed as "−1".

CXCR3

Chemokine receptor CXCR3 (also called G Protein-coupled Receptor 9 (GPR9) and CD183) belongs to the CXC chemokine family and is a G Protein-coupled receptor that binds to the chemokines CXCL9, CXCL10, and CXCL11. CXCR3 is expressed primarily in activated T-helper type 1 (Th1) lymphocytes, but is also present in natural killer cells, macrophages, dendritic cells, and B lymphocyte subsets. The chemokines CXCL9, CXCL10, and CXCL11 are three naturally-occurring CXCR3 ligands. The interaction of CXCR3 and its ligands (hereinafter referred to as the CXCR3 axis) is involved in guiding receptor-bearing cells to specific parts of the body, especially sites of inflammation, immune impairment, and immune dysfunction. Unless otherwise indicated, the term "CXCR3" as used herein indicates any natural CXCR3 from any vertebrate source, including mammals such as primates (e.g., humans) and rodents (e.g., mice and rats). The entire amino acid sequence of human CXCR3 is shown by Refseq: NP_001495 (SEQ ID NO: 88).

Chemokines and CXC Chemokines

Chemokines are a family of homogeneous serum proteins of 7 to 16 kDa originally characterized by their ability to induce leukocyte migration. Most of chemokines have four characteristic cysteines (Cys) and are classified into C-X-C (or alpha, CXC), C-C(or beta), C (or gamma), and CX3C (or delta) chemokine classes, according to motifs displayed by the first two cysteines. Two disulfide bonds are formed between the first and third cysteines and between the second and fourth cysteines. In general, the disulfide bridges are considered necessary. Clark-Lewis and collaborators have reported that the disulfide bonds are crucial for the chemokine activity of at least CXCL10 (Clark-Lewis et al., J. Biol. Chem. 269: 16075-16081, 1994).

Subfamilies of C-X-C(or alpha, CXC) are further classified, according to the presence of an ELR motif (Glu-Leu-Arg) preceding the first cysteine, into two groups: ELR-CXC chemokines and non-ELR-CXC chemokines (see e.g., Clark-Lewis, supra; and Belperio et al., J. Leukoc. Biol. 68: 1-8, 2000). CXCL10, CXCL11, and CXCL9 are all non-ELR-CXC chemokines.

CXCL10

CXC motif chemokine 10 (C-X-C motif chemokine ligand 10, CXCL10) is a C-X-C chemokine, which is also called interferon-induced protein-10 (IP-10). It is induced by interferon-γ and TNF-α and produced by keratinocytes, endothelial cells, fibroblasts, and monocytes. CXCL10 is thought to play a role in the recruitment of activated T cells to sites of tissue inflammation (Dufour, et al., J Immunol., 168: 3195-204, 2002). In addition, CXCL10 may play a role in hypersensitivity reactions. It may also play a role in the development of inflammatory demyelinating neuropathy (Kieseier, et al., Brain 125: 823-34, 2002).

Researches indicate that CXCL10 may be useful in the engraftment of stem cells following transplantation (Nagasawa, T., Int. J. Hematol. 72: 408-11, 2000), in the mobilization of stem cells (Gazitt, Y., J. Hematother Stem Cell Res 10: 229-36, 2001; and Hattori et al., Blood 97: 3354-59, 2001), and in an enhancement of antitumor immunity (Nomura et al., Int. J. Cancer 91: 597-606, 2001; and Mach and Dranoff, Curr. Opin. Immunol. 12: 571-75, 2000). For example, previous reports known to those skilled in the art discuss the biological activity of chemokine (Bruce, L. et al., Methods in Molecular Biology (2000) vol. 138, pp. 129-134; Raphaele, B. et al., Methods in Molecular Biology (2000) vol. 138, pp. 143-148; and Paul D. Ponath et al., Methods in Molecular Biology (2000) vol. 138, pp. 113-120). The physiological activity of CXCL10 is exerted by binding to the chemokine receptor CXCR3 expressed on the cell surface (Booth V. et al, Biochemistry. 41 (33): 10418-25).

Unless otherwise indicated, the term "CXCL10" as used herein refers to any natural CXCL10 from any vertebrate source, including mammals such as primates (e.g., humans) and rodents (e.g., mice and rats). The term refers not to the "full-length", unprocessed CXCL10, but to mature CXCL10 secreted extracellularly as a result of intracellular processing. As used herein, those that have not undergone processing are referred to as CXCL10 precursors. The term also encompasses naturally-occurring mutants of CXCL10 such as splice mutants and allelic mutants. Naturally-occurring human CXCL10 is expressed as a CXCL10 precursor (Refseq Accession number: NP_001556) and then secreted extracellularly as a protein with the sequence set forth in SEQ ID NO: 60. The complete amino acid sequence of the rhesus monkey CXCL10 precursor is indicated by Refseq Accession number: AKK95955, and the complete amino acid sequence of the mouse CXCL10 precursor is indicated by Refseq Accession number: NP_067249.

Natural CXCL10 or naturally-occurring CXCL10 mutants to which artificial amino acid modifications have been added are called "CXCL10 variants".

CXCL11

C-X-C motif chemokine 11 (CXC motif chemokine ligand 11, CXCL11) is a C-X-C chemokine, which is also called I-TAC (Interferon-inducible T-cell alpha chemoattractant) or IP-9 (Interferon-gamma-inducible Protein 9). CXCL11 gene expression is strongly induced by IFN-γ and IFN-β, and also by IFN-α (Rani M R, The Journal of Biological Chemistry. 271 (37): 22878-84).

CXCL11 has a biological activity to activate T cells. CXCL11 is known to exert its biological activity by binding to the chemokine receptor CXCR3 expressed on the cell surface, and naturally-occurring CXCL11 is said to bind to CXCR3 more strongly than naturally-occurring CXCL10 and naturally-occurring CXCL9 (Cole K E., The Journal of Experimental Medicine. 187 (12): 2009-21; Tensen CP, The Journal of Investigative Dermatology. 112 (5): 716-22).

The term "CXCL11" as used herein refers to any natural CXCL11 from any vertebrate source, including mammals such as primates (e.g., humans) and rodents (e.g., mice and rats), unless otherwise indicated. The term refers not to a "full-length", unprocessed CXCL11, but to a mature CXCL11 that is secreted extracellularly as a result of intracellular processing. As used herein, those that have not undergone processing are referred to as CXCL11 precursors. The term also includes naturally-occurring mutants of CXCL11, such as splice mutants and allelic mutants. Natural human CXCL11 is expressed as a CXCL11 precursor (Refseq Accession number: NP_005400) and then secreted extracellularly as a protein with the sequence set forth in SEQ ID NO: 61.

Natural CXCL11 or naturally-occurring CXCL11 mutants to which artificial amino acid modifications have been added are called "CXCL11 variants".

CXCL9

C-X-C motif chemokine 9 (C-X-C motif chemokine ligand 9, CXCL9) is a C-X-C chemokine, which is also called Monokine induced by gamma interferon (MIG). CXCL9 is an IFN-γ-induced T-cell chemoattractant and is known to exert its biological activity by binding to the chemokine receptor CXCR3 expressed on the cell surface.

The term "CXCL9" as used herein refers to any natural CXCL9 from any vertebrate source, including mammals such as primates (e.g., humans) and rodents (e.g., mice and rats), unless otherwise indicated. The term refers not to "full-length", unprocessed CXCL9, but to mature CXCL9 that is secreted extracellularly as a result of intracellular processing. As used herein, those that have not undergone processing are referred to as CXCL9 precursors. The term also includes naturally-occurring mutants of CXCL9, such as splice mutants and allelic mutants. Natural human CXCL9 is expressed as a CXCL9 precursor (Refseq Accession number: NP_002407) and then secreted extracellularly as a protein with the sequence set forth in SEQ ID NO: 62.

Natural CXCL9 or naturally-occurring CXCL9 mutants to which artificial amino acid modifications have been added are called "CXCL9 variants".

Chimeric proteins can be prepared by fusing parts of CXCL10, CXCL11, CXCL9 and such with each other. For example, a human CXCL10-human CXCL11 chimeric protein (hITIP) (SEQ ID NO: 63) in which the $1^{st}$ to $24^{th}$ amino acid residues of human CXCL11 (SEQ ID NO: 61) and the $25^{th}$ to $77^{th}$ amino acid residues of a human CXCL10 variant (SEQ ID NO: 1) are bound can be prepared. Such chimeric proteins can also be called CXCR3 ligands as long as they can bind to CXCR3. Furthermore, even in such chimeric proteins, the two N-terminal amino acids may be cleaved by DPPIV. The human CXCL10-human CXCL11 chimeric protein (hITIP) (SEQ ID NO: 63), in which the $1^{st}$ to $24^{th}$ amino acid residues of human CXCL11 (SEQ ID NO: 61) and the $25^{th}$ to $77^{th}$ amino acid residues of a human CXCL10 variant (SEQ ID NO: 1) are bound, and to which further amino acid modifications have been added is called an "hITIP variant".

Method for Measuring the Binding Between a CXCR3 Ligand and CXCR3

The binding activity of a CXCR3 ligand to CXCR3 can be assessed by a well-known method such as FACS, an ELISA format, a BIACORE method using amplified luminescent proximity homogeneous assay (ALPHA) screening or surface plasmon resonance (SPR) phenomena, or bio-layer interferometry (BLI) (Octet) (Proc. Natl. Acad. Sci. USA (2006) 103 (11), 4005-4010).

ALPHA screening is carried out based on the following principle according to ALPHA technology that uses two beads, a donor and an acceptor. Luminescence signals are detected only when molecules bound with the donor beads interact with molecules bound with the acceptor beads and when the two beads are close to one another. Laser-excited photosensitizers in the donor beads convert ambient oxygen into singlet oxygen in an excited state. The singlet oxygen molecules spread around the donor beads and when they reach the nearby acceptor beads, they induce chemiluminescent reaction in the beads to result in light emission. When the molecule bound with the donor bead and the molecule bound with the acceptor bead do not interact, chemiluminescent reaction does not occur because singlet oxygen produced by the donor bead does not reach the acceptor bead.

For example, a biotin-labeled CXCR3 ligand is bound to the donor bead, and a glutathione S transferase (GST)-tagged CXCR3 peptide is bound to the acceptor bead. The N-terminal extracellular domain region ($1^{st}$ to $53^{rd}$ amino acids, SEQ ID NO: 89) or a partial fragment thereof ($22^{nd}$ to $42^{nd}$ amino acids, SEQ ID NO: 90, Biochemistry (2002) 41, 10418-10425) can be used as the CXCR3 peptide. In addition, it is more desirable that the Y residue at position 27 and/or the Y residue at position 29 of CXCR3 have/has undergone sulfation modification (MOLECULAR AND CELLULAR BIOLOGY, Aug. 2006, p. 5838-5849). In the absence of competing untagged CXCR3 ligands, the CXCR3 ligand and CXCR3 peptide interact to produce a signal at 520-620 nm. The untagged CXCR3 ligand competes with the tagged CXCR3 ligand for interaction with the CXCR3 peptide. Decrease in fluorescence resulting from the competition can be quantified to determine relative binding affinity. Biotinylation of a CXCR3 ligand, such as CXCL10, using sulfo-NHS-biotin or the like is known in the art. A method which involves, for example, fusing a polynucleotide encoding the CXCR3 peptide in-frame with a polynucleotide encoding GST to form a fused gene, expressing the GST-fused CXCR3 peptide in cells or the like carrying a vector that permits expression of the fused gene, and purifying the GST-fused CXCR3 peptide using a glutathione column, can be appropriately adopted as a method for tagging a CXCR3 peptide with GST. The obtained signals are preferably analyzed using, for example, the software GRAPHPAD PRISM (GraphPad Software, Inc., San Diego) adapted to a one-site competition model based on non-linear regression analysis.

One (CXCR3 ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other one (analyte, the full-length CXCR3 or the aforementioned CXCR3 peptides can be used as the analyte when fixing a CXCR3 ligand) of the substances between which the interaction is to be observed is poured onto the surface of the sensor chip, and when the analyte binds with the CXCR3 ligand, the mass of the immobilized CXCR3 ligand molecule increases and results in the change of refractive index of the solvent on the sensor chip surface. This change in refractive index shifts the position of the SPR signal (in contrast, the position of the signal returns when dissociation occurs). The Biacore system plots on the ordinate the amount of the above-mentioned shift, i.e., change in mass on the sensor chip surface, and displays time-dependent change in mass as assay data (sensorgram). Kinetics (association rate constant (ka) and dissociation rate constant (kd)) is determined from the curve of the sensorgram, and dissociation constant (KD) is determined from the ratio between the two constants. Inhibition assay or equilibrium analysis is also preferably used in the BIACORE method. Examples of inhibition assay are described in Proc. Natl. Acad. Sci. USA (2006) 103 (11), 4005-4010, and examples of equilibrium analysis are described in Methods Enzymol. 2000; 323: 325-40. Using a similar method, the binding of a CXCR3 ligand to CXCR3 can be measured by immobilizing the full-length CXCR3 or the aforementioned CXCR3 peptides on a thin gold film of a sensor chip and pouring the CXCR3 ligand as the analyte. The full-length CXCR3 or the aforementioned CXCR3 peptides immobilized on the thin gold film of the sensor chip may be a purified protein or peptide. Alternatively, a cell expressing them or a cell membrane fraction thereof may also be used.

The CXCR3 ligand of the present disclosure can specifically bind to the full-length CXCR3 or to the aforementioned CXCR3 peptides with a dissociation constant (KD) of 100 µM, 10 µM, 1 µM, 100 nM, 50 nM, 10 nM, 5 nM, 1 nM, 500 µM, 400 µM, 350 µM, 300 µM, 250 µM, 200 µM, 150 µM, 100 µM, 50 µM, 25 µM, 10 µM, 5 µM, 1 µM, 0.5 µM, or 0.1 µM or less.

Alternatively, the binding activity of a CXCR3 ligand to the immobilized full-length CXCR3 or an aforementioned CXCR3 peptide can be evaluated based on the ELISA principle. For example, the full-length CXCR3 or an aforementioned CXCR3 peptide is immobilized in the wells of an ELISA plate. A CXCR3 ligand solution is brought into contact with the immobilized full-length CXCR3 or aforementioned CXCR3 peptide in the wells, and a CXCR3 ligand that binds to the immobilized full-length CXCR3 or aforementioned CXCR3 peptide is detected by an antibody that binds to the CXCR3 ligand. Alternatively, the CXCR3 ligand is immobilized in the wells of an ELISA plate, full-length CXCR3 or aforementioned CXCR3 peptide solution is brought into contact with the immobilized CXCR3 ligand in the wells, and the full-length CXCR3 or an aforementioned CXCR3 peptide that binds to the immobilized CXCR3 ligand is detected by an antibody that binds to the full-length CXCR3 or the aforementioned CXCR3 peptide.

As a method of measuring the binding between a CXCR3 ligand and CXCR3, there is also the method of labelling the CXCR3 ligand using a radioisotope. Specifically, a radioisotope-labeled CXCR3 ligand is prepared, added to CXCR3-expressing cells, and incubated. The incubated sample is passed through a filter to adsorb the CXCR3 ligand bound to CXCR3 onto the filter together with the cells. The amount of CXCR3 ligand adsorbed on the filter can be measured by drying the filter and measuring the radiation amount. There is a report of applying this method to CXCL10 (Molecular and Cellular Biology, Aug. 2006, p. 5838-5849, Vol. 26, No. 15, The Journal of Biological Chemistry Vol. 278, No. 19, Issue of May 9, pp. 17066-17074, 2003).

In addition, by measuring the 15N-1H HSQC NMR spectrum and 2D NOESY NMR spectrum of a 15N-labeled CXCR3 ligand and comparing the NMR spectra obtained before and after the addition of a CXCR3 peptide, residues involved in CXCR3 binding within the CXCR3 ligand and the strength of the bond can also be analyzed (Biochemistry, 2002, 41, 10418-10425).

CXCR3 Ligands

The term "CXCR3 ligand" as used herein refers to a molecule capable of binding to CXCR3. For example, proteins comprising sites that interact with the ligand-binding site of CXCR3 are included in the CXCR3 ligands of the present disclosure. The term refers to mature CXCR3 ligands that are secreted extracellularly as a result of intracellular processing, and not to "full-length" proteins that have not undergone processing. As used herein, those that have not undergone processing are referred to as CXCR3 ligand precursors.

In a particular embodiment, the CXCR3 ligand provided herein has resistance to DPPIV and the activity of causing migration of cells expressing CXCR3.

DPPIV (Dipeptidyl peptidase IV, Dipeptidyl peptidase 4, DPP4; EC3.4.14.5) is an enzyme (serine protease) that inactivates incretin, which is an intestinal hormone, and is present on the cell membrane as well as in blood as a soluble protein. It is also called adenosine deaminase-binding protein (ADABP) because it also has the function of binding to adenosine deaminase (ADA; EC 3.5.4.4) and modulating intracellular signal transduction. DPPIV has the function of cleaving a dipeptide from a peptide having a proline or alanine residue at the 2nd position from the amino terminal side.

Human DPPIV is a 110 kDa protein composed of 766 amino acids, and its amino acid sequence is shown by Refseq accession number: NP_001926.2.

Evaluation of whether a target protein is cleaved by DPPIV can be done by LC/MS analysis after incubating DPPIV and the target protein. Specifically, when 0.2 mg/ml of the target protein and DPPIV at a final concentration of 200 nM are reacted at 37° C. for 1 hour, mass spectrometry is then done by LC/MS, and the mass of the target protein decreases due to the reaction, this suggests that the target protein was cleaved by DPPIV. In addition, when the mass of the protein is reduced and the mass of the reduced amount and the theoretical mass of the two N-terminal amino acids of the target protein match, this suggests that the two N-terminal amino acids of the target protein were cleaved by DPPIV. When carrying out such a DPPIV cleavage assessment on a CXCR3 ligand of the present disclosure, the protein to be incubated with DPPIV may be the CXCR3 ligand itself, or may be a fusion protein in which the CXCR3 ligand is fused with another polypeptide (e.g., an antibody Fc region).

"Resistance to DPPIV" in the present disclosure refers to the property of the target protein of not being cleaved by DPPIV. More specifically, it means that the mass of the target protein after DPPIV treatment does not decrease when a cleavage evaluation as described above is carried out. More specifically, it means that the mass reduction of the target protein after DPPIV treatment does not match the theoretical mass of the two N-terminal amino acids of the target protein when a cleavage evaluation as described above is carried out.

The activity of a target protein to cause migration of cells expressing CXCR3 can be measured using a transfectant or cells isolated from a living body which express CXCR3. As an example of a specific method, Ba/F3 transfectant cells expressing mouse CXCR3 (mCXCR3) (hereinafter BaF3/mCXCR3) or Ba/F3 transfectant cells expressing human CXCR3 (hCXCR3) (hereinafter BaF3/hCXCR3) and HTS Transwell™-96 Permeable Supports with 5.0 µm Pore Polycarbonate Membrane (Cat. 3387, Corning) are used, with the target protein as analyte. After adjusting the final concentration of each analyte to be analyzed in solution to a concentration selected from 33 nM, 100 nM, 300 nM, and 1000 nM, 235 μL of each solution is transferred to the lower chamber. Then, BaF3/mCXCR3 or BaF3/hCXCR3 cells are seeded into the upper chamber at 75 μL/well so as to be $2.0 \times 10^5$ cells/well, and the reaction is carried out for 6 hours or 3 hours, under the conditions of 5% carbon dioxide and 37° C. After reacting for 3 hours, 6 hours, or 18 hours, 100 μL of the solution in the lower chamber is transferred to OptiPlate-96 (Cat. 6005299, PerkinElmer) and 100 μL of CellTiter-Glo™ Luminescent Cell Viability Assay solution (Cat. G7571, Promega) is added. After reacting at room temperature for 10 minutes, the luminescence value is measured with a SpectraMax M3 multimode microplate reader (Molecular Devices) to evaluate the level of migration of cells into the lower chamber. The amount of cells that migrated into the lower chamber is reflected by the luminescence intensity.

In a particular embodiment, the activity of a CXCR3 ligand provided herein to cause migration of cells expressing CXCR3 is 30% or more of the activity of naturally-occurring human CXCL10 to cause migration of cells expressing CXCR3. Specifically, it is preferable to include naturally-occurring human CXCL10 as a control in the system for analyzing the activity to cause migration of CXCR3-expressing cells and to compare the fluorescence intensities obtained from the same experiment round of the CXCR3 ligand whose activity is to be compared and the control in order to make the state of the CXCR3 cells used for the measurement uniform. 30% or more of the activity of naturally-occurring human CXCL10 to cause migration of cells expressing CXCR3 does not limit the concentration of the analyte in the system for analyzing the activity to cause migration of cells expressing CXCR3, but it can indicate 30% or more of the activity of naturally-occurring human CXCL10 to cause migration of cells expressing CXCR3 in at least one of the concentrations of 100 nM, 300 nM, and 1000 nM.

When a fusion protein comprising a CXCR3 ligand is used as the analyte for analyzing the activity to cause migration of cells expressing CXCR3, it is preferable that the naturally-occurring human CXCL10 used as the control has a molecular format similar to that of the fusion protein comprising the CXCR3 ligand (i.e., that a control of the fusion protein is prepared by using naturally-occurring human CXCL10 in place of the CXCR3 ligand provided herein).

In a particular embodiment, the activity of the CXCR3 ligand provided herein to cause migration of cells expressing CXCR3 is 25% or more of the activity of naturally-occurring human CXCL11 to cause migration of cells expressing CXCR3. Specifically, it is preferable to include naturally-occurring human CXCL11 as a control in the system for analyzing the activity to cause migration of CXCR3-epxressing cells and to compare the fluorescence intensities obtained from the same experiment round of the CXCR3 ligand whose activity is to be compared and the control in order to make the state of the CXCR3 cells used for the measurement uniform. 25% or more of the activity of naturally-occurring human CXCL11 to cause migration of cells expressing CXCR3 does not limit the concentration of the analyte in the system for analyzing the activity to cause migration of cells expressing CXCR3, but it can indicate 25% or more of the activity of naturally-occurring human CXCL11 to cause migration of cells expressing CXCR3 in at least one of the concentrations of 33 nM, 100 nM, and 300 nM.

When a fusion protein comprising a CXCR3 ligand is used as the analyte for analyzing the activity to cause migration of cells expressing CXCR3, it is preferable that the naturally-occurring human CXCL11 used as the control has a molecular format similar to that of the fusion protein comprising the CXCR3 ligand (i.e., that a control of the fusion protein is prepared by using naturally-occurring human CXCL11 in place of the CXCR3 ligand provided herein).

In a particular embodiment, the activity of the CXCR3 ligand provided herein to cause migration of cells expressing CXCR3 is 25% or more of the activity of hITIP to cause migration of cells expressing CXCR3. Specifically, it is preferable to include hITIP as a control in the system for analyzing the activity to cause migration of CXCR3-epxressing cells and to compare the fluorescence intensities obtained from the same experiment round of the CXCR3 ligand whose activity is to be compared and the control in order to make the state of the CXCR3 cells used for the measurement uniform. 25% or more of the activity of hITIP to cause migration of cells expressing CXCR3 does not limit the concentration of the analyte in the system for analyzing the activity to cause migration of cells expressing CXCR3, but it can indicate 25% or more of the activity of hITIP to cause migration of cells expressing CXCR3 in at least one of the concentrations of 33 nM, 100 nM, and 300 nM.

When a fusion protein comprising a CXCR3 ligand is used as the analyte for analyzing the activity to cause migration of cells expressing CXCR3, it is preferable that the hITIP used as the control has a molecular format similar to that of the fusion protein comprising the CXCR3 ligand (i.e., that a control of the fusion protein is prepared by using hITIP in place of the CXCR3 ligand provided herein).

In a particular embodiment, the CXCR3 ligand concentration at which the activity of the CXCR3 ligand provided herein to cause migration of cells expressing CXCR3 is at a maximum is lower than the concentration of at least one protein selected from naturally-occurring human CXCL10, naturally-occurring human CXCL11, and hITIP at which the activity to cause migration of cells expressing CXCR3 is at a maximum.

In a particular embodiment, the CXCR3 ligand provided herein does not have P as the $2^{nd}$ amino acid from the N-terminus. In a particular embodiment, the CXCR3 ligand provided herein does not have A as the $2^{nd}$ amino acid from the N-terminus.

In a particular embodiment, the CXCR3 ligand provided herein has any of the following sequences (a1) to (a7) at the N-terminus:

(a1) V-X1-L (X1 is F, G, I, K, L, M, T, V, W, or Y);

(a2) X2-V-P (X2 is A, F, G, H, I, K, L, M, N, P, Q, R, S, T, V, W, or Y);

(a3) V-X3-P (X3 is A, F, G, H, I, K, L, M, P, Q, R, S, T, V, W, or Y);

(a4) P-L-S;

(a5) X4-F-P (X4 is A, D, E, F, G, H, I, K, L, M, N, P, Q, S, T, V, W, or Y);

(a6) F-X5-M (X5 is A, D, E, G, H, I, M, N, Q, R, S, T, V, W, or Y); and (a7) F-X6-P (X6 is A, D, E, F, G, H, L, M, N, P, Q, S, T, W, or Y).

In a particular embodiment, the CXCR3 ligand provided herein has any of the following sequences (b1) to (b7) at the N-terminus:

(b1) V-X1-L-S-R-T-V-R (X1 is F, G, I, K, L, M, T, V, W, or Y) (SEQ ID NO: 205);

(b2) X2-V-P-L-S-R-T-V-R (X2 is A, F, G, H, I, K, L, M, N, P, Q, R, S, T, V, W, or Y) (SEQ ID NO: 206);

(b3) V-X3-P-L-S-R-T-V-R (X3 is A, F, G, H, I, K, L, M, P, Q, R, S, T, V, W, or Y) (SEQ ID NO: 207);

(b4) P-L-S-R-T-V-R (SEQ ID NO: 208);

(b5) X4-F-P-M-F-K-R-G-R (X4 is A, D, E, F, G, H, I, K, L, M, N, P, Q, S, T, V, W, or Y) (SEQ ID NO: 209);

(b6) F-X5-M-F-K-R-G-R (X5 is A, D, E, G, H, I, M, N, Q, R, S, T, V, W, or Y) (SEQ ID NO: 210); and (b7) F-X6-P-M-F-K-R-G-R (X6 is A, D, E, F, G, H, L, M, N, P, Q, S, T, W, or Y) (SEQ ID NO: 211).

In a particular embodiment, the CXCR3 ligand provided herein has any of the following sequences (a1) to (a5) at the N-terminus:

(a1) V-X1-L (X1 is F, G, I, L, M, T, V, W, or Y);

(a2) X2-V-P (X2 is A, G, I, L, N, Q, S, T, or W);

(a3) V-X3-P (X3 is A, F, G, I, M, P, T, or V);

(a4) P-L-S; and (a5) X4-F-P (X4 is A, D, E, G, M, N, Q, S, T, V, or Y).

In a particular embodiment, the CXCR3 ligand provided herein has any of the following sequences (b1) to (b5) at the N-terminus:

(b1) V-X1-L-S-R-T-V-R (X1 is F, G, I, L, M, T, V, W, or Y) (SEQ ID NO: 212);

(b2) X2-V-P-L-S-R-T-V-R (X2 is A, G, I, L, N, Q, S, T, or W) (SEQ ID NO: 213);

(b3) V-X3-P-L-S-R-T-V-R (X3 is A, F, G, I, M, P, T, or V) (SEQ ID NO: 214);

(b4) P-L-S-R-T-V-R (SEQ ID NO: 208); and (b5) X4-F-P-M-F-K-R-G-R (X4 is A, D, E, G, M, N, Q, S, T, V, or Y) (SEQ ID NO: 215).

In a particular embodiment, the CXCR3 ligand provided herein has a C-X-C motif. The two cysteines contained in the C-X-C motif can each form disulfide bonds with cysteines other than those contained in the C-X-C motif comprised in the CXCR3 ligand. The C-X-C motif in the CXCR3 ligand can be selected from C-T-C(Cys-Thr-Cys), C-L-C (Cys-Leu-Cys), and C-S-C(Cys-Ser-Cys).

The C-X-C motif in the CXCR3 ligand can be located next to the C-terminus of any of the following N-terminal sequences (b1) to (b7):

(b1) V-X1-L-S-R-T-V-R (X1 is F, G, I, K, L, M, T, V, W, or Y) (SEQ ID NO: 205);

(b2) X2-V-P-L-S-R-T-V-R (X2 is A, F, G, H, I, K, L, M, N, P, Q, R, S, T, V, W, or Y) (SEQ ID NO: 206);

(b3) V-X3-P-L-S-R-T-V-R (X3 is A, F, G, H, I, K, L, M, P, Q, R, S, T, V, W, or Y) (SEQ ID NO: 207);

(b4) P-L-S-R-T-V-R (SEQ ID NO: 208);

(b5) X4-F-P-M-F-K-R-G-R (X4 is A, D, E, F, G, H, I, K, L, M, N, P, Q, S, T, V, W, or Y) (SEQ ID NO: 209);

(b6) F-X5-M-F-K-R-G-R (X5 is A, D, E, G, H, I, M, N, Q, R, S, T, V, W, or Y) (SEQ ID NO: 210); and (b7) F-X6-P-M-F-K-R-G-R (X6 is A, D, E, F, G, H, L, M, N, P, Q, S, T, W, or Y) (SEQ ID NO: 211).

The C-X-C motif in the CXCR3 ligand can be located next to the C-terminus of any of the following sequences (b1) to (b5):

(b1) V-X1-L-S-R-T-V-R (X1 is F, G, I, L, M, T, V, W, or Y) (SEQ ID NO: 212);

(b2) X2-V-P-L-S-R-T-V-R (X2 is A, G, I, L, N, Q, S, T, or W) (SEQ ID NO: 213);

(b3) V-X3-P-L-S-R-T-V-R (X3 is A, F, G, I, M, P, T, or V) (SEQ ID NO: 214);

(b4) P-L-S-R-T-V-R (SEQ ID NO: 208); and (b5) X4-F-P-M-F-K-R-G-R (X4 is A, D, E, G, M, N, Q, S, T, V, or Y) (SEQ ID NO: 215).

In a particular embodiment, the CXCR3 ligand provided herein can further have any of the following (c1) to (c5) at the C-terminus of the C-X-C motif:

(c1) the sequence from the 12th amino acid to the 77th amino acid of SEQ ID NO: 60;

(c2) the sequence from the 12th amino acid to the 73rd amino acid of SEQ ID NO: 61;

(c3) the sequence from the 12th amino acid to the 103rd amino acid of SEQ ID NO: 62;

(c4) the sequence from the 12th amino acid to the 77th amino acid of SEQ ID NO: 1; and (c5) the sequence from the $12^{th}$ amino acid to the $77^{th}$ amino acid of SEQ ID NO: 63.

In a particular embodiment, the CXCR3 ligand provided herein is any of a CXCL10 variant, a CXCL11 variant, a CXCL9 variant, an hITIP variant, and a chimeric protein prepared from those variants.

In a particular embodiment, the CXCR3 ligand provided herein is any of the following sequences (d1) to (d7):

(d1) a sequence shown by any one of SEQ ID NOs: 2 to 57, 92 to 147, and 149 to 204;

(d2) a sequence showing 90% or more sequence identity to SEQ ID NO: 60;

(d3) a sequence showing 90% or more sequence identity to SEQ ID NO: 61;

(d4) a sequence showing 90% or more sequence identity to SEQ ID NO: 62;

(d5) a sequence showing 90% or more sequence identity to SEQ ID NO: 63;

(d6) a sequence showing 90% or more sequence identity to SEQ ID NO: 1; and (d7) a sequence comprising 10 or less amino acid substitutions, insertions, or deletions to a sequence selected from SEQ ID NOs: 1 to 57, 60 to 63, 92 to 147, and 149 to 204;

In a particular embodiment, the CXCR3 ligand provide herein is a sequence showing 90% or more sequence identity, 95% or more sequence identity, 96% or more sequence identity, 97% or more sequence identity, 98% or more sequence identity, or 99% or more sequence identity to any one of the sequences of SEQ ID NOs: 1 and 60 to 63.

CXCR3 Ligand Mutants

In certain embodiments, amino acid sequence mutants of the CXCR3 ligands provided herein are contemplated. Amino acid sequence mutants of a CXCR3 ligand may be prepared by introducing appropriate modifications into the nucleotide sequence encoding the CXCR3 ligand, or by peptide synthesis. Such modifications include, for example, deletions from, and/or insertions into and/or substitutions of residues within the amino acid sequences of the CXCR3 ligand. Any combination of deletion, insertion, and substitution can be made to arrive at the final construct, provided that the final construct possesses the desired characteristics (e.g., resistance to DPPIV or activity to cause migration of CXCR3-expressing cells).

Substitution, Insertion, and Deletion Mutants

In certain embodiments, CXCR3 ligand mutants having one or more amino acid substitutions are provided. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into a CXCR3 ligand of interest and the products screened for a desired activity, e.g., retained/improved resistance to DPPIV or activity to cause migration of CXCR3-expressing cells.

TABLE 1

| Original residue | Exemplary substitutions | Preferred substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine ; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

In a particular embodiment, one or more modifications may be carried out regarding the substitutions, insertions, or deletions as long as such modifications do not substantially reduce the abilities of the CXCR3 ligand. In a particular embodiment, the CXCR ligand mutant described above comprises one, two, three, four, five, six, seven, eight, nine, or ten amino acid modifications.

Amino Acid Sequence Identity

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Methods of Conferring Resistance to DPPIV on CXCR3 Ligands

The present disclosure also relates to methods of conferring resistance to DPPIV on a CXCR3 ligand.

In a particular embodiment, the method of conferring resistance to DPPIV on a CXCR3 ligand provided herein comprises modifying the sequence in the vicinity of the N-terminus of a parent CXCR3 ligand.

In a particular embodiment, the $2^{nd}$ amino acid from the N-terminus of the parent CXCR3 ligand used in the method of conferring resistance to DPPIV on a CXCR3 ligand provided herein is P or A. In a particular embodiment, the $1^{st}$ amino acid from the N-terminus of the parent CXCR3 ligand used in the method of conferring resistance to DPPIV on a CXCR3 ligand provided herein is V. In a more specific embodiment, the N-terminal sequence of the parent CXCR3 ligand used in the method of conferring resistance to DPPIV on a CXCR3 ligand provided herein is V-P-L or V-A-L. In a more specific embodiment, the N-terminal sequence of the parent CXCR3 ligand used in the method of conferring resistance to DPPIV on a CXCR3 ligand provided herein is V-P-L-S-R-T-V-R (SEQ ID NO: 86) or V-A-L-S-R-T-V-R (SEQ ID NO: 87).

In a particular embodiment, the $2^{nd}$ amino acid from the N-terminus of the parent CXCR3 ligand used in the method of conferring resistance to DPPIV on a CXCR3 ligand provided herein is P. In a particular embodiment, the $1^{st}$ amino acid from the N-terminus of the parent CXCR3 ligand used in the method of conferring resistance to DPPIV on a CXCR3 ligand provided herein is F. In a more specific embodiment, the N-terminal sequence of the parent CXCR3 ligand used in the method of conferring resistance to DPPIV on a CXCR3 ligand provided herein is F-P-M. In a more specific embodiment, the N-terminal sequence of the parent CXCR3 ligand used in the method of conferring resistance to DPPIV on a CXCR3 ligand provided herein is F-P-M-F-K-R-G-R (SEQ ID NO: 91).

In a particular embodiment, the parent CXCR3 ligand used in the method of conferring resistance to DPPIV on a CXCR3 ligand provided herein has a C-X-C motif. The two cysteines contained in the C-X-C motif can each form disulfide bonds with cysteines other than those of the C-X-C motif comprised in the parent CXCR3 ligand. The C-X-C motif in the parent CXCR3 ligand can be selected from C-T-C(Cys-Thr-Cys), C-L-C (Cys-Leu-Cys), and C-S-C (Cys-Ser-Cys). In a specific embodiment, the C-X-C motif in the parent CXCR3 ligand can be located next to the C-terminus of the N-terminal sequence V-P-L-S-R-T-V-R (SEQ ID NO: 86) or V-A-L-S-R-T-V-R (SEQ ID NO: 87) or F-P-M-F-K-R-G-R (SEQ ID NO: 91).

In a particular embodiment, the parent CXCR3 ligand used in the method of conferring resistance to DPPIV on a CXCR3 ligand provided herein can further have any of the following (c1) to (c5) at the C-terminus of the C-X-C motif:

(c1) the sequence from the $12^{th}$ amino acid to the $77^{th}$ amino acid of SEQ ID NO: 60;

(c2) the sequence from the $12^{th}$ amino acid to the $73^{rd}$ amino acid of SEQ ID NO: 61;

(c3) the sequence from the $12^{th}$ amino acid to the $103^{rd}$ amino acid of SEQ ID NO: 62;

(c4) the sequence from the $12^{th}$ amino acid to the $77^{th}$ amino acid of SEQ ID NO: 1; and (c5) the sequence from the $12^{th}$ amino acid to the $77^{th}$ amino acid of SEQ ID NO: 63.

In a particular embodiment, the parent CXCR3 ligand used in the method of conferring resistance to DPPIV to a CXCR3 ligand provided herein is selected from a naturally-occurring CXCL10, naturally-occurring CXCL11, naturally-occurring CXCL9, CXCL10 variant, CXCL11 variant, CXCL9 variant, and chimeric proteins prepared from them.

In a particular embodiment, the method of conferring resistance to DPPIV on a CXCR3 ligand provided herein includes any of the following:

(1) substituting the $2^{nd}$ amino acid from the N-terminus of the parent CXCR3 ligand from P or A to F, G, I, K, L, M, T, V, W, or Y;

(2) further adding A, F, G, H, I, K, L, M, N, P, Q, R, S, T, V, W, or Y to the N-terminus of the parent CXCR3 ligand;

(3) inserting A, F, G, H, I, K, L, M, P, Q, R, S, T, V, W, or Y between the $1^{st}$ and $2^{nd}$ amino acids at the N-terminus of the parent CXCR3 ligand; and (4) deleting the V at the N-terminus of the parent CXCR3 ligand.

In other words, the present specification provides the use of any of the following for conferring resistance to DPPIV on a CXCR3 ligand:

(1) substituting the $2^{nd}$ amino acid from the N-terminus of the parent CXCR3 ligand from P or A to F, G, I, K, L, M, T, V, W, or Y;

(2) further adding A, F, G, H, I, K, L, M, N, P, Q, R, S, T, V, W, or Y to the N-terminus of the parent CXCR3 ligand;

(3) inserting A, F, G, H, I, K, L, M, P, Q, R, S, T, V, W, or Y between the $1^{st}$ and $2^{nd}$ amino acids at the N-terminus of the parent CXCR3 ligand; and (4) deleting the V at the N-terminus of the parent CXCR3 ligand.

In a particular embodiment, the method of conferring resistance to DPPIV on a CXCR3 ligand provided herein includes any of the following:

(1) substituting the $2^{nd}$ amino acid from the N-terminus of the parent CXCR3 ligand from P or A to F, G, I, L, M, T, V, W, or Y;

(2) further adding A, G, I, L, N, Q, S, T, or W to the N-terminus of the parent CXCR3 ligand;

(3) inserting A, F, G, I, M, P, T, or V between the $1^{st}$ and $2^{nd}$ amino acids at the N-terminus of the parent CXCR3 ligand; and (4) deleting the V at the N-terminus of the parent CXCR3 ligand.

In other words, the present specification provides the use of any of the following for conferring resistance to DPPIV on a CXCR3 ligand:

(1) substituting the 2nd amino acid from the N-terminus of the parent CXCR3 ligand from P or A to F, G, I, L, M, T, V, W, or Y;

(2) further adding A, G, I, L, N, Q, S, T, or W to the N-terminus of the parent CXCR3 ligand;

(3) inserting A, F, G, I, M, P, T, or V between the 1st and 2nd amino acids at the N-terminus of the parent CXCR3 ligand; and (4) deleting the V at the N-terminus of the parent CXCR3 ligand.

In a particular embodiment, the method of conferring resistance to DPPIV on a CXCR3 ligand provided herein includes any of the following:

(1) further adding A, D, E, F, G, H, I, K, L, M, N, P, Q, S, T, V, W, or Y to the N-terminus of the parent CXCR3 ligand;

(2) substituting the $2^{nd}$ amino acid from the N-terminus of the parent CXCR3 ligand from P to A, D, E, G, H, I, M, N, Q, R, S, T, V, W, or Y; and (3) inserting A, D, E, F, G, H, L, M, N, P, Q, S, T, W, or Y between the $1^{st}$ and $2^{nd}$ amino acids at the N-terminus of the parent CXCR3 ligand.

In other words, the present specification provides the use of any of the following for conferring resistance to DPPIV on a CXCR3 ligand:

(1) further adding A, D, E, F, G, H, I, K, L, M, N, P, Q, S, T, V, W, or Y to the N-terminus of the parent CXCR3 ligand;

(2) substituting the $2^{nd}$ amino acid from the N-terminus of the parent CXCR3 ligand from P to A, D, E, G, H, I, M, N, Q, R, S, T, V, W, or Y; and (3) inserting A, D, E, F, G, H, L, M, N, P, Q, S, T, W, or Y between the $1^{st}$ and $2^{nd}$ amino acids at the N-terminus of the parent CXCR3 ligand.

In a particular embodiment, the method of conferring resistance to DPPIV on a CXCR3 ligand provided herein comprises further adding A, D, E, G, M, N, Q, S, T, V, or Y to the N-terminus of the parent CXCR3 ligand.

In other words, the present specification provides the use of further adding A, D, E, G, M, N, Q, S, T, V, or Y to the N-terminus of the parent CXCR3 ligand for conferring resistance to DPPIV on a CXCR3 ligand.

Fusion Proteins Comprising a CXCR3 Ligand

One aspect of the disclosure relates to fusion proteins comprising a CXCR3 ligand. In a specific embodiment, the fusion proteins of the present disclosure relate to fusion proteins comprising a CXCR3 ligand at the N-terminus. The fusion proteins of the present disclosure may be fusion proteins in which a CXCR3 ligand and an antibody are fused, or may be fusion proteins in which a CXCR3 ligand and an antibody Fc region or another type of protein such as albumin are fused. A specific example includes a fusion protein in which an antibody (including the full-length antibody and antibody fragments), an antibody Fc region, or another type of protein such as albumin is fused to the C-terminus of a CXCR3 ligand. A fusion protein comprising a CXCR3 ligand can be purified using a substance that binds to the fusion protein. For example, when fused with an antibody Fc region, adsorption onto immobilized protein A can be used to recover the CXCR3 ligand.

In the fusion proteins of the present disclosure, the CXCR3 ligand and the fusion partner can be fused via a linker. For example, an arbitrary peptide linker that can be introduced by genetic engineering, or a linker disclosed as a synthetic compound linker (see e.g., Protein Engineering, 9 (3), 299-305, 1996) can be used as the linker used in the fusion of the CXCR3 ligand with the fusion partner.

The length of the peptide linker is not particularly limited and may be appropriately selected by those skilled in the art according to the purpose. Examples of the peptide linker can include, but are not limited to:

```
Ser

Gly•Ser (GS)

Ser•Gly (SG)

Gly•Gly•Ser (GGS)

Gly•Ser•Gly (GSG)

Ser•Gly•Gly (SGG)

Gly•Ser•Ser (GSS)

Ser•Ser•Gly (SSG)

Ser•Gly•Ser (SGS)

(GGGS, SEQ ID NO: 64)
Gly•Gly•Gly•Ser (GGSG, SEQ ID NO: 65)
Gly•Gly•Ser•Gly (GSGG, SEQ ID NO: 66)
Gly•Ser•Gly•Gly (SGGG, SEQ ID NO: 67)
Ser•Gly•Gly•Gly (GSSG, SEQ ID NO: 68)
Gly•Ser•Ser•Gly (GGGGS, SEQ ID NO: 69)
Gly•Gly•Gly•Gly•Ser (GGGSG, SEQ ID NO: 70)
Gly•Gly•Gly•Ser•Gly (GGSGG, SEQ ID NO: 71)
Gly•Gly•Ser•Gly•Gly (GSGGG, SEQ ID NO: 72)
Gly•Ser•Gly•Gly•Gly (GSGGS, SEQ ID NO: 73)
Gly•Ser•Gly•Gly•Ser (SGGGG, SEQ ID NO: 74)
Ser•Gly•Gly•Gly•Gly (GSSGG, SEQ ID NO: 75)
Gly•Ser•Ser•Gly•Gly (GSGSG, SEQ ID NO: 76)
Gly•Ser•Gly•Ser•Gly (SGGSG, SEQ ID NO: 77)
Ser•Gly•Gly•Ser•Gly (GSSSG, SEQ ID NO: 78)
Gly•Ser•Ser•Ser•Gly (GGGGGS, SEQ ID NO: 79)
Gly•Gly•Gly•Gly•Gly•Ser (SGGGGG, SEQ ID NO: 80)
Ser•Gly•Gly•Gly•Gly•Gly
```

```
-continued
                                 (GGGGGGS, SEQ ID NO: 81)
Gly•Gly•Gly•Gly•Gly•Gly•Ser (SGGGGGG, SEQ ID NO: 82)
Ser•Gly•Gly•Gly•Gly•Gly•Gly (Gly•Gly•Gly•Gly•Ser (GGGGS, SEQ ID NO: 69))n (Ser•Gly•Gly•Gly•Gly (SGGGG, SEQ ID NO: 74))n
``` wherein n is an integer of 1 or larger. However, the length and sequence of the peptide linker can be appropriately selected by those skilled in the art according to the purpose.

The synthetic compound linker (chemical cross-linking agent) is a cross-linking agent usually used in peptide cross-linking, for example, N-hydroxysuccinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis (sulfosuccinimidyl succinate) (sulfo-EGS), disuccinimidyl tartrate (DST), disulfosuccinimidyl tartrate (sulfo-DST), bis [2-(succinimidoxycarbonyloxy)ethyl]sulfone (BSOCOES), or bis[2-(sulfosuccinimidoxycarbonyloxy)ethyl]sulfone (sulfo-BSOCOES).

These cross-linking agents are commercially available.

Antibodies

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody Fragments

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

Fc Regions

The term "Fc region" herein is used to define a C-terminal region of an immunoglobulin heavy chain that contains at least a portion of the constant region. The term includes native sequence Fc regions and mutant Fc regions. In one embodiment, a human IgG heavy chain Fc region extends from Cys226, or from Pro230, to the carboxyl-terminus of the heavy chain. However, the C-terminal lysine (Lys447) or glycine-lysine (Gly446-Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. In the present invention, the Fc region can include various modifications. For example, modifications for increasing the yield of molecules in which Fc is heteroassociated and modifications for suppressing binding to FcγR are known.

Nucleic Acids/Polynucleotides

An "isolated" nucleic acid/polynucleotide refers to a nucleic acid/polynucleotide molecule that has been separated from a component of its natural environment. An isolated nucleic acid/polynucleotide includes a nucleic acid/polynucleotide molecule contained in cells that ordinarily contain the nucleic acid/polynucleotide molecule, but the nucleic acid/polynucleotide molecule is present extrachromosomally or at a chromosomal location that is different from its natural chromosomal location.

The present disclosure also relates to a nucleic acid/polynucleotide that encodes a CXCR3 ligand, or a nucleic acid/polynucleotide that encodes a fusion protein comprising the CXCR3 ligand.

"Isolated nucleic acid/polynucleotide encoding a CXCR3 ligand" refers to one or more nucleic acid molecules encoding a CXCR3 ligand, including such nucleic acid molecule(s) in a single vector or separate vectors, and such nucleic acid molecule(s) present at one or more locations in a host cell.

Vectors

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Host Cells

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The present disclosure also relates to host cells comprising a nucleic acid/polynucleotide encoding a CXCR3 ligand or a nucleic acid/polynucleotide encoding a fusion protein comprising the CXCR3 ligand.

Methods for Producing a CXCR3 Ligand

The polynucleotide according to the present disclosure is usually carried by (or inserted in) an appropriate vector and transfected into host cells. The vector is not particularly limited as long as the vector can stably retain an inserted nucleic acid. For example, when E. coli is used as the host, a pBluescript vector (manufactured by Stratagene Corp.) or the like is preferred as a vector for cloning, although various commercially available vectors can be used.

In the case of using a vector for the purpose of producing a CXCR3 ligand or a fusion protein comprising a CXCR3 ligand of the present disclosure, an expression vector is particularly useful. The expression vector is not particularly limited as long as the vector permits expression of the ligand-binding molecule in vitro, in E. coli, in cultured cells, or in individual organisms. The expression vector is preferably, for example, a pBEST vector (manufactured by Promega Corp.) for in vitro expression, a pET vector (manufactured by Invitrogen Corp.) for expression in E. coli, a pME18S-FL3 vector (GenBank Accession No. AB009864) for expression in cultured cells, and a pME18S vector (Mol Cell Biol. 8: 466-472 (1988)) for expression in individual organisms. The insertion of the DNA of the present disclosure into the vector can be performed by a routine method, for example, ligase reaction using restriction sites (Current protocols in Molecular Biology edit. Ausubel et al. (1987) Publish. John Wiley & Sons. Section 11.4-11.11).

The host cells are not particularly limited, and various host cells are used according to the purpose. Examples of the cells for expressing the CXCR3 ligand or the fusion protein may include bacterial cells (e.g., Streptococcus, Staphylococcus, E. coli, Streptomyces, and Bacillus subtilis), fungal cells (e.g., yeasts and Aspergillus), insect cells (e.g., Drosophila S2 and Spodoptera SF9), animal cells (e.g., CHO, COS, HeLa, C127, 3T3, BHK, HEK293, and Bowes melanoma cells) and plant cells. The transfection of the vector to the host cells may be performed by a method known in the art, for example, a calcium phosphate precipitation method, an electroporation method (Current protocols in Molecular Biology edit. Ausubel et al., (1987) Publish. John Wiley & Sons. Section 9.1-9.9), a Lipofectamine method (manufactured by GIBCO-BRL), or a microinjection method.

An appropriate secretory signal can be incorporated into the ligand-binding molecule or the fusion protein of interest, in order to secrete the CXCR3 ligand or the fusion protein expressed in the host cells to the endoplasmic reticulum lumen, periplasmic space, or an extracellular environment. The signal may be endogenous to the ligand-binding molecule or the fusion protein of interest, or may be a foreign signal. Specifically, for example, the signal sequence MNQ-TAILICCLIFLTLSGIQG (SEQ ID NO: 83), MKKSGVLFLLGIILLVLIGVQG (SEQ ID NO: 84), MSVKGMAIALAVILCATVVQG (SEQ ID NO: 85), or MGWSCIILFLVATATGVHS (SEQ ID NO: 148) can be used.

When the CXCR3 ligand or the fusion protein of the present disclosure is secreted into a medium, the recovery of the CXCR3 ligand or the fusion protein in the above production method is performed by collecting the medium. When the CXCR3 ligand or the fusion protein of the present disclosure is produced in cells, the cells are first lysed and the CXCR3 ligand or the fusion protein is subsequently recovered.

A method known in the art including ammonium sulfate or ethanol precipitation, acid extraction, anion- or cation-exchange chromatography, phosphocellulose chromatography, hydrophobic i'nteraction chromatography, affinity chromatography, hydroxylapatite chromatography, and lectin chromatography can be used for recovering and purifying the CXCR3 ligand or the fusion protein of the present disclosure from the recombinant cell cultures.

The CXCR3 ligands provided herein can also be produced by conferring resistance to DPPIV on a parent CXCR3 ligand. In a particular embodiment, the method of producing a CXCR3 ligand provided herein comprises modifying the sequence near the N-terminus of a parent CXCR3 ligand.

In a particular embodiment, the 2$^{nd}$ amino acid from the N-terminus of a parent CXCR3 ligand used in a method of producing a CXCR3 ligand provided herein is P or A. In a particular embodiment, the 1$^{st}$ amino acid from the N-terminus of a parent CXCR3 ligand used in a method of producing a CXCR3 ligand provided herein is V. In a more specific embodiment, the N-terminal sequence of a parent CXCR3 ligand used in a method of producing a CXCR3 ligand provided herein is V-P-L or V-A-L. In a more specific embodiment, the N-terminal sequence of a parent CXCR3 ligand used in a method of producing a CXCR3 ligand provided herein is V-P-L-S-R-T-V-R (SEQ ID NO: 86) or V-A-L-S-R-T-V-R (SEQ ID NO: 87).

In a particular embodiment, the 2$^{nd}$ amino acid from the N-terminus of a parent CXCR3 ligand used in a method of producing a CXCR3 ligand provided herein is P. In a particular embodiment, the 1$^{st}$ amino acid from the N-terminus of a parent CXCR3 ligand used in a method of producing a CXCR3 ligand provided herein is F. In a more specific embodiment, the N-terminal sequence of a parent CXCR3 ligand used in a method of producing a CXCR3 ligand provided herein is F-P-M. In a more specific embodiment, the N-terminal sequence of a parent CXCR3 ligand used in a method of producing a CXCR3 ligand provided herein is F-P-M-F-K-R-G-R (SEQ ID NO: 91).

In a particular embodiment, the parent CXCR3 ligand used in a method of producing a CXCR3 ligand provided herein has a C-X-C motif. The two cysteines contained in the C-X-C motif can each form disulfide bonds with cysteines other than those of the C-X-C motif comprised in the parent CXCR3 ligand. The C-X-C motif in the parent CXCR3 ligand can be selected from C-T-C(Cys-Thr-Cys), C-L-C (Cys-Leu-Cys), and C-S-C(Cys-Ser-Cys). In a specific embodiment, the CXC motif in the parent CXCR3 ligand can be located next to the C-terminus of the N-terminal sequence V-P-L-S-R-T-V-R (SEQ ID NO: 86) or V-A-L-S-R-T-V-R (SEQ ID NO: 87) or F-P-M-F-K-R-G-R (SEQ ID NO: 91).

In a particular embodiment, the parent CXCR3 ligand used in a method of producing a CXCR3 ligand provided herein may further have at the C-terminus of the C-X-C motif any of the following sequences (c1) to (c5):

(c1) the sequence from the $12^{th}$ amino acid to the $77^{th}$ amino acid of SEQ ID NO: 60;

(c2) the sequence from the $12^{th}$ amino acid to the $73^{rd}$ amino acid of SEQ ID NO: 61;

(c3) the sequence from the $12^{th}$ amino acid to the $103^{rd}$ amino acid of SEQ ID NO: 62;

(c4) the sequence from the $12^{th}$ amino acid to the $77^{th}$ amino acid of SEQ ID NO: 1; and (c5) the sequence from the $12^{th}$ amino acid to the $77^{th}$ amino acid of SEQ ID NO: 63.

In a particular embodiment, the parent CXCR3 ligand used in a method of producing a CXCR3 ligand provided herein is selected from a naturally-occurring CXCL10, naturally-occurring CXCL11, naturally-occurring CXCL9, CXCL10 variant, CXCL11 variant, CXCL9 variant, and chimeric proteins prepared from them.

In a particular embodiment, the method of producing a CXCR3 ligand provided herein includes any of the following:

1) substituting the 2nd amino acid from the N-terminus of the parent CXCR3 ligand from P or A to F, G, I, K, L, M, T, V, W, or Y;

2) further adding A, F, G, H, I, K, L, M, N, P, Q, R, S, T, V, W, or Y to the N-terminus of the parent CXCR3 ligand;

3) inserting A, F, G, H, I, K, L, M, P, Q, R, S, T, V, W, or Y between the 1st and 2nd amino acids at the N-terminus of the parent CXCR3 ligand; and 4) deleting the V at the N-terminus of the parent CXCR3 ligand.

In a particular embodiment, the method of producing a CXCR3 ligand provided herein includes any of the following:

(1) substituting the 2nd amino acid from the N-terminus of the parent CXCR3 ligand from P or A to F, G, I, L, M, T, V, W, or Y;

(2) further adding A, G, I, L, N, Q, S, T, or W to the N-terminus of the parent CXCR3 ligand;

(3) inserting A, F, G, I, M, P, T, or V between the $1^{st}$ and 2nd amino acids at the N-terminus of the parent CXCR3 ligand; and (4) deleting the V at the N-terminus of the parent CXCR3 ligand.

In a particular embodiment, the method of producing a CXCR3 ligand provided herein includes any of the following:

(1) further adding A, D, E, F, G, H, I, K, L, M, N, P, Q, S, T, V, W, or Y to the N-terminus of the parent CXCR3 ligand;

(2) substituting the $2^{nd}$ amino acid from the N-terminus of the parent CXCR3 ligand from P to A, D, E, G, H, I, M, N, Q, R, S, T, V, W, or Y; and (3) inserting A, D, E, F, G, H, L, M, N, P, Q, S, T, W, or Y between the $1^{st}$ and $2^{nd}$ amino acids at the N-terminus of the parent CXCR3 ligand.

In a particular embodiment, the method of producing a CXCR3 ligand provided herein includes further adding A, D, E, G, M, N, Q, S, T, V, or Y to the N-terminus of the parent CXCR3 ligand.

The methods of producing a CXCR3 ligand provided herein may further additionally include, in a specific embodiment, a step of recovering or isolating the CXCR3 ligand containing the above-mentioned modifications.

Treatments

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the CXCR3 ligands of the present disclosure are used to delay development of a disease or to slow the progression of a disease.

Pharmaceutical Compositions

The terms "pharmaceutical formulation" or "pharmaceutical composition" refer to a preparation which is in such form as to permit the biological activity of an active ingredient contained therein to be effective, and which contains no additional components which are unacceptably toxic to a subject to which the formulation would be administered.

Pharmaceutically Acceptable Carriers

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Pharmaceutical Compositions Comprising a CXCR3 Ligand or a Fusion Protein Comprising a CXCR3 Ligand The present disclosure also relates to pharmaceutical compositions (agents) comprising a CXCR3 ligand of the present disclosure and a pharmaceutically acceptable carrier, and pharmaceutical compositions (agents) comprising a fusion protein comprising a CXCR3 ligand of the present disclosure and a pharmaceutically acceptable carrier.

In the present disclosure, the term "pharmaceutical composition comprising a CXCR3 ligand" may be used interchangeably with a "method for treating a disease, comprising administering a CXCR3 ligand to a subject to be treated" and may be used interchangeably with "use of a CXCR3 ligand for the manufacture of a medicament for treating a disease". Also, the term "pharmaceutical composition comprising a CXCR3 ligand" may be used interchangeably with "use of a CXCR3 ligand for treating a disease". The term "pharmaceutical composition comprising a fusion protein comprising a CXCR3 ligand" may be used interchangeably with a "method for treating a disease, comprising administering a fusion protein comprising a CXCR3 ligand to a subject to be treated" and may be used interchangeably with "use of a fusion protein comprising a CXCR3 ligand for the manufacture of a medicament for treating a disease". Also, the term "pharmaceutical composition comprising a fusion protein comprising a CXCR3 ligand" may be used interchangeably with "use of a fusion protein comprising a CXCR3 ligand for treating a disease".

In some embodiments of the present disclosure, a composition comprising a CXCR3 ligand can be administered to an individual. In some embodiments of the present disclosure, a fusion protein comprising a CXCR3 ligand can be administered to an individual.

The pharmaceutical composition of the present disclosure can be formulated by use of a method known to those skilled in the art. For example, the pharmaceutical composition can be parenterally used in a form of an injection of a sterile solution or suspension with water or any other pharmaceutically acceptable liquids. The pharmaceutical composition can be formulated, for example, by appropriately combining with a pharmacologically acceptable carrier or medium, specifically, sterile water or physiological saline, a vegetable oil, an emulsifier, a suspending agent, a surfactant, a stabilizer, a flavoring agent, an excipient, a vehicle, an antiseptic, a binder, etc. and mixing them into a unit dosage form required for generally accepted pharmaceutical practice. The amount of the active ingredient in these formulations is set so as to give an appropriate volume in a prescribed range.

A sterile composition for injection can be formulated according to usual pharmaceutical practice using a vehicle such as injectable distilled water. Examples of the injectable aqueous solution include isotonic solutions containing physiological saline, glucose, or other adjuvants (e.g., D-sorbitol, D-mannose, D-mannitol, and sodium chloride). The aqueous solution can be used in combination with an appropriate solubilizer, for example, an alcohol (ethanol, etc.), a polyalcohol (propylene glycol, polyethylene glycol, etc.), or a nonionic surfactant (Polysorbate 80™, HCO-50, etc.).

Examples of the oily liquid include sesame oil and soybean oil, and benzyl benzoate and/or benzyl alcohol can be used in combination as a solubilizer. The oily liquid can be combined with a buffer (e.g., a phosphate buffer solution and a sodium acetate buffer solution), a soothing agent (e.g., procaine hydrochloride), a stabilizer (e.g., benzyl alcohol and phenol), or an antioxidant. The prepared injection solution is usually filled into an appropriate ampule.

The pharmaceutical composition of the present disclosure is preferably administered through a parenteral route. For example, a composition for injection, transnasal administration, transpulmonary administration, or percutaneous administration is administered. The pharmaceutical composition can be administered systemically or locally by, for example, intravenous injection, intramuscular injection, intraperitoneal injection, or subcutaneous injection.

The administration method can be appropriately selected according to the age and symptoms of a patient. The dose of the pharmaceutical composition containing the CXCR3 ligand can be determined to the range of, for example, 0.0001 mg to 1000 mg per kg body weight per dose. Alternatively, the dose can be determined to, for example, 0.001 mg to 100000 mg per patient. However, the present disclosure is not necessarily limited by these numerical values. The dose and the administration method vary depending on the body weight, age, symptoms, and such of a patient, and those skilled in the art can determine an appropriate dose and administration method in consideration of these conditions.

EXAMPLES

The following are examples of methods and compositions of the present disclosure. It is understood that various other embodiments may be practiced, given the general description provided above.

Figure 1B:
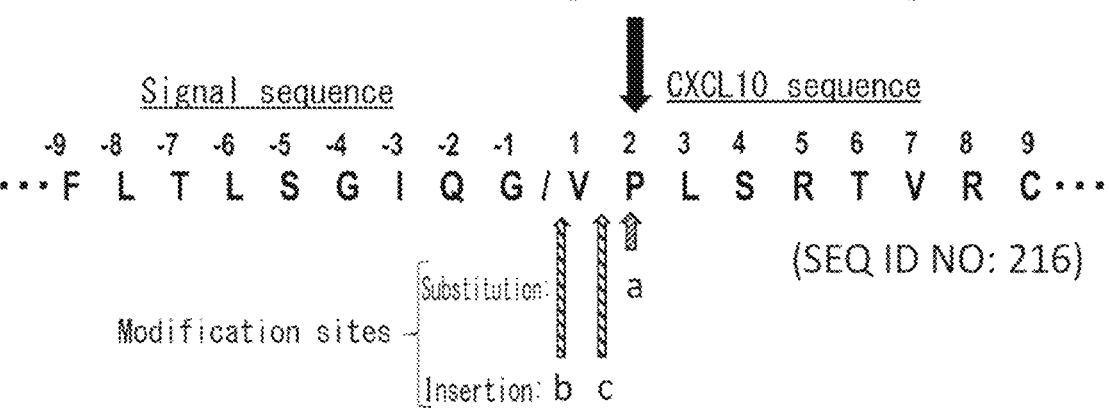
FIG. 1B shows the positions of the amino acid modifications in and around the DPPIV recognition/cleavage site on the sequence FLTLSGIQGVPLSRTVRC (SEQ ID NO: 216) for producing hCXCL10 variants.

Example 1. Construction of Human CXCL10 (hCXCL10) Variants and hCXCL10 Variant Fc Fusions An hCXCL10 variant hCXCL10R75A (SEQ ID NO: 1) in which human CXCL10 (hCXCL10, Refseq: NP_001556.2, Uniprot ID: P02778) has been mutated to be resistant to furin protease, and human CXCL10 variants in which amino acid modifications have been introduced into and around the dipeptidyl peptidase IV (DPPIV) recognition/cleavage site of hCXCL10R75A were prepared. FIG. 1B shows the amino acid modification positions in and around the DPPIV recognition/cleavage site, and Table 2 (Table 2-1 and Table 2-2) shows the names, sequences, and such of the designed human CXCL10 variants.

TABLE 2

| Sequence Name | SEQ ID NO | Modification pattern | Modified, inserted amino acid residue | Modification | N-terminal sequence | Corresponding hCXCL10 variant Fc fusion |
|---|---|---|---|---|---|---|
| hCXCL10R75A | 1 | | | | VPLS (SEQ ID NO: 218) . . . | hCXCL10R75A-G1T4k.one//VHn-G1T4h.one.H435R |
| hCXCL10R75A.0001 | 2 | a | A | P2A | VALS (SEQ ID NO: 219) . . . | hCXCL10R75A.0001-G1T4k.one//VHn-G1T4h.one.H435R |
| hCXCL10R75A.0002 | 3 | a | D | P2D | VDLS (SEQ ID NO: 220) . . . | hCXCL10R75A.0002-G1T4k.one//VHn-G1T4h.one.H435R |
| hCXCL10R75A.0003 | 4 | a | E | P2E | VELS (SEQ ID NO: 221) . . . | hCXCL10R75A.0003-G1T4k.one//VHn-G1T4h.one.H435R |
| hCXCL10R75A.0004 | 5 | a | F | P2F | VFLS (SEQ ID NO: 222) . . . | hCXCL10R75A.0004-G1T4k.one//VHn-G1T4h.one.H435R |
| hCXCL10R75A.0005 | 6 | a | G | P2G | VGLS (SEQ ID NO: 223) . . . | hCXCL10R75A.0005-G1T4k.one//VHn-G1T4h.one.H435R |
| hCXCL10R75A.0006 | 7 | a | H | P2H | VHLS (SEQ ID NO: 224) . . . | hCXCL10R75A.0006-G1T4k.one//VHn-G1T4h.one.H435R |
| hCXCL10R75A.0007 | 8 | a | I | P2I | VILS (SEQ ID NO: 225) . . . | hCXCL10R75A.0007-G1T4k.one//VHn-G1T4h.one.H435R |
| hCXCL10R75A.0008 | 9 | a | K | P2K | VKLS (SEQ ID NO: 226) . . . | hCXCL10R75A.0008-G1T4k.one//VHn-G1T4h.one.H435R |
| hCXCL10R75A.0009 | 10 | a | L | P2L | VLLS (SEQ ID NO: 227) . . . | hCXCL10R75A.0009-G1T4k.one//VHn-G1T4h.one.H435R |
| hCXCL10R75A.0010 | 11 | a | M | P2M | VMLS (SEQ ID NO: 228) . . . | hCXCL10R75A.0010-G1T4k.one//VHn-G1T4h.one.H435R |

TABLE 2-continued

| Sequence Name | SEQ ID NO | Modification pattern | Modified, inserted amino acid residue | Modification | N-terminal sequence | Corresponding hCXCL10 variant Fc fusion |
|---|---|---|---|---|---|---|
| hCXCL10R75A.0011 | 12 | a | N | P2N | VNLS (SEQ ID NO: 229) . . . | hCXCL10R75A.0011-G1T4k.one//VHn-G1T4h.one.H435R |
| hCXCL10R75A.0012 | 13 | a | Q | P2Q | VQLS (SEQ ID NO: 230) . . . | hCXCL10R75A.0012-G1T4k.one//VHn-G1T4h.one.H435R |
| hCXCL10R75A.0013 | 14 | a | R | P2R | VRLS (SEQ ID NO: 231) . . . | hCXCL10R75A.0013-G1T4k.one//VHn-G1T4h.one.H435R |
| hCXCL10R75A.0014 | 15 | a | S | P2S | VSLS (SEQ ID NO: 232) . . . | hCXCL10R75A.0014-G1T4k.one//VHn-G1T4h.one.H435R |
| hCXCL10R75A.0015 | 16 | a | T | P2T | VTLS (SEQ ID NO: 233) . . . | hCXCL10R75A.0015-G1T4k.one//VHn-G1T4h.one.H435R |
| hCXCL10R75A.0016 | 17 | a | V | P2V | VVLS (SEQ ID NO: 234) . . . | hCXCL10R75A.0016-G1T4k.one//VHn-G1T4h.one.H435R |
| hCXCL10R75A.0017 | 18 | a | W | P2W | VWLS (SEQ ID NO: 235) . . . | hCXCL10R75A.0017-G1T4k.one//VHn-G1T4h.one.H435R |
| hCXCL10R75A.0018 | 19 | a | Y | P2Y | VYLS (SEQ ID NO: 236) . . . | hCXCL10R75A.0018-G1T4k.one//VHn-G1T4h.one.H435R |
| hCXCL10R75A.0019 | 20 | b | A | G-1_V1insA | AVPL (SEQ ID NO: 237) . . . | hCXCL10R75A.0019-G1T4k.one//VHn-G1T4h.one.H435R |
| hCXCL10R75A.0020 | 21 | b | D | G-1_V1insD | DVPL (SEQ ID NO: 238) . . . | hCXCL10R75A.0020-G1T4k.one//VHn-G1T4h.one.H435R |
| hCXCL10R75A.0021 | 22 | b | E | G-1_V1insE | EVPL (SEQ ID NO: 239) . . . | hCXCL10R75A.0021-G1T4k.one//VHn-G1T4h.one.H435R |
| hCXCL10R75A.0022 | 23 | b | F | G-1_V1insF | FVPL (SEQ ID NO: 240) . . . | hCXCL10R75A.0022-G1T4k.one//VHn-G1T4h.one.H435R |
| hCXCL10R75A.0023 | 24 | b | G | G-1_V1insG | GVPL (SEQ ID NO: 241) . . . | hCXCL10R75A.0023-G1T4k.one//VHn-G1T4h.one.H435R |
| hCXCL10R75A.0024 | 25 | b | H | G-1_V1insH | HVPL (SEQ ID NO: 242) . . . | hCXCL10R75A.0024-G1T4k.one//VHn-G1T4h.one.H435R |
| hCXCL10R75A.0025 | 26 | b | I | G-1_V1insI | IVPL (SEQ ID NO: 243) . . . | hCXCL10R75A.0025-G1T4k.one//VHn-G1T4h.one.H435R |
| hCXCL10R75A.0026 | 27 | b | K | G-1_V1insK | KVPL (SEQ ID NO: 244) . . . | hCXCL10R75A.0026-G1T4k.one//VHn-G1T4h.one.H435R |
| hCXCL10R75A.0027 | 28 | b | L | G-1_V1insL | LVPL (SEQ ID NO: 245) . . . | hCXCL10R75A.0027-G1T4k.one//VHn-G1T4h.one.H435R |
| hCXCL10R75A.0028 | 29 | b | M | G-1_V1insM | MVPL (SEQ ID NO: 246) | hCXCL10R75A.0028-G1T4k.one//VHn-G1T4h.one.H435R |
| hCXCL10R75A.0029 | 30 | b | N | G-1_V1insN | NVPL (SEQ ID NO: 247) . . . | hCXCL10R75A.0029-G1T4k.one//VHn-G1T4h.one.H435R |
| hCXCL10R75A.0030 | 31 | b | P | G-1_V1insP | PVPL (SEQ ID NO: 248) . . . | hCXCL10R75A.0030-G1T4k.one//VHn-G1T4h.one.H435R |
| hCXCL10R75A.0031 | 32 | b | Q | G-1_V1insQ | QVPL (SEQ ID NO: 249) . . . | hCXCL10R75A.0031-G1T4k.one//VHn-G1T4h.one.H435R |
| hCXCL10R75A.0032 | 33 | b | R | G-1_V1insR | RVPL (SEQ ID NO: 250) . . . | hCXCL10R75A.0032-G1T4k.one//VHn-G1T4h.one.H435R |
| hCXCL10R75A.0033 | 34 | b | S | G-1_V1insS | SVPL (SEQ ID NO: 251) . . . | hCXCL10R75A.0033-G1T4k.one//VHn-G1T4h.one.H435R |
| hCXCL10R75A.0034 | 35 | b | T | G-1_V1insT | TVPL (SEQ ID NO: 252) . . . | hCXCL10R75A.0034-G1T4k.one//VHn-G1T4h.one.H435R |
| hCXCL10R75A.0035 | 36 | b | V | V1dup or G-1_V1insV or V1_P2insV | VVPL (SEQ ID NO: 253) . . . | hCXCL10R75A.0035-G1T4k.one//VHn-G1T4h.one.H435R |
| hCXCL10R75A.0036 | 37 | b | W | G-1_V1insW | WVPL (SEQ ID NO: 254) . . . | hCXCL10R75A.0036-G1T4k.one//VHn-G1T4h.one.H435R |
| hCXCL10R75A.0037 | 38 | b | Y | G-1_V1insY | YVPL (SEQ ID NO: 255) . . . | hCXCL10R75A.0037-G1T4k.one//VHn-G1T4h.one.H435R |
| hCXCL10R75A.0038 | 39 | c | A | V1_P2insA | VAPL (SEQ ID NO: 256) . . . | hCXCL10R75A.0038-G1T4k.one//VHn-G1T4h.one.H435R |
| hCXCL10R75A.0039 | 40 | c | D | V1_P2insD | VDPL (SEQ ID NO: 257) . . . | hCXCL10R75A.0039-G1T4k.one//VHn-G1T4h.one.H435R |
| hCXCL10R75A.0040 | 41 | c | E | V1_P2insE | VEPL (SEQ ID NO: 258) . . . | hCXCL10R75A.0040-G1T4k.one//VHn-G1T4h.one.H435R |
| hCXCL10R75A.0041 | 42 | c | F | V1_P2insF | VFPL (SEQ ID NO: 259) . . . | hCXCL10R75A.0041-G1T4k.one//VHn-G1T4h.one.H435R |
| hCXCL10R75A.0042 | 43 | c | G | V1_P2insG | VGPL (SEQ ID NO: 260) . . . | hCXCL10R75A.0042-G1T4k.one//VHn-G1T4h.one.H435R |
| hCXCL10R75A.0043 | 44 | c | H | V1_P2insH | VHPL (SEQ ID NO: 261) . . . | hCXCL10R75A.0043-G1T4k.one//VHn-G1T4h.one.H435R |
| hCXCL10R75A.0044 | 45 | c | I | V1_P2insI | VIPL (SEQ ID NO: 262) . . . | hCXCL10R75A.0044-G1T4k.one//VHn-G1T4h.one.H435R |
| hCXCL10R75A.0045 | 46 | c | K | V1_P2insK | VKPL (SEQ ID NO: 263) . . . | hCXCL10R75A.0045-G1T4k.one//VHn-G1T4h.one.H435R |
| hCXCL10R75A.0046 | 47 | c | L | V1_P2insL | VLPL (SEQ ID NO: 264) . . . | hCXCL10R75A.0046-G1T4k.one//VHn-G1T4h.one.H435R |
| hCXCL10R75A.0047 | 48 | c | M | V1_P2insM | VMPL (SEQ ID NO: 265) . . . | hCXCL10R75A.0047-G1T4k.one//VHn-G1T4h.one.H435R |
| hCXCL10R75A.0048 | 49 | c | N | V1_P2insN | VNPL (SEQ ID NO: 266) . . . | hCXCL10R75A.0048-G1T4k.one//VHn-G1T4h.one.H435R |
| hCXCL10R75A.0049 | 50 | c | P | P2dup or V1_P2insP or P2_L3insP | VPPL (SEQ ID NO: 267) . . . | hCXCL10R75A.0049-G1T4k.one//VHn-G1T4h.one.H435R |
| hCXCL10R75A.0050 | 51 | c | Q | V1_P2insQ | VQPL (SEQ ID NO: 268) . . . | hCXCL10R75A.0050-G1T4k.one//VHn-G1T4h.one.H435R |
| hCXCL10R75A.0051 | 52 | c | R | V1_P2insR | VRPL (SEQ ID NO: 269) . . . | hCXCL10R75A.0051-G1T4k.one//VHn-G1T4h.one.H435R |
| hCXCL10R75A.0052 | 53 | c | S | V1_P2insS | VSPL (SEQ ID NO: 270) . . . | hCXCL10R75A.0052-G1T4k.one//VHn-G1T4h.one.H435R |
| hCXCL10R75A.0053 | 54 | c | T | V1_P2insT | VTPL (SEQ ID NO: 271) . . . | hCXCL10R75A.0053-G1T4k.one//VHn-G1T4h.one.H435R |
| hCXCL10R75A.0054 | 55 | c | V | V1dup or G-1_V1insV or V1_P2insV | VVPL (SEQ ID NO: 272) . . . | hCXCL10R75A.0054-G1T4k.one//VHn-G1T4h.one.H435R |
| hCXCL10R75A.0055 | 56 | c | W | V1_P2insW | VWPL (SEQ ID NO: 273) . . . | hCXCL10R75A.0055-G1T4k.one//VHn-G1T4h.one.H435R |
| hCXCL10R75A.0056 | 57 | c | Y | V1_P2insY | VYPL (SEQ ID NO: 274) . . . | hCXCL10R75A.0056-G1T4k.one//VHn-G1T4h.one.H435R |

In order to facilitate the purification of the various hCXCL10 variants, hCXCL10 variant Fc fusions were constructed by fusing the hCXCL10 variants with the human IgG1 antibody Fc domain. A schematic diagram of an hCXCL10 variant Fc fusion is shown in FIG. 1A.

hCXCL10 variant Fc fusions, in which the above hCXCL10 variants are fused with the human IgG1 antibody (hIgG1) Fc domain variant G1T4k.one//VHn-G1T4h.one.H435R (G1T4k.one (SEQ ID NO: 58) and VHn-G1T4h.one.H435R (SEQ ID NO: 59)), were prepared. Specifically, expression vectors encoding genes of peptide chains in which the C-terminus of each hCXCL10 variant and the N-terminus of G1T4k.one in G1T4k.one//VHn-G1T4h.one.H435R are linked were prepared using a method known to those skilled in the art. These peptide chains were combined with VHn-G1T4h.one.H435R, and hCXCL10 variant Fc fusions, in which one hCXCL10 variant is bound to an hIgG1 Fc domain variant, were expressed by transient expression using Expi 293 (Life Technologies) by a method known to those skilled in the art and purified by a method known to those skilled in the art using protein A.

The Fc domain variant used in this study has a mutation for increasing the yield of Fc heteroassociated molecules and a mutation that suppresses FecγR binding.

Example 2. Evaluation of the Cell Migration-Inducing Activity of hCXCL10 Variant Fc Fusions Whether the hCXCL10 variant Fc fusions prepared in Example 1 induce migration of cells expressing the CXCL10 receptor (cell migration-inducing activity) was evaluated. hCXCL10R75A was used as a positive control of cell migration-inducing activity. hCXCL10R75A was expressed by transient expression using Expi293 (Life Technologies) by a method known to those skilled in the art, and purified by a method known to those skilled in the art using heparin sepharose (HiTrap Heparin HP Column GE Healthcare), SP sepharose (HiTrap SP HP Column GE Healthcare), and gel filtration (HiLoadSuperdex 75pg GE Healthcare).

Cell migration-inducing activity was evaluated using Ba/F3 transfectant cells expressing mouse CXCR3 (mCXCR3) (hereinafter referred to as BaF3/mCXCR3) and HTS Transwell™-96 Permeable Supports with 5.0 μm Pore Polycarbonate Membrane (Cat. 3387, Corning).

As analytes, hCXCL10 (PeproTech, cat 300-12), hCXCL10R75A, and the following hCXCL10 variant Fc fusions prepared in Example 1 were used:

hCXCL10R75A-G1T4k.one//VHn-G1T4h.one.H435R,
hCXCL10R75A.0001-G1T4k.one//VHn-G1T4h.one.H435R,
hCXCL10R75A.0002-G1T4k.one//VHn-G1T4h.one.H435R,
hCXCL10R75A.0003-G1T4k.one//VHn-G1T4h.one.H435R,
hCXCL10R75A.0004-G1T4k.one//VHn-G1T4h.one.H435R,
hCXCL10R75A.0005-G1T4k.one//VHn-G1T4h.one.H435R,
hCXCL10R75A.0006-G1T4k.one//VHn-G1T4h.one.H435R,
hCXCL10R75A.0007-G1T4k.one//VHn-G1T4h.one.H435R,
hCXCL10R75A.0009-G1T4k.one//VHn-G1T4h.one.H435R,
hCXCL10R75A.0010-G1T4k.one//VHn-G1T4h.one.H435R,
hCXCL10R75A.0011-G1T4k.one//VHn-G1T4h.one.H435R,
hCXCL10R75A.0012-G1T4k.one//VHn-G1T4h.one.H435R,
hCXCL10R75A.0013-G1T4k.one//VHn-G1T4h.one.H435R,
hCXCL10R75A.0014-G1T4k.one//VHn-G1T4h.one.H435R,
hCXCL10R75A.0015-G1T4k.one//VHn-G1T4h.one.H435R,
hCXCL10R75A.0016-G1T4k.one//VHn-G1T4h.one.H435R,
hCXCL10R75A.0017-G1T4k.one//VHn-G1T4h.one.H435R, hCXCL10R75A.0018-G1T4k.one//VHn-G1T4h.one.H435R,
hCXCL10R75A.0019-G1T4k.one//VHn-G1T4h.one.H435R,
hCXCL10R75A.0020-G1T4k.one//VHn-G1T4h.one.H435R,
hCXCL10R75A.0021-G1T4k.one//VHn-G1T4h.one.H435R,
hCXCL10R75A.0023-G1T4k.one//VHn-G1T4h.one.H435R,
hCXCL10R75A.0025-G1T4k.one//VHn-G1T4h.one.H435R,
hCXCL10R75A.0027-G1T4k.one//VHn-G1T4h.one.H435R,
hCXCL10R75A.0029-G1T4k.one//VHn-G1T4h.one.H435R,
hCXCL10R75A.0031-G1T4k.one//VHn-G1T4h.one.H435R,
hCXCL10R75A.0033-G1T4k.one//VHn-G1T4h.one.H435R,
hCXCL10R75A.0034-G1T4k.one//VHn-G1T4h.one.H435R,
hCXCL10R75A.0036-G1T4k.one//VHn-G1T4h.one.H435R,
hCXCL10R75A.0038-G1T4k.one//VHn-G1T4h.one.H435R,
hCXCL10R75A.0039-G1T4k.one//VHn-G1T4h.one.H435R,
hCXCL10R75A.0040-G1T4k.one//VHn-G1T4h.one.H435R,
hCXCL10R75A.0041-G1T4k.one//VHn-G1T4h.one.H435R,
hCXCL10R75A.0042-G1T4k.one//VHn-G1T4h.one.H435R,
hCXCL10R75A.0044-G1T4k.one//VHn-G1T4h.one.H435R,
hCXCL10R75A.0047-G1T4k.one//VHn-G1T4h.one.H435R,
hCXCL10R75A.0048-G1T4k.one//VHn-G1T4h.one.H435R,
hCXCL10R75A.0049-G1T4k.one//VHn-G1T4h.one.H435R,
hCXCL10R75A.0053-G1T4k.one//VHn-G1T4h.one.H435R, and
hCXCL10R75A.0054-G1T4k.one//VHn-G1T4h.one.H435R.

After adjusting the final concentrations in the solutions of each analyte to be analyzed to 100 nM, 300 nM, and 1000 nM, 235 μL of each solution was transferred to the lower chamber. Then, BaF3/mCXCR3 cells were seeded into the upper chamber at 75 μL/well so as to be $2.0 \times 10^5$ cells/well, and the reaction was carried out for 6 hours or 3 hours. The reaction was carried out under the conditions of 5% carbon dioxide and 37° C. After 3 or 6 hours of reaction, 100 μL of the solution in the lower chamber was transferred to Opti-Plate-96 (Cat. 6005299, PerkinElmer) and 100 μL of Cell-Titer-Glo™ Luminescent Cell Viability Assay solution (Cat. G7571, Promega) was added. After reacting at room temperature for 10 minutes, the luminescence value was measured with a SpectraMax M3 multimode microplate reader (Molecular Devices) to evaluate the level of migration of cells into the lower chamber.

The luminescence intensity reflects the amount of cells that migrated into the lower chamber. Comparison of the cell migration-inducing activities of hCXCL10 (PeproTech, cat 300-12) and hCXCL10R75A and comparison of the cell migration-inducing activities of hCXCL10R75A-

G1T4k.one//VHn-G1T4 h.one.H435R and other hCXCL10 variant Fc fusions were conducted, respectively.

Figure 2:
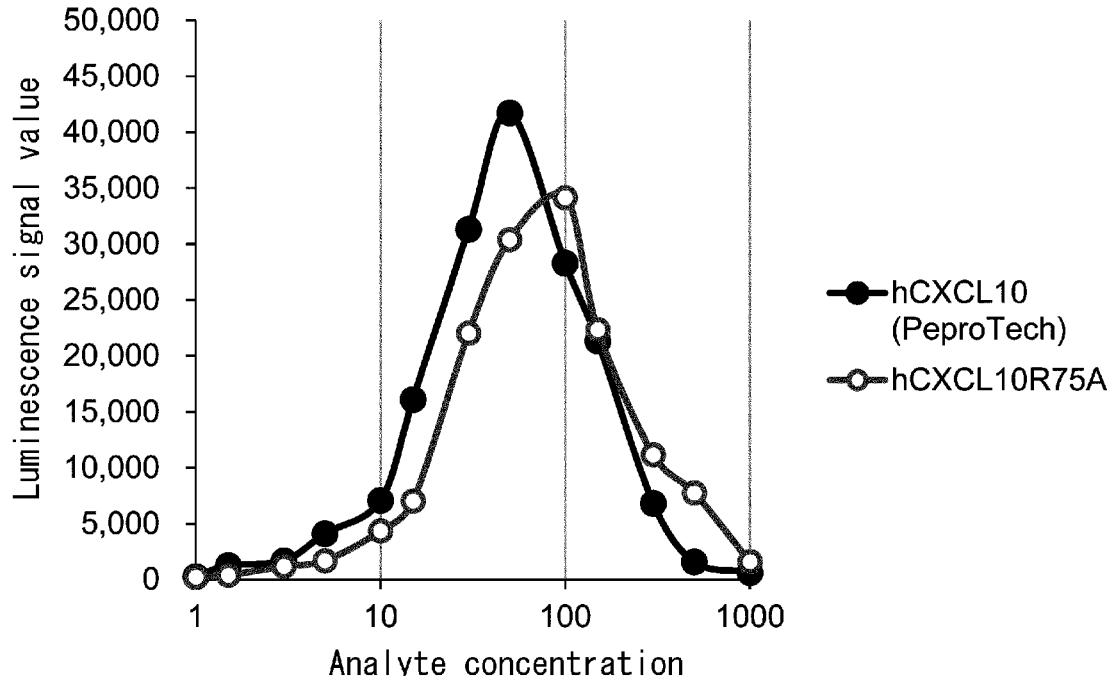
FIG. 2 shows the cell migration-inducing activity of hCXCL10 (PeproTech, cat 300-12) and hCXCL10R75A.
Figure 3A:
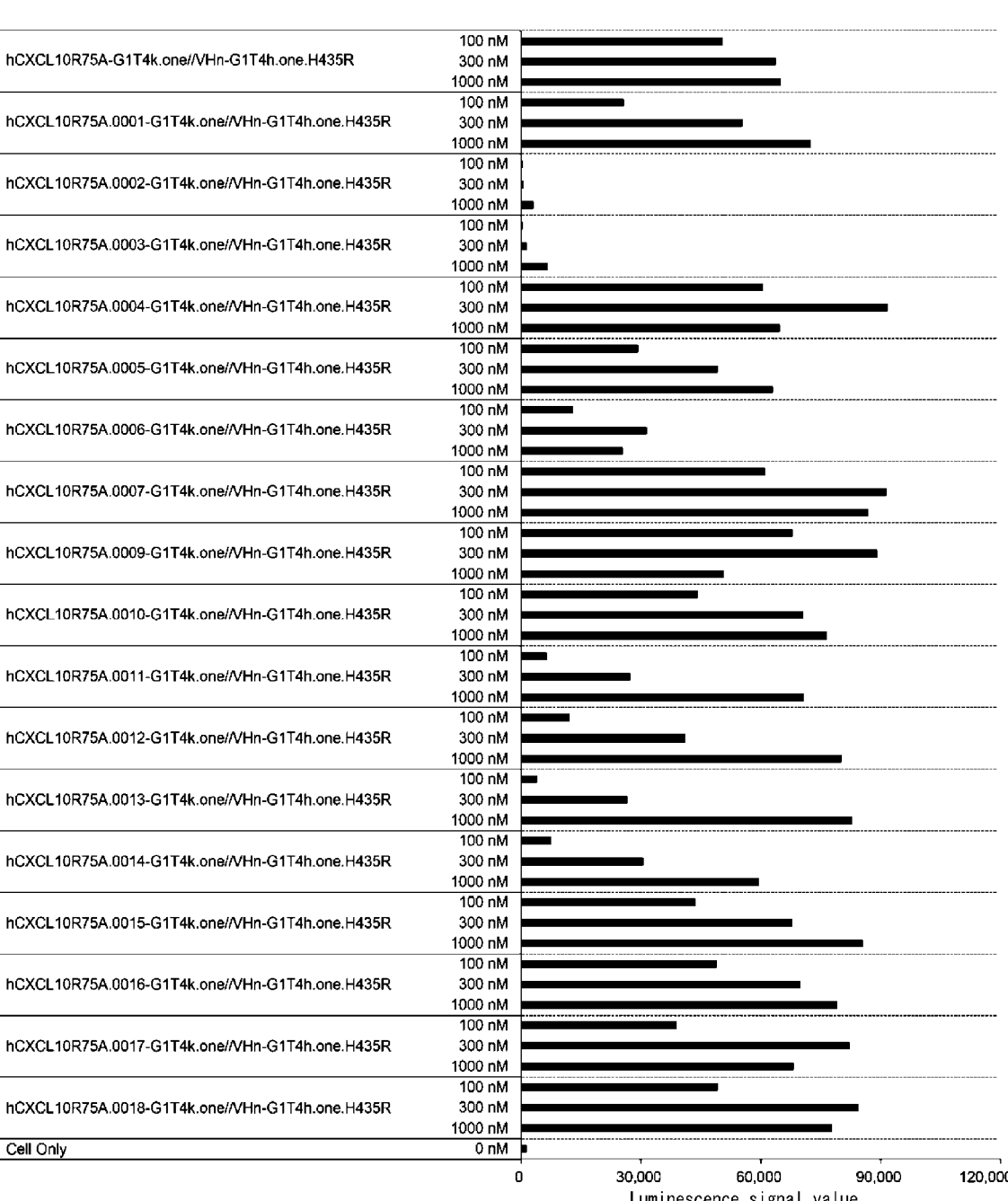
FIG. 3a shows the cell migration-inducing activity of each hCXCL10 variant Fc fusion.

Comparison of the cell migration-inducing activity between hCXCL10 (PeproTech, cat 300-12) and hCXCL10R75A was performed after 6 hours of reaction, and the results are shown in FIG. 2 and Table 3. Both hCXCL10 (PeproTech, cat 300-12) and hCXCL10R75A showed concentration-dependent cell migration-inducing activity, and there was no significant difference in their dependence. From this, it was shown that hCXCL10R75A which was modified to have resistance to furin protease has a similar activity as the wild type.

TABLE 3

| Analyte name | Analyte concentration | Luminescence value |
| --- | --- | --- |
| hCXCL10 | 1 nM | 257 |
| (PeproTech) | 1.5 nM | 1252 |
| | 3 nM | 1677 |
| | 5 nM | 4118 |
| | 10 nM | 7094 |
| | 15 nM | 16110 |
| | 30 nM | 31321 |
| | 50 nM | 41726 |
| | 100 nM | 28288 |
| | 150 nM | 21343 |
| | 300 nM | 6822 |
| | 500 nM | 1587 |
| | 1000 nM | 634 |
| hCXCL10R75A | 1 nM | 207 |
| | 1.5 nM | 389 |
| | 3 nM | 1185 |
| | 5 nM | 1677 |
| | 10 nM | 4354 |
| | 15 nM | 7024 |
| | 30 nM | 22026 |
| | 50 nM | 30392 |
| | 100 nM | 34130 |
| | 150 nM | 22345 |
| | 300 nM | 11163 |
| | 500 nM | 7751 |
| | 1000 nM | 1599 |
| cell only | 0 nM | 275 |

Figures 1, 6:
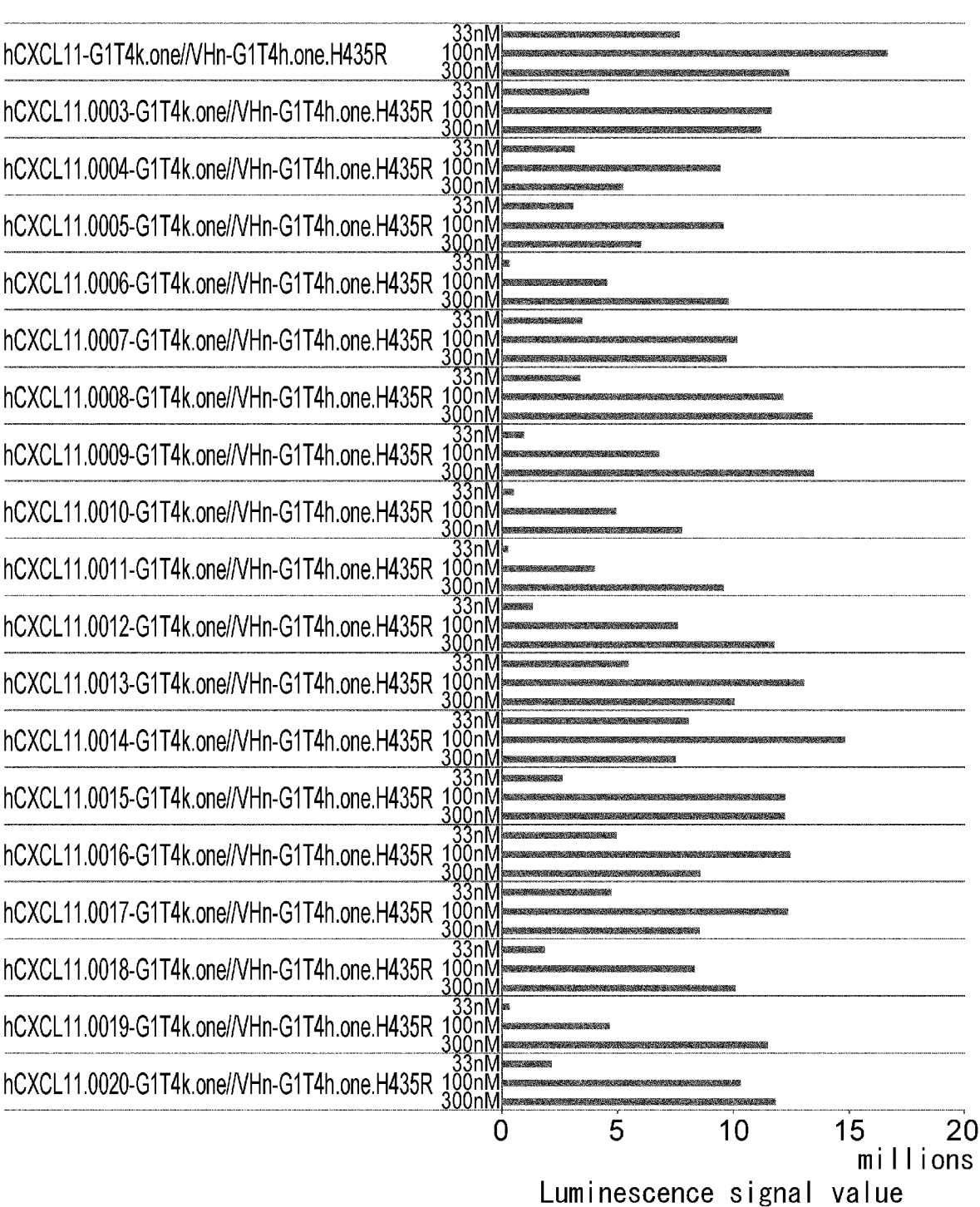
FIG. 6-1 shows the cell migration-inducing activity of each hCXCL11 variant Fc fusion.
Figures 2, 6:
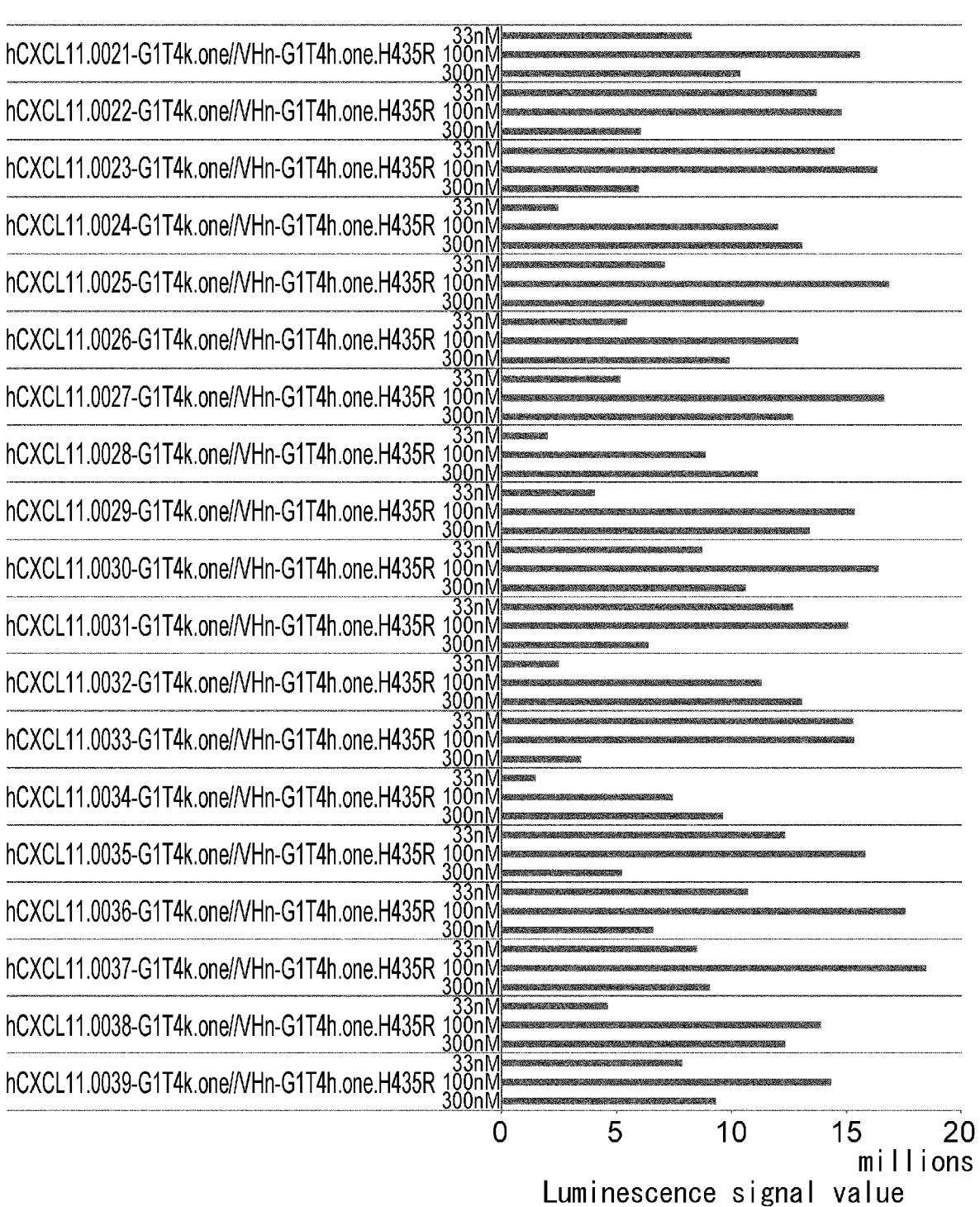
Figures 3, 6:
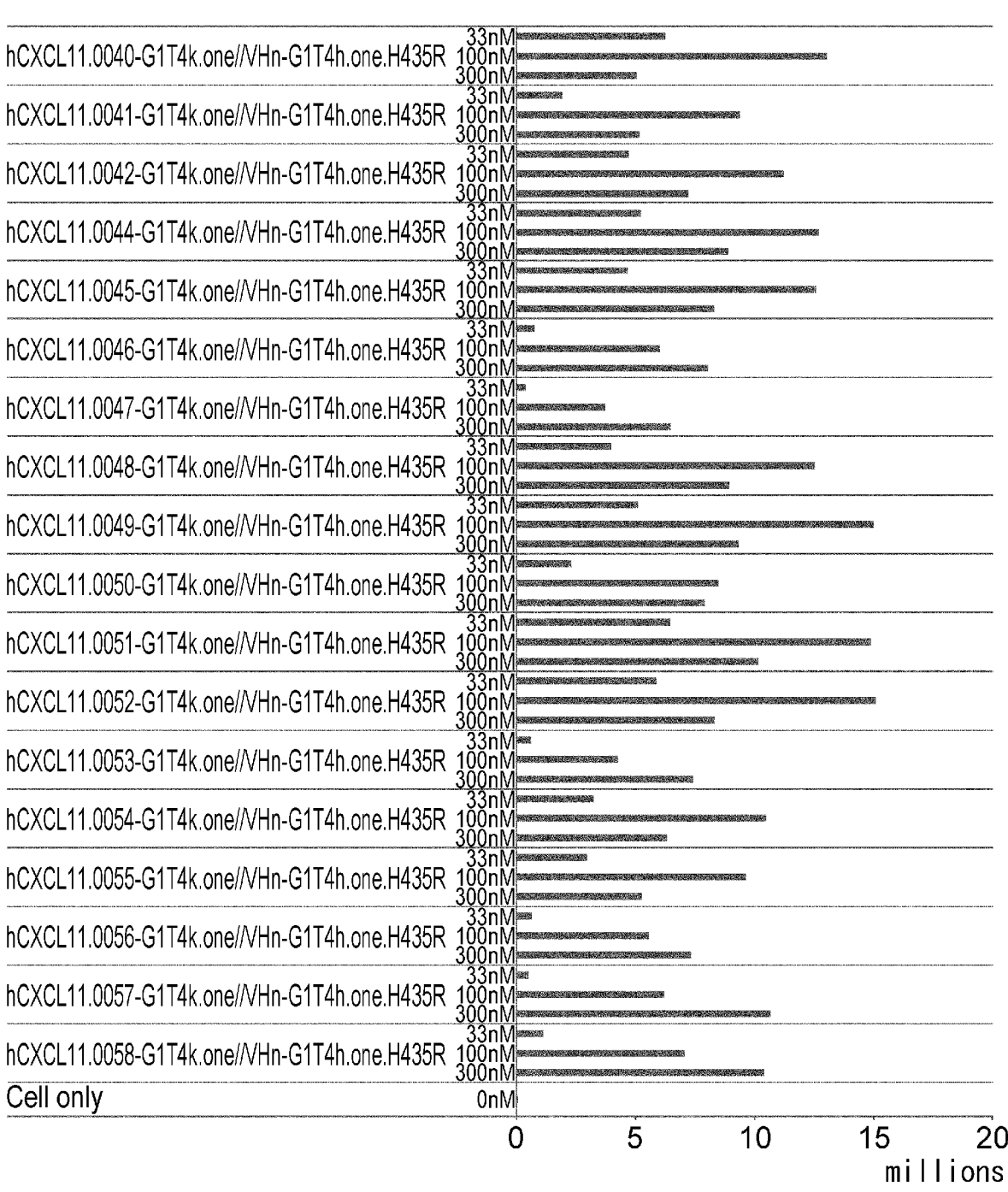

Comparison of the cell migration-inducing activity between hCXCL10R75A-G1T4k.one//VHn-G1T4h.one.H435R and other hCXCL10 variant Fc fusions was performed after 3 hours of reaction, and the results are shown in FIG. 3 and Table 4 (Table 4a, Table 4b-1, and Table 4b-2). Compared to hCXCL10R75A-G1T4k.one//VHn-G1T4h.one.H435R, hCXCL10R75A.0001-G1T4k.one//VHn-G1T4 h.one.H435R,
hCXCL10R75A.0004-G1T4k.one//VHn-G1T4h.one.H435R,
hCXCL10R75A.0005-G1T4k.one//VHn-G1T4h.one.H435R, hCXCL10R75A.0007-G1T4k.one//VHn-G1T4h.one.H435R,
hCXCL10R75A.0009-G1T4k.one//VHn-G1T4h.one.H435R,
hCXCL10R75A.0010-G1T4k.one//VHn-G1T4h.one.H435R,
hCXCL10R75A.0015-G1T4k.one//VHn-G1T4h.one.H435R,
hCXCL10R75A.0016-G1T4k.one//VHn-G1T4h.one.H435R,
hCXCL10R75A.0017-G1T4k.one//VHn-G1T4h.one.H435R,
hCXCL10R75A.0018-G1T4k.one//VHn-G1T4h.one.H435R,
hCXCL10R75A.0019-G1T4k.one//VHn-G1T4h.one.H435R,
hCXCL10R75A.0023-G1T4k.one//VHn-G1T4h.one.H435R,
hCXCL10R75A.0025-G1T4k.one//VHn-G1T4h.one.H435R,
hCXCL10R75A.0027-G1T4k.one//VHn-G1T4h.one.H435R,
hCXCL10R75A.0029-G1T4k.one//VHn-G1T4h.one.H435R,
hCXCL10R75A.0031-G1T4k.one//VHn-G1T4h.one.H435R,
hCXCL10R75A.0033-G1T4k.one//VHn-G1T4h.one.H435R,
hCXCL10R75A.0034-G1T4k.one//VHn-G1T4h.one.H435R,
hCXCL10R75A.0036-G1T4k.one//VHn-G1T4h.one.H435R,
hCXCL10R75A.0038-G1T4k.one//VHn-G1T4h.one.H435R,
hCXCL10R75A.0041-G1T4k.one//VHn-G1T4h.one.H435R,
hCXCL10R75A.0042-G1T4k.one//VHn-G1T4h.one.H435R,
hCXCL10R75A.0044-G1T4k.one//VHn-G1T4h.one.H435R,
hCXCL10R75A.0047-G1T4k.one//VHn-G1T4h.one.H435R,
hCXCL10R75A.0049-G1T4k.one//VHn-G1T4h.one.H435R,
hCXCL10R75A.0053-G1T4k.one//VHn-G1T4h.one.H435R, and
hCXCL10R75A.0054-G1T4k.one//VHn-G1T4h.one.H435R retained, at each of the concentrations of 100 nM, 300 nM, and 1000 nM, 30% or more of the cell migration-inducing activity of hCXCL10R75A-G1T4k.one//VHn-G1T4h.one.H435R at the same concentration. From this, it was shown that the human CXCL10 variants contained in these human CXCL10 variant Fc fusions have sufficient activity.

TABLE 4a

| Analyte name | Analyte concentration | Luminescence value | Activity retention rate* |
| --- | --- | --- | --- |
| hCXCL10R75A-G1T4k.one//VHn-G1T4h.one.H435R | 100 nM | 50291 | |
| | 300 nM | 63662 | |
| | 1000 nM | 64934 | |
| hCXCL10R75A.0001-G1T4k.one//VHn-G1T4h.one.H435R | 100 nM | 25665 | 51% |
| | 300 nM | 55400 | 87% |
| | 1000 nM | 72476 | 112% |

TABLE 4a-continued

| Analyte name | Analyte concentration | Luminescence value | Activity retention rate* |
|---|---|---|---|
| hCXCL10R75A.0002-G1T4k.one//VHn-G1T4h.one.H435R | 100 nM | 365 | 1% |
| | 300 nM | 524 | 1% |
| | 1000 nM | 3078 | 5% |
| hCXCL10R75A.0003-G1T4k.one//VHn-G1T4h.one.H435R | 100 nM | 402 | 1% |
| | 300 nM | 1319 | 2% |
| | 1000 nM | 6634 | 10% |
| hCXCL10R75A.0004-G1T4k.one//VHn-G1T4h.one.H435R | 100 nM | 60499 | 120% |
| | 300 nM | 91666 | 144% |
| | 1000 nM | 64738 | 100% |
| hCXCL10R75A.0005-G1T4k.one//VHn-G1T4h.one.H435R | 100 nM | 29314 | 58% |
| | 300 nM | 49215 | 77% |
| | 1000 nM | 62988 | 97% |
| hCXCL10R75A.0006-G1T4k.one//VHn-G1T4h.one.H435R | 100 nM | 13034 | 26% |
| | 300 nM | 31410 | 49% |
| | 1000 nM | 25422 | 39% |
| hCXCL10R75A.0007-G1T4k.one//VHn-G1T4h.one.H435R | 100 nM | 61004 | 121% |
| | 300 nM | 91432 | 144% |
| | 1000 nM | 86763 | 134% |
| hCXCL10R75A.0009-G1T4k.one//VHn-G1T4h.one.H435R | 100 nM | 67910 | 135% |
| | 300 nM | 89121 | 140% |
| | 1000 nM | 50563 | 78% |
| hCXCL10R75A.0010-G1T4k.one//VHn-G1T4h.one.H435R | 100 nM | 44181 | 88% |
| | 300 nM | 70501 | 111% |
| | 1000 nM | 76518 | 118% |
| hCXCLI 0R75A.0011-G1T4k.one//VHn-G1T4h.one.H435R | 100 nM | 6447 | 13% |
| | 300 nM | 27284 | 43% |
| | 1000 nM | 70810 | 109% |
| hCXCL10R75A.0012-G1T4k.one//VHn-G1T4h.one.H435R | 100 nM | 12277 | 24% |
| | 300 nM | 41113 | 65% |
| | 1000 nM | 80105 | 123% |
| hCXCL10R75A.0013-G1T4k.one//VHn-G1T4h.one.H435R | 100 nM | 3951 | 8% |
| | 300 nM | 26601 | 42% |
| | 1000 nM | 82839 | 128% |
| hCXCL10R75A.0014-G1T4k.one//VHn-G1T4h.one.H435R | 100 nM | 7581 | 15% |
| | 300 nM | 30656 | 48% |
| | 1000 nM | 59567 | 92% |
| hCXCL10R75A.0015-G1T4k.one//VHn-G1T4h.one.H435R | 100 nM | 43622 | 87% |
| | 300 nM | 67799 | 106% |
| | 1000 nM | 85480 | 132% |
| hCXCL10R75A.0016-G1T4k.one//VHn-G1T4h.one.H435R | 100 nM | 48930 | 97% |
| | 300 nM | 69864 | 110% |
| | 1000 nM | 79077 | 122% |
| hCXCL10R75A.0017-G1T4k.one//VHn-G1T4h.one.H435R | 100 nM | 38888 | 77% |
| | 300 nM | 82142 | 129% |
| | 1000 nM | 68224 | 105% |
| hCXCL10R75A.0018-G1T4k.one//VHn-G1T4h.one.H435R | 100 nM | 49213 | 98% |
| | 300 nM | 84292 | 132% |
| | 1000 nM | 77813 | 120% |
| cell only | 0 nM | 1348 | — |

Activity retention rate*: percentage to the signal value of hCXCL10R75A-G1T4k.one//VHn-G1T4h.one.H435R at the corresponding concentration TABLE 4b

| Analyte name | Analyte concentration | Luminescence value | Activity retention rate* |
|---|---|---|---|
| hCXCL10R75A-G1T4k.one//VHn-G1T4h.one.H435R | 100 nM | 30093 | |
| | 300 nM | 52215 | |
| | 1000 nM | 70794 | |
| hCXCL10R75A.0019-G1T4k.one//VHn-G1T4h.one.H435R | 100 nM | 19969 | 66% |
| | 300 nM | 48281 | 92% |
| | 1000 nM | 70794 | 100% |
| hCXCL10R75A.0020-G1T4k.one//VHn-G1T4h.one.H435R | 100 nM | 503 | 2% |
| | 300 nM | 1296 | 2% |
| | 1000 nM | 13592 | 19% |
| hCXCL10R75A.0021-G1T4k.one//VHn-G1T4h.one.H435R | 100 nM | 531 | 2% |
| | 300 nM | 671 | 1% |
| | 1000 nM | 10553 | 15% |
| hCXCL10R75A.0023-G1T4k.one//VHn-G1T4h.one.H435R | 100 nM | 27473 | 91% |
| | 300 nM | 55608 | 106% |
| | 1000 nM | 74001 | 105% |

TABLE 4b-continued

| Analyte name | Analyte concentration | Luminescence value | Activity retention rate* |
|---|---|---|---|
| hCXCL10R75A.0025-G1T4k.one//VHn-G1T4h.one.H435R | 100 nM | 29422 | 98% |
| | 300 nM | 62870 | 120% |
| | 1000 nM | 87538 | 124% |
| hCXCL10R75A.0027-G1T4k.one//VHn-G1T4h.one.H435R | 100 nM | 36702 | 122% |
| | 300 nM | 67093 | 128% |
| | 1000 nM | 76975 | 109% |
| hCXCL10R75A.0029-G1T4k.one//VHn-G1T4h.one.H435R | 100 nM | 22048 | 73% |
| | 300 nM | 48887 | 94% |
| | 1000 nM | 74244 | 105% |
| hCXCL10R75A.0031-G1T4k.one//VHn-G1T4h.one.H435R | 100 nM | 26942 | 90% |
| | 300 nM | 47666 | 91% |
| | 1000 nM | 74663 | 105% |
| hCXCL10R75A.0033-G1T4k.one//VHn-G1T4h.one.H435R | 100 nM | 23828 | 79% |
| | 300 nM | 47833 | 92% |
| | 1000 nM | 72566 | 103% |

TABLE 4b-continued

| Analyte name | Analyte concen-tration | Lumines-cence value | Activity retention rate* |
|---|---|---|---|
| hCXCL10R75A.0034-G1T4k.one//VHn-G1T4h.one.H435R | 100 nM | 26755 | 89% |
|  | 300 nM | 52616 | 101% |
|  | 1000 nM | 68706 | 97% |
| hCXCL10R75A.0036-G1T4k.one//VHn-G1T4h.one.H435R | 100 nM | 25990 | 86% |
|  | 300 nM | 77812 | 149% |
|  | 1000 nM | 82063 | 116% |
| hCXCL10R75A.0038-G1T4k.one//VHn-G1T4h.one.H435R | 100 nM | 15307 | 51% |
|  | 300 nM | 52204 | 100% |
|  | 1000 nM | 79611 | 112% |
| hCXCL10R75A.0039-G1T4k.one//VHn-G1T4h.one.H435R | 100 nM | 373 | 1% |
|  | 300 nM | 559 | 1% |
|  | 1000 nM | 4633 | 7% |
| hCXCL10R75A.0040-G1T4k.one//VHn-G1T4h.one.H435R | 100 nM | 336 | 1% |
|  | 300 nM | 653 | 1% |
|  | 1000 nM | 6339 | 9% |
| hCXCL10R75A.0041-G1T4k.one//VHn-G1T4h.one.H435R | 100 nM | 42584 | 142% |
|  | 300 nM | 73123 | 140% |
|  | 1000 nM | 83769 | 118% |
| hCXCL10R75A.0042-G1T4k.one//VHn-G1T4h.one.H435R | 100 nM | 40067 | 133% |
|  | 300 nM | 59914 | 115% |
|  | 1000 nM | 78325 | 111% |
| hCXCL10R75A.0044-G1T4k.one//VHn-G1T4h.one.H435R | 100 nM | 31472 | 105% |
|  | 300 nM | 73850 | 141% |
|  | 1000 nM | 91553 | 129% |
| hCXCL10R75A.0047-G1T4k.one//VHn-G1T4h.one.H435R | 100 nM | 28498 | 95% |
|  | 300 nM | 66644 | 128% |
|  | 1000 nM | 85941 | 121% |
| hCXCL10R75A.0048-G1T4k.one//VHn-G1T4h.one.H435R | 100 nM | 4559 | 15% |
|  | 300 nM | 33606 | 64% |
|  | 1000 nM | 40822 | 58% |
| hCXCL10R75A.0049-G1T4k.one//VHn-G1T4h.one.H435R | 100 nM | 48792 | 162% |
|  | 300 nM | 71949 | 138% |
|  | 1000 nM | 80469 | 114% |
| hCXCL10R75A.0053-G1T4k.one//VHn-G1T4h.one.H435R | 100 nM | 10497 | 35% |
|  | 300 nM | 47981 | 92% |
|  | 1000 nM | 78791 | 111% |
| hCXCL10R75A.0054-G1T4k.one//VHn-G1T4h.one.H435R | 100 nM | 28405 | 94% |
|  | 300 nM | 67371 | 129% |
|  | 1000 nM | 73636 | 104% |
| cell only | 0 nM | 792 | — |

Activity retention rate*: percentage to the signal value of hCXCL10R75A-G1T4k.one//VHn-G1T4h.one.H435R at the corresponding concentration

Example 3. Evaluation of DPPIV Cleavage Resistance of hCXCL10 Variant Fe Fusions It was examined whether the hCXCL10 variant Fc fusions that induced cell migration in Example 2 are cleaved by DPPIV. Dipeptidyl peptidase IV derived from human (human DPPIV, hDPPIV) (Biolegend, 764102) was used as the protease. Cleavage of the hCXCL10 variant Fc fusions by the protease was evaluated by LC/MS analysis after degly-cosylation treatment. After reacting hCXCL10 variant Fc fusions at a final concentration of 0.2 mg/ml and hDPPIV at a final concentration of 200 nM at 37° C. for 1 hour, mass spectrometry by LC/MS was performed by a method known to those skilled in the art, and the cleavage of the hCXCL10 variant Fc fusions was evaluated. For hCXCL10R75A-G1T4k.one//VHn-G1T4h.one.H435R and hCXCL10R75A.0001-G1T4k.one//VHn-G1T4h.one.H435R, protease treatment reduced the mass of the hCXCL10 variant-containing peptide chain in the hCXCL10 variant Fc fusions, and this mass was consistent with the theoretical mass of the sequences of each of the hCXCL10 variant-containing peptide chains lacking the two N-terminal residues. This suggested that the two amino acid residues from the N-terminal of the human CXCL10 variants (hCXCL10R75A, hCXCL10R75A.0001) contained in hCXCL10R75A-G1T4k.one//VHn-G1T4h.one.H435R and hCXCL10R75A.0001-G1T4k.one//VHn-G1T4h.one.H435R were cleaved by hDPPIV.

On the other hand, hCXCL10R75A.0004-G1T4k.one//VHn-G1T4h.one.H435R, hCXCL10R75A.0005-G1T4k.one//VHn-G1T4h.one.H435R, hCXCL10R75A.0007-G1T4k.one//VHn-G1T4h.one.H435R, hCXCL10R75A.0009-G1T4k.one//VHn-G1T4h.one.H435R, hCXCL10R75A.0010-G1T4k.one//VHn-G1T4h.one.H435R, hCXCL10R75A.0015-G1T4k.one//VHn-G1T4h.one.H435R, hCXCL10R75A.0016-G1T4k.one//VHn-G1T4h.one.H435R, hCXCL10R75A.0017-G1T4k.one//VHn-G1T4h.one.H435R, hCXCL10R75A.0018-G1T4k.one//VHn-G1T4h.one.H435R, hCXCL10R75A.0019-G1T4k.one//VHn-G1T4h.one.H435R, hCXCL10R75A.0023-G1T4k.one//VHn-G1T4h.one.H435R, hCXCL10R75A.0025-G1T4k.one//VHn-G1T4h.one.H435R, hCXCL10R75A.0027-G1T4k.one//VHn-G1T4h.one.H435R, hCXCL10R75A.0029-G1T4k.one//VHn-G1T4h.one.H435R, hCXCL10R75A.0031-G1T4k.one//VHn-G1T4h.one.H435R, hCXCL10R75A.0033-G1T4k.one//VHn-G1T4h.one.H435R, hCXCL10R75A.0034-G1T4k.one//VHn-G1T4h.one.H435R, hCXCL10R75A.0036-G1T4k.one//VHn-G1T4h.one.H435R, hCXCL10R75A.0038-G1T4k.one//VHn-G1T4h.one.H435R, hCXCL10R75A.0041-G1T4k.one//VHn-G1T4h.one.H435R, hCXCL10R75A.0042-G1T4k.one//VHn-G1T4h.one.H435R, hCXCL10R75A.0044-G1T4k.one//VHn-G1T4h.one.H435R, hCXCL10R75A.0047-G1T4k.one//VHn-G1T4h.one.H435R, hCXCL10R75A.0049-G1T4k.one//VHn-G1T4h.one.H435R, hCXCL10R75A.0053-G1T4k.one//VHn-G1T4h.one.H435R, and hCXCL10R75A.0054-G1T4k.one//VHn-G1T4h.one.H435R showed no change in mass due to hDPPIV treatment (Table 5). This result suggested that the hCXCL10 variants contained in these hCXCL10 variant Fc fusions exhibit hDPPIV cleavage resistance.

TABLE 5

| # | Sample name | hCXCL10-hIgG1 antibody Fc domain fusion protein name | Theoretical mass of the fusion protein (Da) | Measured value (Da) (before DPPIV treatment) | Measured value (Da) (after DPPIV treatment) | Amass (Da) | Comment |
|---|---|---|---|---|---|---|---|
| 1 | hCXCL10R75A-G1T4k.one//VHn-G1T4h.one.H435R | hCXCL10R75A-G1T4k.one | 34627 | 34626 | 34431 | 195 | Loss of the N-terminal VP was suggested |
| 2 | hCXCL10R75A.0001-G1T4k.one//VHn-G1T4h.one.H435R | hCXCL10R75A.0001-G1T4k.one | 34601 | 34601 | 34430 | 171 | Loss of the N-terminal VA was suggested |
| 3 | hCXCL10R75A.0004-G1T4k.one//VHn-G1T4h.one.H435R | hCXCL10R75A.0004-G1T4k.one | 34678 | 34677 | 34676 | 1 | — |
| 4 | hCXCL10R75A.0005-G1T4k.one//VHn-G1T4h.one.H435R | hCXCL10R75A.0005-G1T4k.one | 34587 | 34586 | 34587 | −1 | — |
| 5 | hCXCL10R75A.0007-G1T4k.one//VHn-G1T4h.one.H435R | hCXCL10R75A.0007-G1T4k.one | 34644 | 34643 | 34642 | 1 | — |
| 6 | hCXCL10R75A.0009-G1T4k.one//VHn-G1T4h.one.H435R | hCXCL10R75A.0009-G1T4k.one | 34644 | 34643 | 34642 | 1 | — |
| 7 | hCXCL10R75A.0010-G1T4k.one//VHn-G1T4h.one.H435R | hCXCL10R75A.0010-G1T4k.one | 34662 | 34661 | 34662 | −1 | — |
| 8 | hCXCL10R75A.0015-G1T4k.one//VHn-G1T4h.one.H435R | hCXCL10R75A.0015-G1T4k.one | 34631 | 34630 | 34630 | 0 | — |
| 9 | hCXCL10R75A.0016-G1T4k.one//VHn-G1T4h.one.H435R | hCXCL10R75A.0016-G1T4k.one | 34629 | 34629 | 34628 | 1 | — |
| 10 | hCXCL10R75A.0017-G1T4k.one//VHn-G1T4h.one.H435R | hCXCL10R75A.0017-G1T4k.one | 34717 | 34716 | 34716 | 0 | — |
| 11 | hCXCL10R75A.0018-G1T4k.one//VHn-G1T4h.one.H435R | hCXCL10R75A.0018-G1T4k.one | 34694 | 34693 | 34693 | 0 | — |
| 12 | hCXCL10R75A.0019-G1T4k.one//VHn-G1T4h.one.H435R | hCXCL10R75A.0019-G1T4k.one | 34699 | 34698 | 34697 | 1 | — |
| 13 | hCXCL10R75A.0023-G1T4k.one//VHn-G1T4h.one.H435R | hCXCL10R75A.0023-G1T4k.one | 34685 | 34684 | 34683 | 1 | — |
| 14 | hCXCL10R75A.0025-G1T4k.one//VHn-G1T4h.one.H435R | hCXCL10R75A.0025-G1T4k.one | 34741 | 34740 | 34740 | 0 | — |
| 15 | hCXCL10R75A.0027-G1T4k.one//VHn-G1T4h.one.H435R | hCXCL10R75A.0027-G1T4k.one | 34741 | 34740 | 34739 | 1 | — |
| 16 | hCXCL10R75A.0029-G1T4k.one//VHn-G1T4h.one.H435R | hCXCL10R75A.0029-G1T4k.one | 34742 | 34741 | 34742 | −1 | — |
| 17 | hCXCL10R75A.0031-G1T4k.one//VHn-G1T4h.one.H435R | hCXCL10R75A.0031-G1T4k.one | 34739 | 34738 | 34738 | 0 | — |
| 18 | hCXCL10R75A.0033-G1T4k.one//VHn-G1T4h.one.H435R | hCXCL10R75A.0033-G1T4k.one | 34715 | 34715 | 34713 | 2 | — |
| 19 | hCXCL10R75A.0034-G1T4k.one//VHn-G1T4h.one.H435R | hCXCL10R75A.0034-G1T4k.one | 34729 | 34728 | 34728 | 0 | — |
| 20 | hCXCL10R75A.0036-G1T4k.one//VHn-G1T4h.one.H435R | hCXCL10R75A.0036-G1T4k.one | 34814 | 34813 | 34813 | 0 | — |
| 21 | hCXCL10R75A.0038-G1T4k.one//VHn-G1T4h.one.H435R | hCXCL10R75A.0038-G1T4k.one | 34699 | 34698 | 34698 | 0 | — |
| 22 | hCXCL10R75A.0041-G1T4k.one//VHn-G1T4h.one.H435R | hCXCL10R75A.0041-G1T4k.one | 34775 | 34774 | 34774 | 0 | — |
| 23 | hCXCL10R75A.0042-G1T4k.one//VHn-G1T4h.one.H435R | hCXCL10R75A.0042-G1T4k.one | 34685 | 34685 | 34684 | 1 | — |
| 24 | hCXCL10R75A.0044-G1T4k.one//VHn-G1T4h.one.H435R | hCXCL10R75A.0044-G1T4k.one | 34741 | 34741 | 34741 | 0 | — |
| 25 | hCXCL10R75A.0047-G1T4k.one//VHn-G1T4h.one.H435R | hCXCL10R75A.0047-G1T4k.one | 34759 | 34758 | 34758 | 0 | — |
| 26 | hCXCL10R75A.0049-G1T4k.one//VHn-G1T4h.one.H435R | hCXCL10R75A.0049-G1T4k.one | 34725 | 34725 | 34724 | 1 | — |
| 27 | hCXCL10R75A.0053-G1T4k.one//VHn-G1T4h.one.H435R | hCXCL10R75A.0053-G1T4k.one | 34729 | 34726 | 34728 | −2 | — |
| 28 | hCXCL10R75A.0054-G1T4k.one//VHn-G1T4h.one.H435R | hCXCL10R75A.0054-G1T4k.one | 34727 | 34727 | 34727 | 0 | — |

Since the two residues from the N-terminal of hCXCL10R75A are cleaved by hDPPIV, it was suggested that the amino acid modifications in and around the DPPIV recognition/cleavage site contained in the above hCXCL10 variants that did not show a mass change due to hDPPIV treatment are useful modification to provide DPPIV resistance to hCXCL10.

Figure 4A:
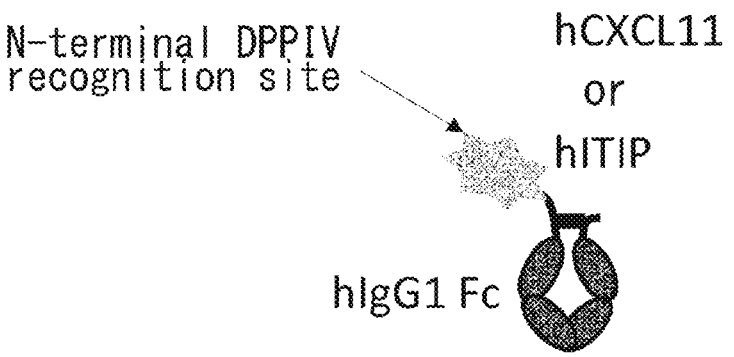
FIG. 4A shows a schematic diagram of an hCXCL11 or hITIP variant Fc fusion.
Figure 4B:
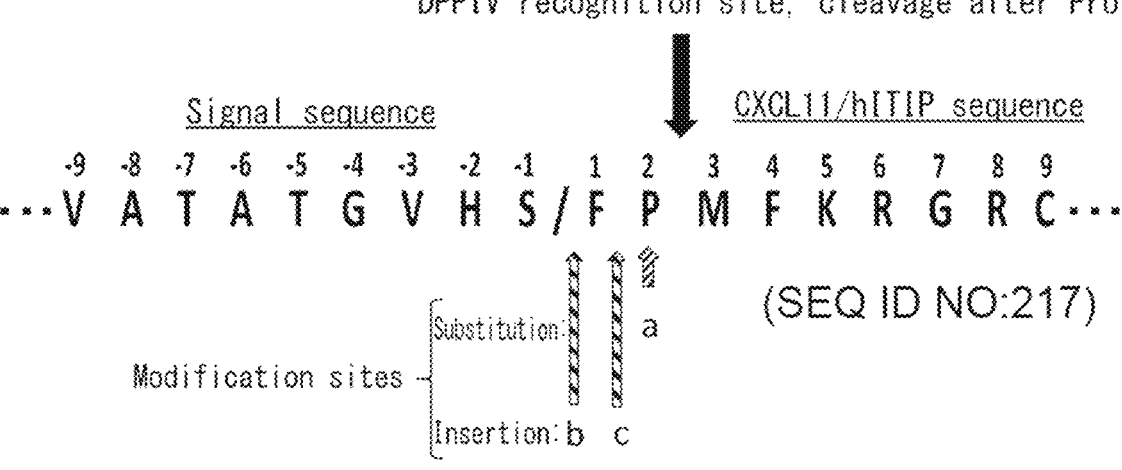
FIG. 4B shows the positions of the amino acid modifications in and around the DPPIV recognition/cleavage site on the sequence VATATGVHSFPMFKRGRC (SEQ ID NO: 217) for producing hCXCL11 or hITIP variants.

Example 4. Construction of Human CXCL11 (hCXCL11) Variants and hCXCL11 Fc Fusions Human CXCL11 (hCXCL11, Refseq: NP_005400.1, Uniprot ID: 014625) (SEQ ID NO: 61) and hCXCL11 variants with amino acid modifications introduced into and around the dipeptidyl peptidase IV (DPPIV) recognition/cleavage site of hCXCL11 were constructed (the amino acid modification positions in and around the DPPIV recognition/cleavage site are shown in FIG. 4B, and the names, sequences, and such of the designed hCXCL11 variants are shown in Table 6).

In order to facilitate the purification of the various hCXCL11 variants, hCXCL11 variant Fc fusions were constructed by fusing the hCXCL11 variants with the human IgG1 antibody Fc domain. A schematic diagram of this is shown in FIG. 4A.

hCXCL11 variant Fc fusions, in which the above hCXCL11 variants are fused with the human IgG1 antibody (hIgG1) Fc domain variant G1T4k.one//VHn-G1T4h.one.H435R (G1T4k.one (SEQ ID NO: 58), VHn-G1T4h.one.H435R (SEQ ID NO: 59)), were prepared. Specifically, expression vectors encoding genes of peptide chains in which the C-terminus of each hCXCL11 variant and the N-terminus of G1T4k.one in G1T4k.one//VHn-G1T4h.one.H435R are linked were prepared using a method known to those skilled in the art. These peptide chains were combined with VHn-G1T4h.one.H435R, and hCXCL11 variant Fc fusions, in which one hCXCL11 variant is bound to an hIgG1 Fc domain variant, were expressed by transient expression using Expi 293 (Life Technologies) by a method known to those skilled in the art and purified by a method known to those skilled in the art using protein A.

The Fc domain variant used in this study has a mutation for increasing the yield of Fc heteroassociated molecules and a mutation that suppresses FecγR binding introduced therein.

TABLE 6

| Sequence Name | SEQ ID NO | Modification pattern | Modified, inserted amino acid residue | Modification | N-terminal sequence | Corresponding hCXCL11 variant Fc fusion |
|---|---|---|---|---|---|---|
| hCXCL11 | 61 | | | | FPMF (SEQ ID NO: 275) . . . | hCXCL11-G1T4k.one//VHn-G1T4h.one.H435R |
| hCXCL11.0003 | 92 | a | A | P2A | FAMF (SEQ ID NO: 276) . . . | hCXCL11.0003-G1T4k.one//VHn-G1T4h.one.H435R |
| hCXCL11.0004 | 93 | a | D | P2D | FDMF (SEQ ID NO: 277) . . . | hCXCL11.0004-G1T4k.one//VHn-G1T4h.one.H435R |
| hCXCL11.0005 | 94 | a | E | P2E | FEMF (SEQ ID NO: 278) . . . | hCXCL11.0005-G1T4k.one//VHn-G1T4h.one.H435R |
| hCXCL11.0006 | 95 | a | F | P2F | FFMF (SEQ ID NO: 279) . . . | hCXCL11.0006-G1T4k.one//VHn-G1T4h.one.H435R |
| hCXCL11.0007 | 96 | a | G | P2G | FGMF (SEQ ID NO: 280) . . . | hCXCL11.0007-G1T4k.one//VHn-G1T4h.one.H435R |
| hCXCL11.0008 | 97 | a | H | P2H | FHMF (SEQ ID NO: 281) . . . | hCXCL11.0008-G1T4k.one//VHn-G1T4h.one.H435R |
| hCXCL11.0009 | 98 | a | I | P2I | FIMF (SEQ ID NO: 282) . . . | hCXCL11.0009-G1T4k.one//VHn-G1T4h.one.H435R |
| hCXCL11.0010 | 99 | a | K | P2K | FKMF (SEQ ID NO: 283) . . . | hCXCL11.0010-G1T4k.one//VHn-G1T4h.one.H435R |
| hCXCL11.0011 | 100 | a | L | P2L | FLMF (SEQ ID NO: 284) . . . | hCXCL11.0011-G1T4k.one//VHn-G1T4h.one.H435R |
| hCXCL11.0012 | 101 | a | M | P2M | FMMF (SEQ ID NO: 285) . . . | hCXCL11.0012-G1T4k.one//VHn-G1T4h.one.H435R |
| hCXCL11.0013 | 102 | a | N | P2N | FNMF (SEQ ID NO: 286) . . . | hCXCL11.0013-G1T4k.one//VHn-G1T4h.one.H435R |
| hCXCL11.0014 | 103 | a | Q | P2Q | FQMF (SEQ ID NO: 287) . . . | hCXCL11.0014-G1T4k.one//VHn-G1T4h.one.H435R |
| hCXCL11.0015 | 104 | a | R | P2R | FRMF (SEQ ID NO: 288) . . . | hCXCL11.0015-G1T4k.one//VHn-G1T4h.one.H435R |
| hCXCL11.0016 | 105 | a | S | P2S | FSMF (SEQ ID NO: 289) . . . | hCXCL11.0016-G1T4k.one//VHn-G1T4h.one.H435R |
| hCXCL11.0017 | 106 | a | T | P2T | FTMF (SEQ ID NO: 290) . . . | hCXCL11.0017-G1T4k.one//VHn-G1T4h.one.H435R |
| hCXCL11.0018 | 107 | a | V | P2V | FVMF (SEQ ID NO: 291) . . . | hCXCL11.0018-G1T4k.one//VHn-G1T4h.one.H435R |
| hCXCL11.0019 | 108 | a | W | P2W | FWMF (SEQ ID NO: 292) . . . | hCXCL11.0019-G1T4k.one//VHn-G1T4h.one.H435R |
| hCXCL11.0020 | 109 | a | Y | P2Y | FYMF (SEQ ID NO: 293) . . . | hCXCL11.0020-G1T4k.one//VHn-G1T4h.one.H435R |
| hCXCL11.0021 | 110 | b | A | S-1_F1insA | AFPM (SEQ ID NO: 294) . . . | hCXCL11.0021-G1T4k.one//VHn-G1T4h.one.H435R |
| hCXCL11.0022 | 111 | b | D | S-1_F1insD | DFPM (SEQ ID NO: 295) . . . | hCXCL11.0022-G1T4k.one//VHn-G1T4h.one.H435R |
| hCXCL11.0023 | 112 | b | E | S-1_F1insE | EFPM (SEQ ID NO: 296) . . . | hCXCL11.0023-G1T4k.one//VHn-G1T4h.one.H435R |
| hCXCL11.0024 | 113 | b | F | S-1_F1insF | FFPM (SEQ ID NO: 297) . . . | hCXCL11.0024-G1T4k.one//VHn-G1T4h.one.H435R |
| hCXCL11.0025 | 114 | b | G | S-1_F1insG | GFPM (SEQ ID NO: 298) . . . | hCXCL11.0025-G1T4k.one//VHn-G1T4h.one.H435R |
| hCXCL11.0026 | 115 | b | H | S-1_F1insH | HFPM (SEQ ID NO: 299) . . . | hCXCL11.0026-G1T4k.one//VHn-G1T4h.one.H435R |
| hCXCL11.0027 | 116 | b | I | S-1_F1insI | IFPM (SEQ ID NO: 300) . . . | hCXCL11.0027-G1T4k.one//VHn-G1T4h.one.H435R |
| hCXCL11.0028 | 117 | b | K | S-1_F1insK | KFPM (SEQ ID NO: 301) . . . | hCXCL11.0028-G1T4k.one//VHn-G1T4h.one.H435R |
| hCXCL11.0029 | 118 | b | L | S-1_F1insL | LFPM (SEQ ID NO: 302) . . . | hCXCL11.0029-G1T4k.one//VHn-G1T4h.one.H435R |
| hCXCL11.0030 | 119 | b | M | S-1_F1insM | MFPM (SEQ ID NO: 303) . . . | hCXCL11.0030-G1T4k.one//VHn-G1T4h.one.H435R |
| hCXCL11.0031 | 120 | b | N | S-1_F1insN | NFPM (SEQ ID NO: 304) . . . | hCXCL11.0031-G1T4k.one//VHn-G1T4h.one.H435R |
| hCXCL11.0032 | 121 | b | P | S-1_F1insP | PFPM (SEQ ID NO: 305) . . . | hCXCL11.0032-G1T4k.one//VHn-G1T4h.one.H435R |
| hCXCL11.0033 | 122 | b | Q | S-1_F1insQ | QFPM (SEQ ID NO: 306) . . . | hCXCL11.0033-G1T4k.one//VHn-G1T4h.one.H435R |
| hCXCL11.0034 | 123 | b | R | S-1_F1insR | RFPM (SEQ ID NO: 307) . . . | hCXCL11.0034-G1T4k.one//VHn-G1T4h.one.H435R |
| hCXCL11.0035 | 124 | b | S | S-1_F1insS | SFPM (SEQ ID NO: 308) . . . | hCXCL11.0035-G1T4k.one//VHn-G1T4h.one.H435R |
| hCXCL11.0036 | 125 | b | T | S-1_F1insT | TFPM (SEQ ID NO: 309) . . . | hCXCL11.0036-G1T4k.one//VHn-G1T4h.one.H435R |
| hCXCL11.0037 | 126 | b | V | S-1_F1insV | VFPM (SEQ ID NO: 310) . . . | hCXCL11.0037-G1T4k.one//VHn-G1T4h.one.H435R |
| hCXCL11.0038 | 127 | b | W | S-1_F1insW | WFPM(SEQ ID NO: 311) . . . | hCXCL11.0038-G1T4k.one//VHn-G1T4h.one.H435R |
| hCXCL11.0039 | 128 | b | Y | S-1_F1insY | YFPM (SEQ ID NO: 312) . . . | hCXCL11.0039-G1T4k.one//VHn-G1T4h.one.H435R |
| hCXCL11.0040 | 129 | c | A | F1_P2insA | FAPM (SEQ ID NO: 313) . . . | hCXCL11.0040-G1T4k.one//VHn-G1T4h.one.H435R |
| hCXCL11.0041 | 130 | c | D | F1_P2insD | FDPM (SEQ ID NO: 314) . . . | hCXCL11.0041-G1T4k.one//VHn-G1T4h.one.H435R |
| hCXCL11.0042 | 131 | c | E | F1_P2insE | FEPM (SEQ ID NO: 315) . . . | hCXCL11.0042-G1T4k.one//VHn-G1T4h.one.H435R |
| hCXCL11.0043 | 132 | c | F | F1_P2insF | FFPM (SEQ ID NO: 316) . . . | hCXCL11.0043-G1T4k.one//VHn-G1T4h.one.H435R |
| hCXCL11.0044 | 133 | c | G | F1_P2insG | FGPM (SEQ ID NO: 317) . . . | hCXCL11.0044-G1T4k.one//VHn-G1T4h.one.H435R |
| hCXCL11.0045 | 134 | c | H | F1_P2insH | FHPM (SEQ ID NO: 318) . . . | hCXCL11.0045-G1T4k.one//VHn-G1T4h.one.H435R |
| hCXCL11.0046 | 135 | c | I | F1_P2insI | FIPM (SEQ ID NO: 319) . . . | hCXCL11.0046-G1T4k.one//VHn-G1T4h.one.H435R |

TABLE 6-continued

| Sequence Name | SEQ ID NO | Modification pattern | Modified, inserted amino acid residue | Modification | N-terminal sequence | Corresponding hCXCL11 variant Fc fusion |
|---|---|---|---|---|---|---|
| hCXCL11.0047 | 136 | c | K | F1_P2insK | FKPM (SEQ ID NO: 320) . . . | hCXCL11.0047-G1T4k.one//VHn-G1T4h.one.H435R |
| hCXCL11.0048 | 137 | c | L | F1_P2insL | FLPM (SEQ ID NO: 321) . . . | hCXCL11.0048-G1T4k.one//VHn-G1T4h.one.H435R |
| hCXCL11.0049 | 138 | c | M | F1_P2insM | FMPM (SEQ ID NO: 322) . . . | hCXCL11.0049-G1T4k.one//VHn-G1T4h.one.H435R |
| hCXCL11.0050 | 139 | c | N | F1_P2insN | FNPM (SEQ ID NO: 323) . . . | hCXCL11.0050-G1T4k.one//VHn-G1T4h.one.H435R |
| hCXCL11.0051 | 140 | c | P | F1_P2insP | FPPM (SEQ ID NO: 324) . . . | hCXCL11.0051-G1T4k.one//VHn-G1T4h.one.H435R |
| hCXCL11.0052 | 141 | c | Q | F1_P2insQ | FQPM (SEQ ID NO: 325) . . . | hCXCL11.0052-G1T4k.one//VHn-G1T4h.one.H435R |
| hCXCL11.0053 | 142 | c | R | F1_P2insR | FRPM (SEQ ID NO: 326) . . . | hCXCL11.0053-G1T4k.one//VHn-G1T4h.one.H435R |
| hCXCL11.0054 | 143 | c | S | F1_P2insS | FSPM (SEQ ID NO: 327) . . . | hCXCL11.0054-G1T4k.one//VHn-G1T4h.one.H435R |
| hCXCL11.0055 | 144 | c | T | F1_P2insT | FTPM (SEQ ID NO: 328) . . . | hCXCL11.0055-G1T4k.one//VHn-G1T4h.one.H435R |
| hCXCL11.0056 | 145 | c | V | F1_P2insV | FVPM (SEQ ID NO: 329) . . . | hCXCL11.0056-G1T4k.one//VHn-G1T4h.one.H435R |
| hCXCL11.0057 | 146 | c | W | F1_P2insW | FWPM(SEQ ID NO: 330) . . . | hCXCL11.0057-G1T4k.one//VHn-G1T4h.one.H435R |
| hCXCL11.0058 | 147 | c | Y | F1_P2insY | FYPM (SEQ ID NO: 331) . . . | hCXCL11.0058-G1T4k.one//VHn-G1T4h.one.H435R |

Example 5. Construction of Human CXCL10-Human CXCL11 Chimeric Protein (hITIP) and hITIP Fe Fusions Human CXCL10-human CXCL11 chimeric protein (hITIP, SEQ ID NO: 63), in which the 1st to 24th amino acid residues of hCXCL11 (SEQ ID NO: 61) and the 25th to 77th amino acid residues of an hCXCL10 variant (SEQ ID NO: 1) are bound, and hITIP variants in which amino acid modifications were introduced into and around the dipeptidyl peptidase IV (DPPIV) recognition/cleavage site of hITIP were constructed (the amino acid modification positions in and around the DPPIV recognition/cleavage site is shown in FIG. 4B, and the names, sequences, and such of the designed hITIP variants are shown in Table 7).

In order to facilitate the purification of the various hITIP variants, hITIP variant Fc fusions were constructed by fusing the hITIP variants with the human IgG1 antibody Fc domain. A schematic diagram of this is shown in FIG. 4A.

hITIP variant Fc fusions, in which the above hITIP variants are fused with the human IgG1 antibody (hIgG1) Fc domain variant G1T4k.one//VHn-G1T4h.one.H435R (G1T4k.one (SEQ ID NO: 58), VHn-G1T4h.one.H435R (SEQ ID NO: 59)), were prepared. Specifically, expression vectors encoding genes of peptide chains in which the C-terminus of each hITIP variant and the N-terminus of G1T4k.one in G1T4k.one//VHn-G1T4h.one.H435R are linked were prepared by a method known to those skilled in the art. These peptide chains were combined with VHn-G1T4h.one.H435R, and hITIP variant Fc fusions, in which one hITIP variant is bound to an hIgG1 Fc domain variant, were expressed by transient expression using Expi 293 (Life Technologies) by a method known to those skilled in the art and purified by a method known to those skilled in the art using protein A.

The Fc domain variant used in this study has a mutation for increasing the yield of Fc heteroassociated molecules and a mutation that suppresses FcγR binding introduced therein.

TABLE 7

| Sequence Name | SEQ ID NO | Modification pattern | Modified, inserted amino acid residue | Modification | N-terminal sequence | Corresponding hITIP variant Fc fusion |
|---|---|---|---|---|---|---|
| hITIP | 63 | | | | FPMF (SEQ ID NO: 332) . . . | hITIP-G1T4k.one//VHn-G1T4h.one.H435R |
| hITIP0003 | 149 | a | A | P2A | FAMF (SEQ ID NO: 333) . . . | hITIP0003-G1T4k.one//VHn-G1T4h.one.H435R |
| hITIP0004 | 150 | a | D | P2D | FDMF (SEQ ID NO: 334) . . . | hITIP0004-G1T4k.one//VHn-G1T4h.one.H435R |
| hITIP0005 | 151 | a | E | P2E | FEMF (SEQ ID NO: 335) . . . | hITIP0005-G1T4k.one//VHn-G1T4h.one.H435R |
| hITIP0006 | 152 | a | F | P2F | FFMF (SEQ ID NO: 336) . . . | hITIP0006-G1T4k.one//VHn-G1T4h.one.H435R |
| hITIP0007 | 153 | a | G | P2G | FGMF (SEQ ID NO: 337) . . . | hITIP0007-G1T4k.one//VHn-G1T4h.one.H435R |
| hITIP0008 | 154 | a | H | P2H | FHMF (SEQ ID NO: 338) . . . | hITIP0008-G1T4k.one//VHn-G1T4h.one.H435R |
| hITIP0009 | 155 | a | I | P2I | FIMF (SEQ ID NO: 339) . . . | hITIP0009-G1T4k.one//VHn-G1T4h.one.H435R |
| hITIP0010 | 156 | a | K | P2K | FKMF (SEQ ID NO: 340) . . . | hITIP0010-G1T4k.one//VHn-G1T4h.one.H435R |
| hITIP0011 | 157 | a | L | P2L | FLMF (SEQ ID NO: 341) . . . | hITIP0011-G1T4k.one//VHn-G1T4h.one.H435R |
| hITIP0012 | 158 | a | M | P2M | FMMF (SEQ ID NO: 342) . . . | hITIP0012-G1T4k.one//VHn-G1T4h.one.H435R |
| hITIP0013 | 159 | a | N | P2N | FNMF (SEQ ID NO: 343) . . . | hITIP0013-G1T4k.one//VHn-G1T4h.one.H435R |
| hITIP0014 | 160 | a | Q | P2Q | FQMF (SEQ ID NO: 344) . . . | hITIP0014-G1T4k.one//VHn-G1T4h.one.H435R |
| hITIP0015 | 161 | a | R | P2R | FRMF (SEQ ID NO: 345) . . . | hITIP0015-G1T4k.one//VHn-G1T4h.one.H435R |
| hITIP0016 | 162 | a | S | P2S | FSMF (SEQ ID NO: 346) . . . | hITIP0016-G1T4k.one//VHn-G1T4h.one.H435R |
| hITIP0017 | 163 | a | T | P2T | FTMF (SEQ ID NO: 347) . . . | hITIP0017-G1T4k.one//VHn-G1T4h.one.H435R |
| hITIP0018 | 164 | a | V | P2V | FVMF (SEQ ID NO: 348) . . . | hITIP0018-G1T4k.one//VHn-G1T4h.one.H435R |
| hITIP0019 | 165 | a | W | P2W | FWMF (SEQ ID NO: 349) . . . | hITIP0019-G1T4k.one//VHn-G1T4h.one.H435R |
| hITIP0020 | 166 | a | Y | P2Y | FYMF (SEQ ID NO: 350) . . . | hITIP0020-G1T4k.one//VHn-G1T4h.one.H435R |
| hITIP0021 | 167 | b | A | S-1_F1insA | AFPM (SEQ ID NO: 351) . . . | hITIP0021-G1T4k.one//VHn-G1T4h.one.H435R |
| hITIP0022 | 168 | b | D | S-1_F1insD | DFPM (SEQ ID NO: 352) . . . | hITIP0022-G1T4k.one//VHn-G1T4h.one.H435R |
| hITIP0023 | 169 | b | E | S-1_F1insE | EFPM (SEQ ID NO: 353) . . . | hITIP0023-G1T4k.one//VHn-G1T4h.one.H435R |
| hITIP0024 | 170 | b | F | S-1_F1insF | FFPM (SEQ ID NO: 354) . . . | hITIP0024-G1T4k.one//VHn-G1T4h.one.H435R |
| hITIP0025 | 171 | b | G | S-1_F1insG | GFPM (SEQ ID NO: 355) . . . | hITIP0025-G1T4k.one//VHn-G1T4h.one.H435R |
| hITIP0026 | 172 | b | H | S-1_F1insH | HFPM (SEQ ID NO: 356) . . . | hITIP0026-G1T4k.one//VHn-G1T4h.one.H435R |

TABLE 7-continued

| Sequence Name | SEQ ID NO | Modification pattern | Modified, inserted amino acid residue | Modification | N-terminal sequence | Corresponding hITIP variant Fc fusion |
|---|---|---|---|---|---|---|
| hITIP0027 | 173 | b | I | S-1_F1insI | IFPM (SEQ ID NO: 357) . . . | hITIP0027-G1T4k.one//VHn-G1T4h.one.H435R |
| hITIP0028 | 174 | b | K | S-1_F1insK | KFPM (SEQ ID NO: 358) . . . | hITIP0028-G1T4k.one//VHn-G1T4h.one.H435R |
| hITIP0029 | 175 | b | L | S-1_F1insL | LFPM (SEQ ID NO: 359) . . . | hITIP0029-G1T4k.one//VHn-G1T4h.one.H435R |
| hITIP0030 | 176 | b | M | S-1_F1insM | MFPM (SEQ ID NO: 360) . . . | hITIP0030-G1T4k.one//VHn-G1T4h.one.H435R |
| hITIP0031 | 177 | b | N | S-1_F1insN | NFPM (SEQ ID NO: 361) . . . | hITIP0031-G1T4k.one//VHn-G1T4h.one.H435R |
| hITIP0032 | 178 | b | P | S-1_F1insP | PFPM (SEQ ID NO: 362) . . . | hITIP0032-G1T4k.one//VHn-G1T4h.one.H435R |
| hITIP0033 | 179 | b | Q | S-1_F1insQ | QFPM (SEQ ID NO: 363) . . . | hITIP0033-G1T4k.one//VHn-G1T4h.one.H435R |
| hITIP0034 | 180 | b | R | S-1_F1insR | RFPM (SEQ ID NO: 364) . . . | hITIP0034-G1T4k.one//VHn-G1T4h.one.H435R |
| hITIP0035 | 181 | b | S | S-1_F1insS | SFPM (SEQ ID NO: 365) . . . | hITIP0035-G1T4k.one//VHn-G1T4h.one.H435R |
| hITIP0036 | 182 | b | T | S-1_F1insT | TFPM (SEQ ID NO: 366) . . . | hITIP0036-G1T4k.one//VHn-G1T4h.one.H435R |
| hITIP0037 | 183 | b | V | S-1_F1insV | VFPM (SEQ ID NO: 367) . . . | hITIP0037-G1T4k.one//VHn-G1T4h.one.H435R |
| hITIP0038 | 184 | b | W | S-1_F1insW | WFPM (SEQ ID NO: 368) . . . | hITIP0038-G1T4k.one//VHn-G1T4h.one.H435R |
| hITIP0039 | 185 | b | Y | S-1_F1insY | YFPM (SEQ ID NO: 369) . . . | hITIP0039-G1T4k.one//VHn-G1T4h.one.H435R |
| hITIP0040 | 186 | c | A | F1_P2insA | FAPM (SEQ ID NO: 370) . . . | hITIP0040-G1T4k.one//VHn-G1T4h.one.H435R |
| hITIP0041 | 187 | c | D | F1_P2insD | FDPM (SEQ ID NO: 371) . . . | hITIP0041-G1T4k.one//VHn-G1T4h.one.H435R |
| hITIP0042 | 188 | c | E | F1_P2insE | FEPM (SEQ ID NO: 372) . . . | hITIP0042-G1T4k.one//VHn-G1T4h.one.H435R |
| hITIP0043 | 189 | c | F | F1_P2insF | FFPM (SEQ ID NO: 373) . . . | hITIP0043-G1T4k.one//VHn-G1T4h.one.H435R |
| hITIP0044 | 190 | c | G | F1_P2insG | FGPM (SEQ ID NO: 374) . . . | hITIP0044-G1T4k.one//VHn-G1T4h.one.H435R |
| hITIP0045 | 191 | c | H | F1_P2insH | FHPM (SEQ ID NO: 375) . . . | hITIP0045-G1T4k.one//VHn-G1T4h.one.H435R |
| hITIP0046 | 192 | c | I | F1_P2insI | FIPM (SEQ ID NO: 376) . . . | hITIP0046-G1T4k.one//VHn-G1T4h.one.H435R |
| hITIP0047 | 193 | c | K | F1_P2insK | FKPM (SEQ ID NO: 377) . . . | hITIP0047-G1T4k.one//VHn-G1T4h.one.H435R |
| hITIP0048 | 194 | c | L | F1_P2insL | FLPM (SEQ ID NO: 378) . . . | hITIP0048-G1T4k.one//VHn-G1T4h.one.H435R |
| hITIP0049 | 195 | c | M | F1_P2insM | FMPM (SEQ ID NO: 379) . . . | hITIP0049-G1T4k.one//VHn-G1T4h.one.H435R |
| hITIP0050 | 196 | c | N | F1_P2insN | FNPM (SEQ ID NO: 380) . . . | hITIP0050-G1T4k.one//VHn-G1T4h.one.H435R |
| hITIP0051 | 197 | c | P | F1_P2insP | FPPM (SEQ ID NO: 381) . . . | hITIP0051-G1T4k.one//VHn-G1T4h.one.H435R |
| hITIP0052 | 198 | c | Q | F1_P2insQ | FQPM (SEQ ID NO: 382) . . . | hITIP0052-G1T4k.one//VHn-G1T4h.one.H435R |
| hITIP0053 | 199 | c | R | F1_P2insR | FRPM (SEQ ID NO: 383) . . . | hITIP0053-G1T4k.one//VHn-G1T4h.one.H435R |
| hITIP0054 | 200 | c | S | F1_P2insS | FSPM (SEQ ID NO: 384) . . . | hITIP0054-G1T4k.one//VHn-G1T4h.one.H435R |
| hITIP0055 | 201 | c | T | F1_P2insT | FTPM (SEQ ID NO: 385) . . . | hITIP0055-G1T4k.one//VHn-G1T4h.one.H435R |
| hITIP0056 | 202 | c | V | F1_P2insV | FVPM (SEQ ID NO: 386) . . . | hITIP0056-G1T4k.one//VHn-G1T4h.one.H435R |
| hITIP0057 | 203 | c | W | F1_P2insW | FWPM (SEQ ID NO: 387) . . . | hITIP0057-G1T4k.one//VHn-G1T4h.one.H435R |
| hITIP0058 | 204 | c | Y | F1_P2insY | FYPM (SEQ ID NO: 388) . . . | hITIP0058-G1T4k.one//VHn-G1T4h.one.H435R |

Some of the hCXCL10 variants for which cleavage of the two N-terminal residues by hDPPIV was not observed in Example 3 were evaluated as to whether they induce migration of cells expressing CXCR3 (cell migration-inducing activity) even after DPPIV treatment.

Human-derived dipeptidyl peptidase IV (human DPPIV, hDPPIV) (Biolegend, 764102) was used as the protease. The hCXCL10 variants at a final concentration of 12 μM were treated with hDPPIV at a final concentration of 400 nM in PBS under conditions of 37° C. for 1 hour. It was evaluated whether the DPPIV-treated hCXCL10 variants induce migration of cells expressing CXCR3 (cell migration-inducing activity). Cell migration-inducing activity was evaluated using Ba/F3 transfectant cells expressing mouse CXCR3 (mCXCR3) (hereinafter referred to as BaF3/mCXCR3) and HTS Transwell™_96 Permeable Supports with 5.0 μm Pore Polycarbonate Membrane (Cat. 3387, Coming).

The following hCXCL10 variants treated with DPPIV were used as analytes: hCXCL10R75A, hCXCL10R75A.0041, hCXCL10R75A.0042, and hCXCL10R75A.0028.

hCXCL10R75A, hCXCL10R75A.0041, hCXCL10R75A.0042 and hCXCL10R75A.0028 were expressed by transient expression using Expi293 (Life Technologies) by a method known to those skilled in the art, and purification was performed by a method known to those skilled in the art using heparin sepharose (HiTrap Heparin HP Column GE Healthcare) and gel filtration (HiLoadSuperdex75pg GE Healthcare).

After adjusting the final concentration in the solutions of each analyte to be analyzed so as to be from 1 nM to 600 nM, 235 μL of each solution was transferred to the lower chamber. Then, BaF3/mCXCR3 cells were seeded into the upper chamber at 75 μL/well so as to be 2.0×10⁵ cells/well, and the reaction was carried out for 6 hours. The reaction was carried out under the conditions of 5% carbon dioxide and 37° C. After 6 hours of reaction, 100 μL of the solution in the lower chamber was transferred to OptiPlate-96 (Cat. 6005299, PerkinElmer) and 100 μL of CellTiter-Glo™ Luminescent Cell Viability Assay solution (Cat. G7571, Promega) was added. After reacting at room temperature for 10 minutes, the luminescence value was measured with a 2104 EnVision™ multi-label reader (PerkinElmer) to evaluate the level of migration of cells into the lower chamber.

The luminescence intensity reflects the amount of cells that migrated into the lower chamber. The cell migration-inducing activity of hCXCL10 variants was compared.

Figure 5:
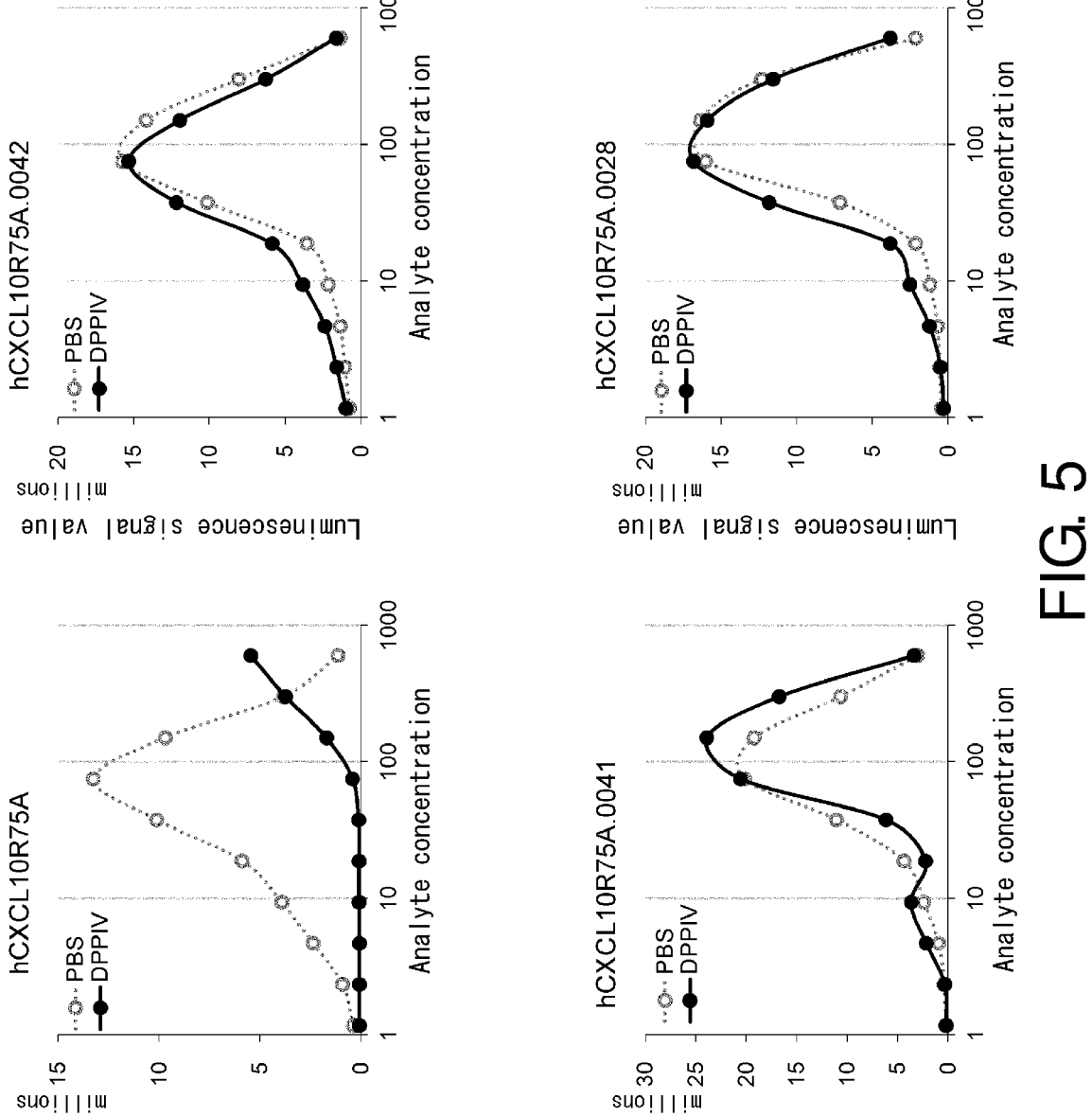
FIG. 5 shows a comparison of cell migration-inducing activities of hCXCL10 variants before and after DPPIV treatment.

Comparison of the cell migration-inducing activity of the hCXCL10 variants was performed after 6 hours of reaction, and the results are shown in FIG. 5 and Table 8. DPPIV-treated hCXCL10R75A showed significantly reduced cell migration-inducing activity in the range of 1 nM to 100 nM compared to DPPIV-untreated hCXCL10R75A. On the other hand, DPPIV-treated hCXCL10R75A.0041, hCXCL10R75A.0042 and hCXCL10R75A.0028 showed equivalent cell migration-inducing activity at each concentration as compared with the respective DPPIV-untreated variants at the same concentrations. From this, it was shown that these hCXCL10 variants have sufficient activity even after treatment with DPPIV.

TABLE 8

| Analyte name | DPPIV | Analyte concentration | Luminesce value |
|---|---|---|---|
| hCXCL10R75A | – | 1 nM | 384286 |
| | | 2 nM | 909013 |
| | | 5 nM | 2360051 |
| | | 9 nM | 3925789 |
| | | 19 nM | 5869969 |
| | | 38 nM | 10112159 |
| | | 75 nM | 13262058 |
| | | 150 nM | 9680211 |
| | | 300 nM | 3833908 |
| | | 600 nM | 1126521 |
| hCXCL10R75A.0041 | – | 1 nM | 170183 |
| | | 2 nM | 386200 |
| | | 5 nM | 918247 |
| | | 9 nM | 2393740 |
| | | 19 nM | 4359804 |
| | | 38 nM | 11026260 |
| | | 75 nM | 20180488 |
| | | 150 nM | 19195381 |
| | | 300 nM | 10637776 |
| | | 600 nM | 2996213 |
| hCXCL10R75A.0042 | – | 1 nM | 749550 |
| | | 2 nM | 1053748 |
| | | 5 nM | 1360707 |
| | | 9 nM | 2158386 |
| | | 19 nM | 3573993 |
| | | 38 nM | 10150885 |
| | | 75 nM | 15774662 |
| | | 150 nM | 14178170 |
| | | 300 nM | 8071032 |
| | | 600 nM | 1378453 |
| hCXCL10R75A.0028 | – | 1 nM | 440800 |
| | | 2 nM | 550618 |
| | | 5 nM | 688390 |
| | | 9 nM | 1199380 |
| | | 19 nM | 2142287 |
| | | 38 nM | 7149151 |
| | | 75 nM | 16018027 |
| | | 150 nM | 16362897 |
| | | 300 nM | 12306411 |
| | | 600 nM | 2138988 |
| hCXCL10R75A | + | 1 nM | 78153 |
| | | 2 nM | 73792 |
| | | 5 nM | 74832 |
| | | 9 nM | 84037 |
| | | 19 nM | 82833 |
| | | 38 nM | 107446 |
| | | 75 nM | 410388 |
| | | 150 nM | 1698455 |
| | | 300 nM | 3724658 |
| | | 600 nM | 5453426 |
| hCXCL10R75A.0041 | + | 1 nM | 201203 |
| | | 2 nM | 306204 |
| | | 5 nM | 2158532 |
| | | 9 nM | 3647332 |
| | | 19 nM | 2236899 |
| | | 38 nM | 6118440 |
| | | 75 nM | 20570790 |
| | | 150 nM | 23888168 |
| | | 300 nM | 16714552 |
| | | 600 nM | 3369186 |
| hCXCL10R75A.0042 | + | 1 nM | 984135 |
| | | 2 nM | 1606332 |
| | | 5 nM | 2383033 |
| | | 9 nM | 3822807 |
| | | 19 nM | 5869317 |
| | | 38 nM | 12182978 |
| | | 75 nM | 15343371 |
| | | 150 nM | 11965440 |
| | | 300 nM | 6283371 |
| | | 600 nM | 1624949 |
| hCXCL10R75A.0028 | + | 1 nM | 288701 |
| | | 2 nM | 497223 |
| | | 5 nM | 1222920 |
| | | 9 nM | 2507969 |
| | | 19 nM | 3806319 |
| | | 38 nM | 11819096 |
| | | 75 nM | 16814895 |

TABLE 8-continued

| Analyte name | DPPIV | Analyte concentration | Luminesce value |
|---|---|---|---|
| | | 150 nM | 15895458 |
| | | 300 nM | 11558694 |
| | | 600 nM | 3804462 |
| Cell only | – | 0 nM | 99402 |

Example 7. Evaluation of the Cell Migration-Inducing Activity of hCXCL11 Variant Fe Fusions It was evaluated whether the hCXCL11 variant Fc fusions prepared in Example 4 induce migration of cells expressing CXCR3 (cell migration-inducing activity). Cell migration-inducing activity was evaluated using Ba/F3 transfectant cells expressing human CXCR3 (hCXCR3) (hereinafter referred to as BaF3/hCXCR3) and HTS Transwell™_96 Permeable Supports with 5.0 μm Pore Polycarbonate Membrane (Cat. 3387, Coming).

The following hCXCL11 variant Fe fusions prepared in Example 4 were used as analytes:

hCXCL11-G1T4k.one//VHn-G1T4h.one.H435R,
hCXCL11.0003-G1T4k.one//VHn-G1T4h.one.H435R,
hCXCL11.0004-G1T4k.one//VHn-G1T4h.one.H435R,
hCXCL11.0005-G1T4k.one//VHn-G1T4h.one.H435R,
hCXCL11.0006-G1T4k.one//VHn-G1T4h.one.H435R,
hCXCL11.0007-G1T4k.one//VHn-G1T4h.one.H435R,
hCXCL 11.0008-G1T4k.one//VHn-G1T4h.one.H435R,
hCXCL11.0009-G1T4k.one//VHn-G1T4h.one.H435R,
hCXCL 11.0010-G1T4k.one//VHn-G1T4h.one.H435R,
hCXCL 11.0011-G1T4k.one//VHn-G1T4h.one.H435R,
hCXCL 11.0012-G1T4k.one//VHn-G1T4h.one.H435R,
hCXCL 11.0013-G1T4k.one//VHn-G1T4h.one.H435R,
hCXCL 11.0014-G1T4k.one//VHn-G1T4h.one.H435R,
hCXCL 11.0015-G1T4k.one//VHn-G1T4h.one.H435R,
hCXCL 11.0016-G1T4k.one//VHn-G1T4h.one.H435R,
hCXCL 11.0017-G1T4k.one//VHn-G1T4h.one.H435R,
hCXCL 11.0018-G1T4k.one//VHn-G1T4h.one.H435R,
hCXCL 11.0019-G1T4k.one//VHn-G1T4h.one.H435R,
hCXCL11.0020-G1T4k.one//VHn-G1T4h.one.H435R,
hCXCL 11.0021-G1T4k.one//VHn-G1T4h.one.H435R,
hCXCL11.0022-G1T4k.one//VHn-G1T4h.one.H435R,
hCXCL11.0023-G1T4k.one//VHn-G1T4h.one.H435R,
hCXCL11.0024-G1T4k.one//VHn-G1T4h.one.H435R,
hCXCL11.0025-G1T4k.one//VHn-G1T4h.one.H435R,
hCXCL11.0026-G1T4k.one//VHn-G1T4h.one.H435R,
hCXCL11.0027-G1T4k.one//VHn-G1T4h.one.H435R,
hCXCL 11.0028-G1T4k.one//VHn-G1T4h.one.H435R,
hCXCL11.0029-G1T4k.one//VHn-G1T4h.one.H435R,
hCXCL 11.0030-G1T4k.one//VHn-G1T4h.one.H435R,
hCXCL 11.0031-G1T4k.one//VHn-G1T4h.one.H435R,
hCXCL 11.0032-G1T4k.one//VHn-G1T4h.one.H435R,
hCXCL 11.0033-G1T4k.one//VHn-G1T4h.one.H435R,
hCXCL 11.0034-G1T4k.one//VHn-G1T4h.one.H435R,
hCXCL 11.0035-G1T4k.one//VHn-G1T4h.one.H435R,
hCXCL 11.0036-G1T4k.one//VHn-G1T4h.one.H435R,
hCXCL 11.0037-G1T4k.one//VHn-G1T4h.one.H435R,
hCXCL 11.0038-G1T4k.one//VHn-G1T4h.one.H435R,
hCXCL 11.0039-G1T4k.one//VHn-G1T4h.one.H435R,
hCXCL11.0040-G1T4k.one//VHn-G1T4h.one.H435R,
hCXCL 11.0041-G1T4k.one//VHn-G1T4h.one.H435R,
hCXCL11.0042-G1T4k.one//VHn-G1T4h.one.H435R,
hCXCL11.0044-G1T4k.one//VHn-G1T4h.one.H435R,
hCXCL11.0045-G1T4k.one//VHn-G1T4h.one.H435R,

53 hCXCL11.0046-G1T4k.one//VHn-G1T4h.one.H435R,
hCXCL11.0047-G1T4k.one//VHn-G1T4h.one.H435R,
hCXCL 11.0048-G1T4k.one//VHn-G1T4h.one.H435R,
hCXCL11.0049-G1T4k.one//VHn-G1T4h.one.H435R,
hCXCL 11.0050-G1T4k.one//VHn-G1T4h.one.H435R,
hCXCL 11.0051-G1T4k.one//VHn-G1T4h.one.H435R,
hCXCL 11.0052-G1T4k.one//VHn-G1T4h.one.H435R,
hCXCL 11.0053-G1T4k.one//VHn-G1T4h.one.H435R,
hCXCL 11.0054-G1T4k.one//VHn-G1T4h.one.H435R,
hCXCL 11.0055-G1T4k.one//VHn-G1T4h.one.H435R,
hCXCL 11.0056-G1T4k.one//VHn-G1T4h.one.H435R,
hCXCL11.0057-G1T4k.one//VHn-G1T4h.one.H435R,
    and
hCXCL 11.0058-G1T4k.one//VHn-G1T4h.one.H435R.

After adjusting the final concentration in the solution of each analyte to be analyzed to be 33 nM, 100 nM, and 300 nM, 235 μL of each solution was transferred to the lower chamber. Then, BaF3/hCXCR3 cells were seeded into the upper chamber at 75 μL/well so as to be 2.0×10⁵ cells/well, and the reaction was carried out for 18 hours under the conditions of 5% carbon dioxide and 37° C. After reacting for 18 hours, 100 μL of the solution in the lower chamber was transferred to OptiPlate-96 (Cat. 6005299, PerkinElmer), and 100 μL of CellTiter-Glo™ Luminescent Cell Viability Assay solution (Cat. G7571, Promega) was added. After reacting at room temperature for 10 minutes, the luminescence value was measured with a 2104 EnVision™ multi-label reader (PerkinElmer) to evaluate the level of migration of cells into the lower chamber.

The luminescence intensity reflects the amount of cells that migrated into the lower chamber. The cell migration-inducing activities of hCXCL11-G1T4k.one//VHn-G1T4h.one.H435R and of the other hCXCL11 variant Fc fusions were compared.

Comparison of the cell migration-inducing activities of hCXCL11-G1T4k.one//VHn-G1T4h.one.H435R and of the other hCXCL11 variant Fc fusions was performed after 18 hours of reaction, and the results are shown in FIG. 6 (FIG. 6-1, FIG. 6-2, and FIG. 6-3) and Table 9. Compared to hCXCL11-G1T4k.one//VHn-G1T4h.one.H435R, hCXCL11.0003-G1T4k.one//VHn-G1T4h.one.H435R,
hCXCL11.0004-G1T4k.one//VHn-G1T4h.one.H435R,
hCXCL11.0005-G1T4k.one//VHn-G1T4h.one.H435R,
hCXCL11.0007-G1T4k.one//VHn-G1T4h.one.H435R,

54 hCXCL 11.0008-G1T4k.one//VHn-G1T4h.one.H435R,
hCXCL 11.0013-G1T4k.one//VHn-G1T4h.one.H435R,
hCXCL 11.0014-G1T4k.one//VHn-G1T4h.one.H435R,
hCXCL 11.0015-G1T4k.one//VHn-G1T4h.one.H435R,
hCXCL 11.0016-G1T4k.one//VHn-G1T4h.one.H435R,
hCXCL 11.0017-G1T4k.one//VHn-G1T4h.one.H435R,
hCXCL11.0020-G1T4k.one//VHn-G1T4h.one.H435R,
hCXCL 11.0021-G1T4k.one//VHn-G1T4h.one.H435R,
hCXCL11.0022-G1T4k.one//VHn-G1T4h.one.H435R,
hCXCL11.0023-G1T4k.one//VHn-G1T4h.one.H435R,
hCXCL11.0024-G1T4k.one//VHn-G1T4h.one.H435R,
hCXCL11.0025-G1T4k.one//VHn-G1T4h.one.H435R,
hCXCL11.0026-G1T4k.one//VHn-G1T4h.one.H435R,
hCXCL11.0027-G1T4k.one//VHn-G1T4h.one.H435R,
hCXCL 11.0028-G1T4k.one//VHn-G1T4h.one.H435R,
hCXCL11.0029-G1T4k.one//VHn-G1T4h.one.H435R,
hCXCL 11.0030-G1T4k.one//VHn-G1T4h.one.H435R,
hCXCL 11.0031-G1T4k.one//VHn-G1T4h.one.H435R,
hCXCL 11.0032-G1T4k.one//VHn-G1T4h.one.H435R,
hCXCL 11.0033-G1T4k.one//VHn-G1T4h.one.H435R,
hCXCL 11.0035-G1T4k.one//VHn-G1T4h.one.H435R,
hCXCL 11.0036-G1T4k.one//VHn-G1T4h.one.H435R,
hCXCL 11.0037-G1T4k.one//VHn-G1T4h.one.H435R,
hCXCL 11.0038-G1T4k.one//VHn-G1T4h.one.H435R,
hCXCL 11.0039-G1T4k.one//VHn-G1T4h.one.H435R,
hCXCL11.0040-G1T4k.one//VHn-G1T4h.one.H435R,
hCXCL 11.0041-G1T4k.one//VHn-G1T4h.one.H435R,
hCXCL11.0042-G1T4k.one//VHn-G1T4h.one.H435R,
hCXCL11.0044-G1T4k.one//VHn-G1T4h.one.H435R,
hCXCL11.0045-G1T4k.one//VHn-G1T4h.one.H435R,
hCXCL 11.0048-G1T4k.one//VHn-G1T4h.one.H435R,
hCXCL11.0049-G1T4k.one//VHn-G1T4h.one.H435R,
hCXCL 11.0050-G1T4k.one//VHn-G1T4h.one.H435R,
hCXCL 11.0051-G1T4k.one//VHn-G1T4h.one.H435R,
hCXCL 11.0052-G1T4k.one//VHn-G1T4h.one.H435R,
hCXCL11.0054-G1T4k.one//VHn-G1T4h.one.H435R,
    and
hCXCL   11.0055-G1T4k.one//VHn-G1T4h.one.H435R retained, at each of the concentrations of 33 nM, 100 nM, and 300 nM, 25% or more of the cell migration-inducing activity of hCXCL11-G1T4k.one//VHn-G1T4h.one.H435R at the same concentration. From this, it was shown that the hCXCL11 variants contained in these hCXCL11 variant Fc fusions have sufficient activity.

TABLE 9

| Analyte name | Analyte concentration | Luminescence calue | Activity retention rate* |
|---|---|---|---|
| hCXCL11-G1T4k.one//VHn-G1T4h.one.H435R | 33 nM | 7680512 | |
| | 100 nM | 16701834 | |
| | 300 nM | 12424624 | |
| hCXCL11.0003-G1T4k.one//VHn-G1T4h.one.H435R | 33 nM | 3761418 | 49% |
| | 100 nM | 11666034 | 70% |
| | 300 nM | 11205876 | 90% |
| hCXCL11.0004-G1T4k.one//VHn-G1T4h.one.H435R | 33 nM | 3145358 | 41% |
| | 100 nM | 9439905 | 57% |
| | 300 nM | 5240261 | 42% |
| hCXCL11.0005-G1T4k.one//VHn-G1T4h.one.H435R | 33 nM | 3107148 | 40% |
| | 100 nM | 9594341 | 57% |
| | 300 nM | 6032127 | 49% |
| hCXCL11.0006-G1T4k.one//VHn-G1T4h.one.H435R | 33 nM | 325725 | 4% |
| | 100 nM | 4545172 | 27% |
| | 300 nM | 9793195 | 79% |
| hCXCL11.0007-G1T4k.one//VHn-G1T4h.one.H435R | 33 nM | 3474336 | 45% |
| | 100 nM | 10168584 | 61% |
| | 300 nM | 9705698 | 78% |

TABLE 9-continued

| Analyte name | Analyte concentration | Luminescence calue | Activity retention rate* |
|---|---|---|---|
| hCXCL11.0008-G1T4k.one//VHn-G1T4h.one.H435R | 33 nM | 3403401 | 44% |
| | 100 nM | 12154445 | 73% |
| | 300 nM | 13423586 | 108% |
| hCXCL11.0009-G1T4k.one//VHn-G1T4h.one.H435R | 33 nM | 966221 | 13% |
| | 100 nM | 6792509 | 41% |
| | 300 nM | 13486638 | 109% |
| hCXCL11.0010-G1T4k.one//VHn-G1T4h.one.H435R | 33 nM | 524466 | 7% |
| | 100 nM | 4931525 | 30% |
| | 300 nM | 7782022 | 63% |
| hCXCL11.0011-G1T4k.one//VHn-G1T4h.one.H435R | 33 nM | 261903 | 3% |
| | 100 nM | 4015832 | 24% |
| | 300 nM | 9604642 | 77% |
| hCXCL11.0012-G1T4k.one//VHn-G1T4h.one.H435R | 33 nM | 1333862 | 17% |
| | 100 nM | 7602984 | 46% |
| | 300 nM | 11766181 | 95% |
| hCXCL11.0013-G1T4k.one//VHn-G1T4h.one.H435R | 33 nM | 5487357 | 71% |
| | 100 nM | 13055822 | 78% |
| | 300 nM | 10050371 | 81% |
| hCXCL11.0014-G1T4k.one//VHn-G1T4h.one.H435R | 33 nM | 8071684 | 105% |
| | 100 nM | 14827193 | 89% |
| | 300 nM | 7512090 | 60% |
| hCXCL11.0015-G1T4k.one//VHn-G1T4h.one.H435R | 33 nM | 2619355 | 34% |
| | 100 nM | 12251752 | 73% |
| | 300 nM | 12226549 | 98% |
| hCXCL11.0016-G1T4k.one//VHn-G1T4h.one.H435R | 33 nM | 4954461 | 65% |
| | 100 nM | 12478741 | 75% |
| | 300 nM | 8570401 | 69% |
| hCXCL11.0017-G1T4k.one//VHn-G1T4h.one.H435R | 33 nM | 4718379 | 61% |
| | 100 nM | 12382919 | 74% |
| | 300 nM | 8542065 | 69% |
| hCXCL11.0018-G1T4k.one//VHn-G1T4h.one.H435R | 33 nM | 1845181 | 24% |
| | 100 nM | 8322700 | 50% |
| | 300 nM | 10085156 | 81% |
| hCXCL11.0019-G1T4k.one//VHn-G1T4h.one.H435R | 33 nM | 324679 | 4% |
| | 100 nM | 4663405 | 28% |
| | 300 nM | 11500114 | 93% |
| hCXCL11.0020-G1T4k.one//VHn-G1T4h.one.H435R | 33 nM | 2147154 | 28% |
| | 100 nM | 10335154 | 62% |
| | 300 nM | 11840783 | 95% |
| hCXCL11.0021-G1T4k.one//VHn-G1T4h.one.H435R | 33 nM | 8264372 | 108% |
| | 100 nM | 15582696 | 93% |
| | 300 nM | 10374927 | 84% |
| hCXCL11.0022-G1T4k.one//VHn-G1T4h.one.H435R | 33 nM | 13708021 | 178% |
| | 100 nM | 14788901 | 89% |
| | 300 nM | 6063758 | 49% |
| hCXCL11.0023-G1T4k.one//VHn-G1T4h.one.H435R | 33 nM | 14492680 | 189% |
| | 100 nM | 16351578 | 98% |
| | 300 nM | 5977170 | 48% |
| hCXCL11.0024-G1T4k.one//VHn-G1T4h.one.H435R | 33 nM | 2468213 | 32% |
| | 100 nM | 12017591 | 72% |
| | 300 nM | 13078459 | 105% |
| hCXCL11.0025-G1T4k.one//VHn-G1T4h.one.H435R | 33 nM | 7106015 | 93% |
| | 100 nM | 16854099 | 101% |
| | 300 nM | 11417885 | 92% |
| hCXCL11.0026-G1T4k.one//VHn-G1T4h.one.H435R | 33 nM | 5461231 | 71% |
| | 100 nM | 12896605 | 77% |
| | 300 nM | 9918162 | 80% |
| hCXCL11.0027-G1T4k.one//VHn-G1T4h.one.H435R | 33 nM | 5181305 | 67% |
| | 100 nM | 16650755 | 100% |
| | 300 nM | 12691313 | 102% |
| hCXCL11.0028-G1T4k.one//VHn-G1T4h.one.H435R | 33 nM | 1997904 | 26% |
| | 100 nM | 8871909 | 53% |
| | 300 nM | 11143349 | 90% |
| hCXCL11.0029-G1T4k.one//VHn-G1T4h.one.H435R | 33 nM | 4066987 | 53% |
| | 100 nM | 15360335 | 92% |
| | 300 nM | 13405229 | 108% |
| hCXCL11.0030-G1T4k.one//VHn-G1T4h.one.H435R | 33 nM | 8745532 | 114% |
| | 100 nM | 16405096 | 98% |
| | 300 nM | 10632773 | 86% |
| hCXCL11.0031-G1T4k.one//VHn-G1T4h.one.H435R | 33 nM | 12690483 | 165% |
| | 100 nM | 15076138 | 90% |
| | 300 nM | 6388637 | 51% |
| hCXCL11.0032-G1T4k.one//VHn-G1T4h.one.H435R | 33 nM | 2501343 | 33% |
| | 100 nM | 11321789 | 68% |
| | 300 nM | 13074388 | 105% |

TABLE 9-continued

| Analyte name | Analyte concentration | | Luminescence calue | Activity retention rate* |
|---|---|---|---|---|
| hCXCL11.0033-G1T4k.one//VHn-G1T4h.one.H435R | 33 | nM | 15304363 | 199% |
| | 100 | nM | 15347940 | 92% |
| | 300 | nM | 3463231 | 28% |
| hCXCL11.0034-G1T4k.one//VHn-G1T4h.one.H435R | 33 | nM | 1485580 | 19% |
| | 100 | nM | 7452490 | 45% |
| | 300 | nM | 9628060 | 77% |
| hCXCL11.0035-G1T4k.one//VHn-G1T4h.one.H435R | 33 | nM | 12340990 | 161% |
| | 100 | nM | 15832089 | 95% |
| | 300 | nM | 5229763 | 42% |
| hCXCL11.0036-G1T4k.one//VHn-G1T4h.one.H435R | 33 | nM | 10717177 | 140% |
| | 100 | nM | 17569742 | 105% |
| | 300 | nM | 6589358 | 53% |
| hCXCL11.0037-G1T4k.one//VHn-G1T4h.one.H435R | 33 | nM | 8513395 | 111% |
| | 100 | nM | 18473079 | 111% |
| | 300 | nM | 9070191 | 73% |
| hCXCL11.0038-G1T4k.one//VHn-G1T4h.one.H435R | 33 | nM | 4627890 | 60% |
| | 100 | nM | 13910020 | 83% |
| | 300 | nM | 12340351 | 99% |
| hCXCL11.0039-G1T4k.one//VHn-G1T4h.one.H435R | 33 | nM | 7856054 | 102% |
| | 100 | nM | 14332028 | 86% |
| | 300 | nM | 9320232 | 75% |
| hCXCL11.0040-G1T4k.one//VHn-G1T4h.one.H435R | 33 | nM | 6255008 | 81% |
| | 100 | nM | 13071383 | 78% |
| | 300 | nM | 5049092 | 41% |
| hCXCL11.0041-G1T4k.one//VHn-G1T4h.one.H435R | 33 | nM | 1921985 | 25% |
| | 100 | nM | 9373409 | 56% |
| | 300 | nM | 5161844 | 42% |
| hCXCL11.0042-G1T4k.one//VHn-G1T4h.one.H435R | 33 | nM | 4702516 | 61% |
| | 100 | nM | 11224123 | 67% |
| | 300 | nM | 7225056 | 58% |
| hCXCL11.0044-G1T4k.one//VHn-G1T4h.one.H435R | 33 | nM | 5237460 | 68% |
| | 100 | nM | 12713748 | 76% |
| | 300 | nM | 8901072 | 72% |
| hCXCL11.0045-G1T4k.one//VHn-G1T4h.one.H435R | 33 | nM | 4668626 | 61% |
| | 100 | nM | 12595408 | 75% |
| | 300 | nM | 8297150 | 67% |
| hCXCL11.0046-G1T4k.one//VHn-G1T4h.one.H435R | 33 | nM | 760233 | 10% |
| | 100 | nM | 6035270 | 36% |
| | 300 | nM | 8054240 | 65% |
| hCXCL11.0047-G1T4k.one//VHn-G1T4h.one.H435R | 33 | nM | 390951 | 5% |
| | 100 | nM | 3715751 | 22% |
| | 300 | nM | 6480925 | 52% |
| hCXCL11.0048-G1T4k.one//VHn-G1T4h.one.H435R | 33 | nM | 3972971 | 52% |
| | 100 | nM | 12539456 | 75% |
| | 300 | nM | 8954633 | 72% |
| hCXCL11.0049-G1T4k.one//VHn-G1T4h.one.H435R | 33 | nM | 5103080 | 66% |
| | 100 | nM | 15010561 | 90% |
| | 300 | nM | 9323596 | 75% |
| hCXCL11.0050-G1T4k.one//VHn-G1T4h.one.H435R | 33 | nM | 2316728 | 30% |
| | 100 | nM | 8492561 | 51% |
| | 300 | nM | 7921116 | 64% |
| hCXCL11.0051-G1T4k.one//VHn-G1T4h.one.H435R | 33 | nM | 6461187 | 84% |
| | 100 | nM | 14895200 | 89% |
| | 300 | nM | 10154195 | 82% |
| hCXCL11.0052-G1T4k.one//VHn-G1T4h.one.H435R | 33 | nM | 5884538 | 77% |
| | 100 | nM | 15088702 | 90% |
| | 300 | nM | 8326367 | 67% |
| hCXCL11.0053-G1T4k.one//VHn-G1T4h.one.H435R | 33 | nM | 595479 | 8% |
| | 100 | nM | 4263268 | 26% |
| | 300 | nM | 7431787 | 60% |
| hCXCL11.0054-G1T4k.one//VHn-G1T4h.one.H435R | 33 | nM | 3242951 | 42% |
| | 100 | nM | 10496671 | 63% |
| | 300 | nM | 6335806 | 51% |
| hCXCL11.0055-G1T4k.one//VHn-G1T4h.one.H435R | 33 | nM | 2977345 | 39% |
| | 100 | nM | 9651636 | 58% |
| | 300 | nM | 5268238 | 42% |
| hCXCL11.0056-G1T4k.one//VHn-G1T4h.one.H435R | 33 | nM | 643342 | 8% |
| | 100 | nM | 5573043 | 33% |
| | 300 | nM | 7330097 | 59% |

TABLE 9-continued

| Analyte name | Analyte concentration | Luminescence calue | Activity retention rate* |
|---|---|---|---|
| hCXCL11.0057-G1T4k.one//VHn-G1T4h.one.H435R | 33 nM | 500643 | 7% |
| | 100 nM | 6205724 | 37% |
| | 300 nM | 10672011 | 86% |
| hCXCL11.0058-G1T4k.one//VHn-G1T4h.one.H435R | 33 nM | 1124561 | 15% |
| | 100 nM | 7072332 | 42% |
| | 300 nM | 10398939 | 84% |
| cell only | 0 nM | 52468 | — |

Activity retention rate*: percentage to the signal value of hCXCL10R75A-G1T4k.one//VHn-G1T4h.one.H435R at the corresponding concentration

Example 8. Evaluation of the Cell Migration-Inducing Activity of hITIP Variant Fc Fusions It was evaluated whether the hITIP variant Fc fusions prepared in Example 5 induce migration of cells expressing CXCR3 (cell migration-inducing activity). Cell migration-inducing activity was evaluated using Ba/F3 transfectant cells expressing human CXCR3 (hCXCR3) (hereinafter referred to as BaF3/hCXCR3) and HTS Transwell™-96 Permeable Supports with 5.0 μm Pore Polycarbonate Membrane (Cat. 3387, Corning).

The following hITIP variant Fc fusions prepared in Example 5 were used as analytes:

hITIP-G1T4k.one//VHn-G1T4h.one.H435R,
hITIP0003-G1T4k.one//VHn-G1T4h.one.H435R,
hITIP0004-G1T4k.one//VHn-G1T4h.one.H435R,
hITIP0005-G1T4k.one//VHn-G1T4h.one.H435R,
hITIP0006-G1T4k.one//VHn-G1T4h.one.H435R,
hITIP0007-G1T4k.one//VHn-G1T4h.one.H435R,
hITIP0008-G1T4k.one//VHn-G1T4h.one.H435R,
hITIP0009-G1T4k.one//VHn-G1T4h.one.H435R,
hITIP0010-G1T4k.one//VHn-G1T4h.one.H435R,
hITIP0011-G1T4k.one//VHn-G1T4h.one.H435R,
hITIP0012-G1T4k.one//VHn-G1T4h.one.H435R,
hITIP0013-G1T4k.one//VHn-G1T4h.one.H435R,
hITIP0014-G1T4k.one//VHn-G1T4h.one.H435R,
hITIP0015-G1T4k.one//VHn-G1T4h.one.H435R,
hITIP0016-G1T4k.one//VHn-G1T4h.one.H435R,
hITIP0017-G1T4k.one//VHn-G1T4h.one.H435R,
hITIP0018-G1T4k.one//VHn-G1T4h.one.H435R,
hITIP0019-G1T4k.one//VHn-G1T4h.one.H435R,
hITIP0020-G1T4k.one//VHn-G1T4h.one.H435R,
hITIP0021-G1T4k.one//VHn-G1T4h.one.H435R,
hITIP0022-G1T4k.one//VHn-G1T4h.one.H435R,
hITIP0023-G1T4k.one//VHn-G1T4h.one.H435R,
hITIP0024-G1T4k.one//VHn-G1T4h.one.H435R,
hITIP0025-G1T4k.one//VHn-G1T4h.one.H435R,
hITIP0026-G1T4k.one//VHn-G1T4h.one.H435R,
hITIP0027-G1T4k.one//VHn-G1T4h.one.H435R,
hITIP0028-G1T4k.one//VHn-G1T4h.one.H435R,
hITIP0029-G1T4k.one//VHn-G1T4h.one.H435R,
hITIP0030-G1T4k.one//VHn-G1T4h.one.H435R,
hITIP0031-G1T4k.one//VHn-G1T4h.one.H435R,
hITIP0033-G1T4k.one//VHn-G1T4h.one.H435R,
hITIP0034-G1T4k.one//VHn-G1T4h.one.H435R,
hITIP0035-G1T4k.one//VHn-G1T4h.one.H435R,
hITIP0036-G1T4k.one//VHn-G1T4h.one.H435R,
hITIP0037-G1T4k.one//VHn-G1T4h.one.H435R,
hITIP0038-G1T4k.one//VHn-G1T4h.one.H435R,
hITIP0039-G1T4k.one//VHn-G1T4h.one.H435R,
hITIP0040-G1T4k.one//VHn-G1T4h.one.H435R,
hITIP0041-G1T4k.one//VHn-G1T4h.one.H435R,
hITIP0042-G1T4k.one//VHn-G1T4h.one.H435R,
hITIP0044-G1T4k.one//VHn-G1T4h.one.H435R,
hITIP0045-G1T4k.one//VHn-G1T4h.one.H435R,
hITIP0046-G1T4k.one//VHn-G1T4h.one.H435R,
hITIP0047-G1T4k.one//VHn-G1T4h.one.H435R,
hITIP0048-G1T4k.one//VHn-G1T4h.one.H435R,
hITIP0049-G1T4k.one//VHn-G1T4h.one.H435R,
hITIP0050-G1T4k.one//VHn-G1T4h.one.H435R,
hITIP0051-G1T4k.one//VHn-G1T4h.one.H435R,
hITIP0052-G1T4k.one//VHn-G1T4h.one.H435R,
hITIP0053-G1T4k.one//VHn-G1T4h.one.H435R,
hITIP0054-G1T4k.one//VHn-G1T4h.one.H435R,
hITIP0055-G1T4k.one//VHn-G1T4h.one.H435R,
hITIP0056-G1T4k.one//VHn-G1T4h.one.H435R,
hITIP0057-G1T4k.one//VHn-G1T4h.one.H435R, and
hITIP0058-G1T4k.one//VHn-G1T4h.one.H435R.

After adjusting the final concentration in the solution of each analyte to be analyzed to be 33 nM, 100 nM, and 300 nM, 235 μL of each solution was transferred to the lower chamber. Then, BaF3/hCXCR3 cells were seeded into the upper chamber at 75 μL/well so as to be $2.0 \times 10^5$ cells/well, and the reaction was carried out for 18 hours under the conditions of 5% carbon dioxide and 37° C. After reacting for 18 hours, 100 μL of the solution in the lower chamber was transferred to OptiPlate-96 (Cat. 6005299, PerkinElmer), and 100 μL of CellTiter-Glo™ Luminescent Cell Viability Assay solution (Cat. G7571, Promega) was added. After reacting at room temperature for 10 minutes, the luminescence value was measured with a 2104 EnVision™ multi-label reader (PerkinElmer) to evaluate the level of migration of cells into the lower chamber.

The luminescence intensity reflects the amount of cells that migrated into the lower chamber. The cell migration-inducing activities of hITIP-G1T4k.one//VHn-G1T4 h.one.H435R and of the other hITIP variant Fc fusions were compared.

Figure 7A:
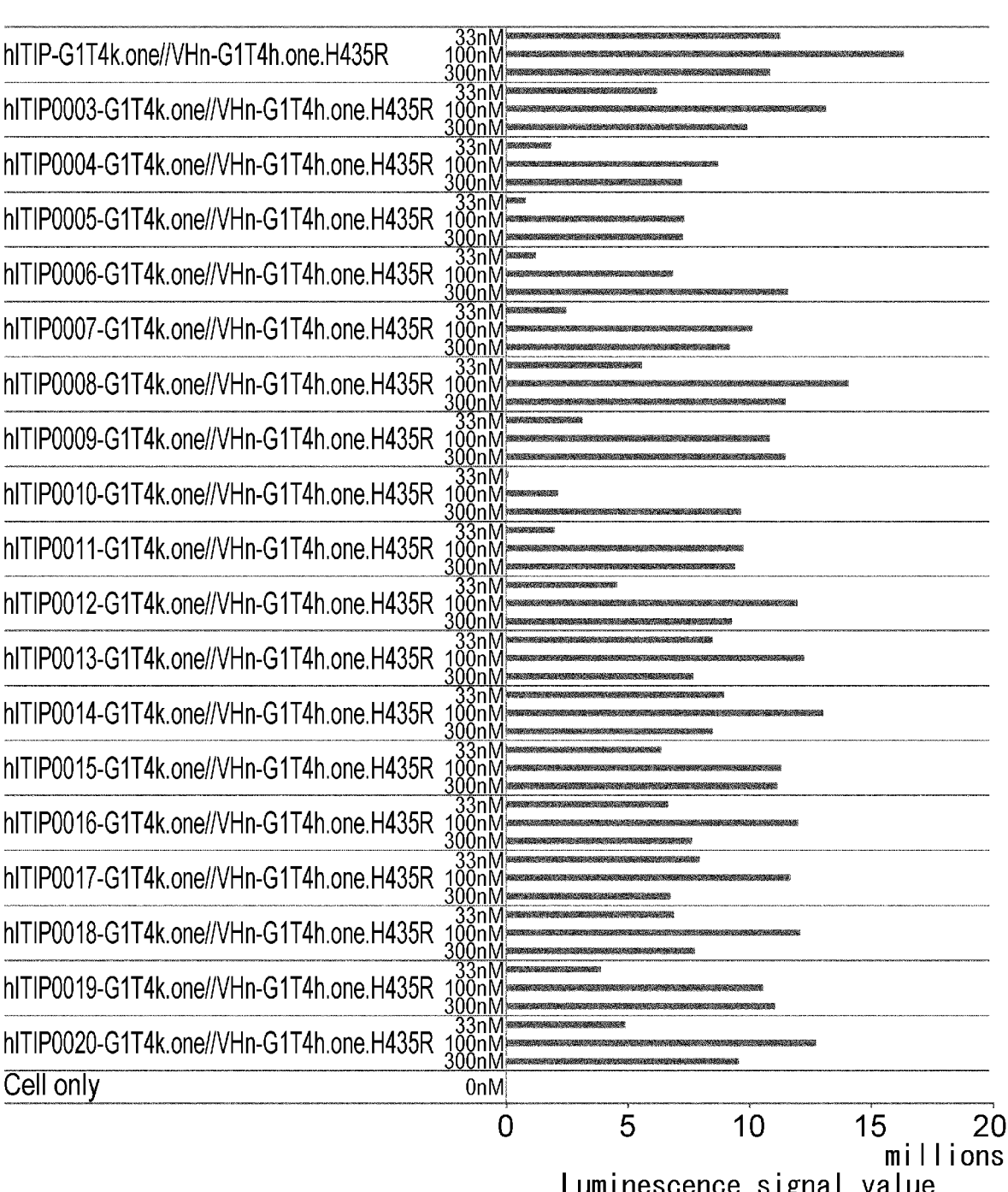
FIG. 7a shows the cell migration-inducing activity of each hITIP variant Fc fusion.
Figure 7B:
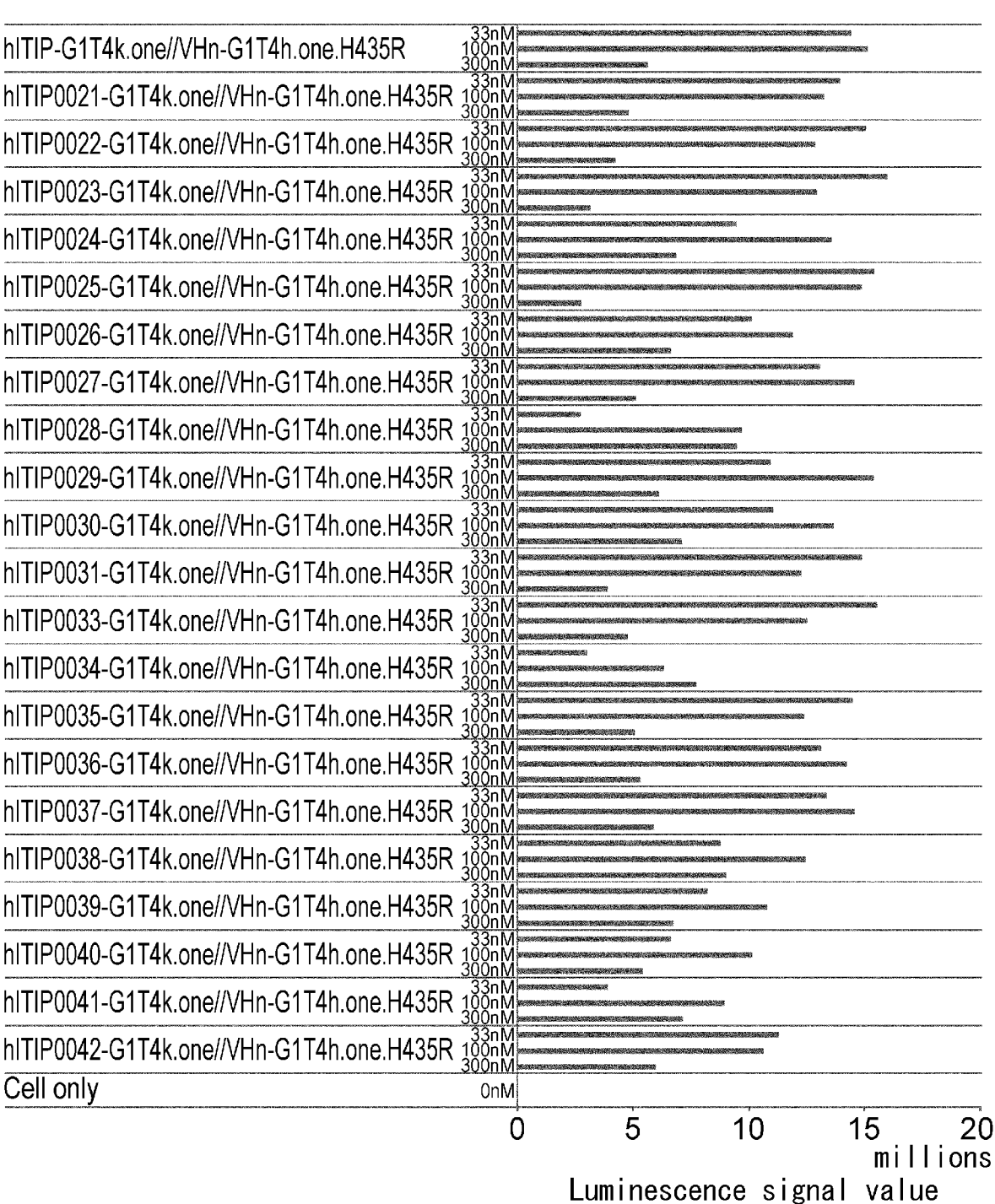
FIG. 7b shows the cell migration-inducing activity of each hITIP variant Fc fusion.
Figure 7C:
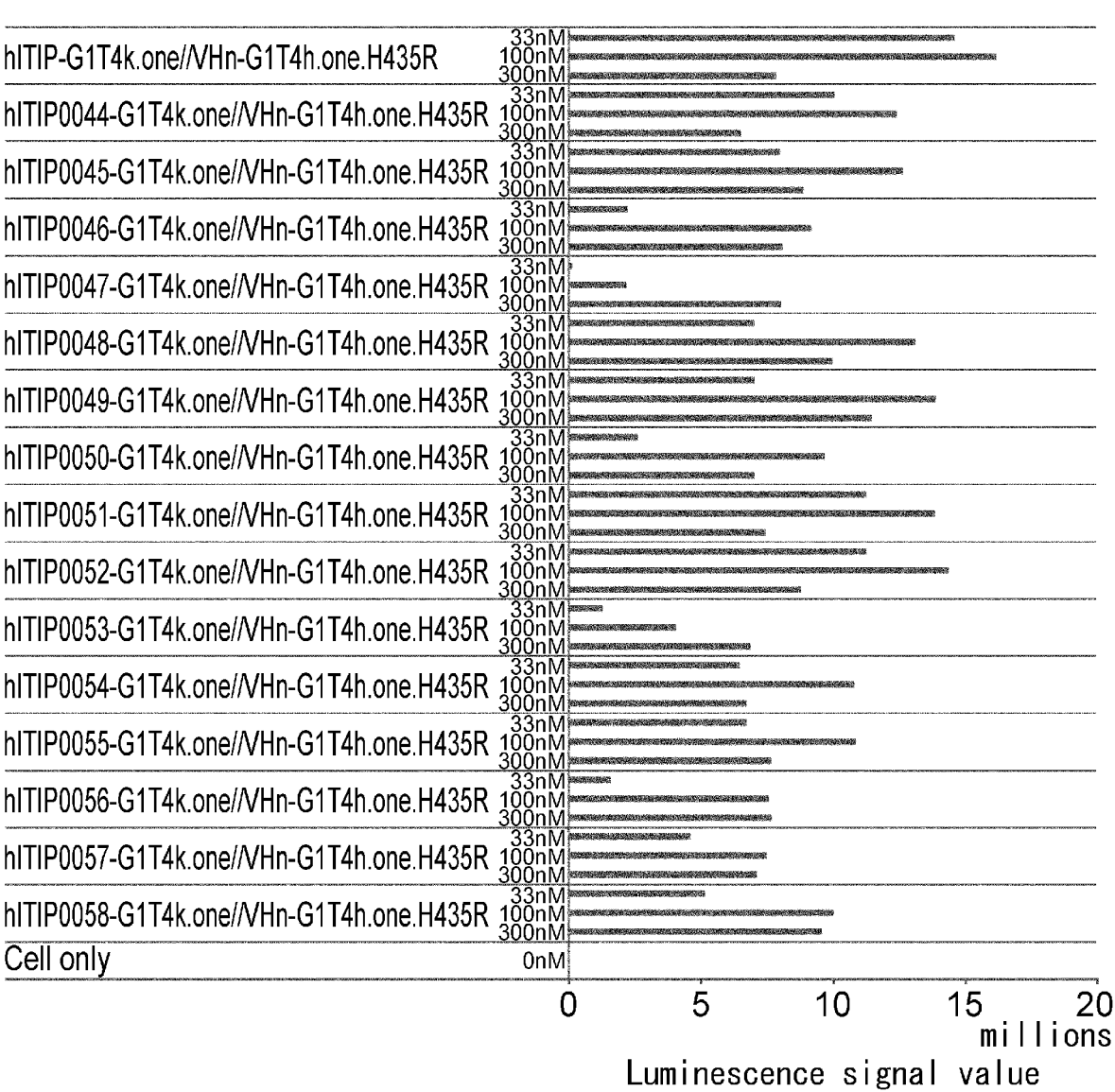
FIG. 7c shows the cell migration-inducing activity of each hITIP variant Fc fusion.

Comparison of the cell migration-inducing activities of hITIP-G1T4k.one//VHn-G1T4h.one.H435R and of the other hITIP variant Fc fusion was performed after 18 hours of reaction, and the results are shown in FIG. 7 (FIG. 7a, FIG. 7b, and FIG. 7c), and Table 10.

hITIP0003-G1T4k.one//VHn-G1T4h.one.H435R,
hITIP0008-G1T4k.one//VHn-G1T4h.one.H435R,
hITIP0009-G1T4k.one//VHn-G1T4h.one.H435R,
hITIP0012-G1T4k.one//VHn-G1T4h.one.H435R,
hITIP0013-G1T4k.one//VHn-G1T4h.one.H435R,
hITIP0014-G1T4k.one//VHn-G1T4h.one.H435R,
hITIP0015-G1T4k.one//VHn-G1T4h.one.H435R,
hITIP0016-G1T4k.one//VHn-G1T4h.one.H435R,
hITIP0017-G1T4k.one//VHn-G1T4h.one.H435R,
hITIP0018-G1T4k.one//VHn-G1T4h.one.H435R, hITIP0019-G1T4k.one//VHn-G1T4h.one.H435R,
hITIP0020-G1T4k.one//VHn-G1T4h.one.H435R,
hITIP0021-G1T4k.one//VHn-G1T4h.one.H435R,
hITIP0022-G1T4k.one//VHn-G1T4h.one.H435R,
hITIP0023-G1T4k.one//VHn-G1T4h.one.H435R,
hITIP0024-G1T4k.one//VHn-G1T4h.one.H435R,
hITIP0025-G1T4k.one//VHn-G1T4h.one.H435R,
hITIP0026-G1T4k.one//VHn-G1T4h.one.H435R,
hITIP0027-G1T4k.one//VHn-G1T4h.one.H435R,
hITIP0029-G1T4k.one//VHn-G1T4h.one.H435R,
hITIP0030-G1T4k.one//VHn-G1T4h.one.H435R,
hITIP0031-G1T4k.one//VHn-G1T4h.one.H435R,
hITIP0033-G1T4k.one//VHn-G1T4h.one.H435R,
hITIP0035-G1T4k.one//VHn-G1T4h.one.H435R,
hITIP0036-G1T4k.one//VHn-G1T4h.one.H435R,
hITIP0037-G1T4k.one//VHn-G1T4h.one.H435R,
hITIP0038-G1T4k.one//VHn-G1T4h.one.H435R,
hITIP0039-G1T4k.one//VHn-G1T4h.one.H435R, hITIP0040-G1T4k.one//VHn-G1T4h.one.H435R,
hITIP0041-G1T4k.one//VHn-G1T4h.one.H435R,
hITIP0042-G1T4k.one//VHn-G1T4h.one.H435R,
hITIP0044-G1T4k.one//VHn-G1T4h.one.H435R,
hITIP0045-G1T4k.one//VHn-G1T4h.one.H435R,
hITIP0048-G1T4k.one//VHn-G1T4h.one.H435R,
hITIP0049-G1T4k.one//VHn-G1T4h.one.H435R,
hITIP0051-G1T4k.one//VHn-G1T4h.one.H435R,
hITIP0052-G1T4k.one//VHn-G1T4h.one.H435R,
hITIP0054-G1T4k.one//VHn-G1T4h.one.H435R,
hITIP0055-G1T4k.one//VHn-G1T4h.one.H435R,
hITIP0057-G1T4k.one//VHn-G1T4h.one.H435R, and
hITIP0058-G1T4k.one//VHn-G1T4h.one.H435R
retained, at each of the concentration of 33 nM, 100 nM, 300 nM, 25% or more of cell migration-inducing activity of hITIP-G1T4k.one//VHn-G1T4h.one.H435R at the same concentration. From this, it was shown that the hITIP variants contained in these hITIP variant Fc fusions have sufficient activity.

TABLE 10

| | | | Activity |
|---|---|---|---|
| | Analyte | Luminescence | retention |
| Analyte name | concentration | value | rate* |
| Sample set_1 | | | |

| Analyte name | Analyte concentration | Luminescence value | Activity retention rate* |
|---|---|---|---|
| hITIP-G1T4k.one//VHn-G1T4h.one.H435R | 33 nM | 11255810 | |
| | 100 nM | 16333190 | |
| | 300 nM | 10853981 | |
| hITIP0003-G1T4k.one//VHn-G1T4h.one.H435R | 33 nM | 6184897 | 55% |
| | 100 nM | 13130438 | 80% |
| | 300 nM | 9909618 | 91% |
| hITIP0004-G1T4k.one//VHn-G1T4h.one.H435R | 33 nM | 1864821 | 17% |
| | 100 nM | 8714209 | 53% |
| | 300 nM | 7226926 | 67% |
| hITIP0005-G1T4k.one//VHn-G1T4h.one.H435R | 33 nM | 802531 | 7% |
| | 100 nM | 7331671 | 45% |
| | 300 nM | 7271155 | 67% |
| hITIP0006-G1T4k.one//VHn-G1T4h.one.H435R | 33 nM | 1230226 | 11% |
| | 100 nM | 6851471 | 42% |
| | 300 nM | 11591358 | 107% |
| hITIP0007-G1T4k.one//VHn-G1T4h.one.H435R | 33 nM | 2479379 | 22% |
| | 100 nM | 10108277 | 62% |
| | 300 nM | 9182812 | 85% |
| hITIP0008-G1T4k.one//VHn-G1T4h.one.H435R | 33 nM | 5585908 | 50% |
| | 100 nM | 14059020 | 86% |
| | 300 nM | 11481733 | 106% |
| hITIP0009-G1T4k.one//VHn-G1T4h.one.H435R | 33 nM | 3141421 | 28% |
| | 100 nM | 10831129 | 66% |
| | 300 nM | 11479957 | 106% |
| hITIP0010-G1T4k.one//VHn-G1T4h.one.H435R | 33 nM | 104208 | 1% |
| | 100 nM | 2139235 | 13% |
| | 300 nM | 9641767 | 89% |
| hITIP0011-G1T4k.one//VHn-G1T4h.one.H435R | 33 nM | 2012679 | 18% |
| | 100 nM | 9741847 | 60% |
| | 300 nM | 9395780 | 87% |
| hITIP0012-G1T4k.one//VHn-G1T4h.one.H435R | 33 nM | 4553615 | 40% |
| | 100 nM | 11974754 | 73% |
| | 300 nM | 9283034 | 86% |
| hITIP0013-G1T4k.one//VHn-G1T4h.one.H435R | 33 nM | 8489369 | 75% |
| | 100 nM | 12237110 | 75% |
| | 300 nM | 7711718 | 71% |
| hITIP0014-G1T4k.one//VHn-G1T4h.one.H435R | 33 nM | 8972343 | 80% |
| | 100 nM | 13028436 | 80% |
| | 300 nM | 8481716 | 78% |
| hITIP0015-G1T4k.one//VHn-G1T4h.one.H435R | 33 nM | 6378932 | 57% |
| | 100 nM | 11292522 | 69% |
| | 300 nM | 11163432 | 103% |
| hITIP0016-G1T4k.one//VHn-G1T4h.one.H435R | 33 nM | 6656446 | 59% |
| | 100 nM | 11995226 | 73% |
| | 300 nM | 7646801 | 70% |
| hITIP0017-G1T4k.one//VHn-G1T4h.one.H435R | 33 nM | 7957520 | 71% |
| | 100 nM | 11671324 | 71% |
| | 300 nM | 6762275 | 62% |

TABLE 10-continued

| | | | |
|---|---|---|---|
| hITIP0018-G1T4k.one//VHn-G1T4h.one.H435R | 33 nM | 6897647 | 61% |
| | 100 nM | 12083915 | 74% |
| | 300 nM | 7743185 | 71% |
| hIlTIP0019-G1T4k.one//VHn-G1T4h.one.H435R | 33 nM | 3893156 | 35% |
| | 100 nM | 10537283 | 65% |
| | 300 nM | 11047471 | 102% |
| hITIP0020-G1T4k.one//VHn-G1T4h.one.H435R | 33 nM | 4898429 | 44% |
| | 100 nM | 12726742 | 78% |
| | 300 nM | 9561501 | 88% |

Sample set_2

| Analyte name | Analyte concentration | Luminescence value | Activity retention rate* |
|---|---|---|---|
| hITIP-G1T4k.one//VHn-G1T4h.one.H435R | 33 nM | 14416819 | |
| | 100 nM | 15131844 | |
| | 300 nM | 5642551 | |
| hITIP0021-G1T4k.one//VHn-G1T4h.one.H435R | 33 nM | 13956263 | 97% |
| | 100 nM | 13254701 | 88% |
| | 300 nM | 4839338 | 86% |
| hITIP0022-G1T4k.one//VHn-G1T4h.one.H435R | 33 nM | 15061363 | 104% |
| | 100 nM | 12879459 | 85% |
| | 300 nM | 4246847 | 75% |
| hITIP0023-G1T4k.one//VHn-G1T4h.one.H435R | 33 nM | 15979606 | 111% |
| | 100 nM | 12935580 | 85% |
| | 300 nM | 3156988 | 56% |
| hITIP0024-G1T4k.one//VHn-G1T4h.one.H435R | 33 nM | 9470253 | 66% |
| | 100 nM | 13585196 | 90% |
| | 300 nM | 6872305 | 122% |
| hITIP0025-G1T4k.one//VHn-G1T4h.one.H435R | 33 nM | 15422760 | 107% |
| | 100 nM | 14866297 | 98% |
| | 300 nM | 2767805 | 49% |
| hITIP0026-G1T4k.one//VHn-G1T4h.one.H435R | 33 nM | 10128027 | 70% |
| | 100 nM | 11888103 | 79% |
| | 300 nM | 6631111 | 118% |
| hITIP0027-G1T4k.one//VHn-G1T4h.one.H435R | 33 nM | 13086406 | 91% |
| | 100 nM | 14555849 | 96% |
| | 300 nM | 5126848 | 91% |
| hITIP0028-G1T4k.one//VHn-G1T4h.one.H435R | 33 nM | 2744330 | 19% |
| | 100 nM | 9691581 | 64% |
| | 300 nM | 9498848 | 168% |
| hITIP0029-G1T4k.one//VHn-G1T4h.one.H435R | 33 nM | 10941109 | 76% |
| | 100 nM | 15408714 | 102% |
| | 300 nM | 6128140 | 109% |
| hITIP0030-G1T4k.one//VHn-G1T4h.one.H435R | 33 nM | 11055133 | 77% |
| | 100 nM | 13666700 | 90% |
| | 300 nM | 7108276 | 126% |
| hITIP0031-G1T4k.one//VHn-G1T4h.one.H435R | 33 nM | 14905473 | 103% |
| | 100 nM | 12274657 | 81% |
| | 300 nM | 3921392 | 69% |
| hITIP0033-G1T4k.one//VHn-G1T4h.one.H435R | 33 nM | 15539594 | 108% |
| | 100 nM | 12523151 | 83% |
| | 300 nM | 4770826 | 85% |
| hITIP0034-G1T4k.one//VHn-G1T4h.one.H435R | 33 nM | 3014026 | 21% |
| | 100 nM | 6337835 | 42% |
| | 300 nM | 7730336 | 137% |
| hITIP0035-G1T4k.one//VHn-G1T4h.one.H435R | 33 nM | 14479491 | 100% |
| | 100 nM | 12391946 | 82% |
| | 300 nM | 5087719 | 90% |
| hITIP0036-G1T4k.one//VHn-G1T4h.one.H435R | 33 nM | 13125449 | 91% |
| | 100 nM | 14230048 | 94% |
| | 300 nM | 5303773 | 94% |
| hITIP0037-G1T4k.one//VHn-G1T4h.one.H435R | 33 nM | 13362538 | 93% |
| | 100 nM | 14557898 | 96% |
| | 300 nM | 5896904 | 105% |
| hITIP0038-G1T4k.one//VHn-G1T4h.one.H435R | 33 nM | 8778686 | 61% |
| | 100 nM | 12447834 | 82% |
| | 300 nM | 9021217 | 160% |
| hITIP0039-G1T4k.one//VHn-G1T4h.one.H435R | 33 nM | 8218579 | 57% |
| | 100 nM | 10785484 | 71% |
| | 300 nM | 6753122 | 120% |
| hITIP0040-G1T4k.one//VHn-G1T4h.one.H435R | 33 nM | 6641961 | 46% |
| | 100 nM | 10152246 | 67% |
| | 300 nM | 5422998 | 96% |
| hITIP0041-G1T4k.one//VHn-G1T4h.one.H435R | 33 nM | 3911869 | 27% |
| | 100 nM | 8945206 | 59% |
| | 300 nM | 7154135 | 127% |

TABLE 10-continued

| | | | |
|---|---|---|---|
| hITIP0042-G1T4k.one//VHn-G1T4h.one.H435R | 33 nM | 11287798 | 78% |
| | 100 nM | 10640127 | 70% |
| | 300 nM | 5991955 | 106% |

| Sample set_3 | | | |
|---|---|---|---|

| Analyte name | Analyte concentratioN | Luminescence value | Activity retention rate* |
|---|---|---|---|
| hITIP-G1T4k.one//VHn-G1T4h.one.H435R | 33 nM | 14582717 | |
| | 100 nM | 16151041 | |
| | 300 nM | 7844794 | |
| hITIP0044-G1T4k.one//VHn-G1T4h.one.H435R | 33 nM | 10045938 | 69% |
| | 100 nM | 12391082 | 77% |
| | 300 nM | 6527919 | 83% |
| hITIP0045-G1T4k.one//VHn-G1T4h.one.H435R | 33 nM | 7976121 | 55% |
| | 100 nM | 12629509 | 78% |
| | 300 nM | 8864666 | 113% |
| hITIP0046-G1T4k.one//VHn-G1T4h.one.H435R | 33 nM | 2230683 | 15% |
| | 100 nM | 9165961 | 57% |
| | 300 nM | 8091881 | 103% |
| hITIP0047-G1T4k.one//VHn-G1T4h.one.H435R | 33 nM | 158870 | 1% |
| | 100 nM | 2192199 | 14% |
| | 300 nM | 8023795 | 102% |
| hITIP0048-G1T4k.one//VHn-G1T4h.one.H435R | 33 nM | 7012064 | 48% |
| | 100 nM | 13095826 | 81% |
| | 300 nM | 9972870 | 127% |
| hITIP0049-G1T4k.one//VHn-G1T4h.one.H435R | 33 nM | 7019689 | 48% |
| | 100 nM | 13895669 | 86% |
| | 300 nM | 11446853 | 146% |
| hITIP0050-G1T4k.one//VHn-G1T4h.one.H435R | 33 nM | 2605315 | 18% |
| | 100 nM | 9676705 | 60% |
| | 300 nM | 7018480 | 89% |
| hITIP0051-G1T4k.one//VHn-G1T4h.one.H435R | 33 nM | 11235454 | 77% |
| | 100 nM | 13839262 | 86% |
| | 300 nM | 7446291 | 95% |
| hITIP0052-G1T4k.one//VHn-G1T4h.one.H435R | 33 nM | 11235767 | 77% |
| | 100 nM | 14357609 | 89% |
| | 300 nM | 8783137 | 112% |
| hITIP0053-G1T4k.one//VHn-G1T4h.one.H435R | 33 nM | 1289632 | 9% |
| | 100 nM | 4047257 | 25% |
| | 300 nM | 6884729 | 88% |
| hITIP0054-G1T4k.one//VHn-G1T4h.one.H435R | 33 nM | 6461440 | 44% |
| | 100 nM | 10787916 | 67% |
| | 300 nM | 6726740 | 86% |
| hITIP0055-G1T4k.one//VHn-G1T4h.one.H435R | 33 nM | 6716736 | 46% |
| | 100 nM | 10851741 | 67% |
| | 300 nM | 7652397 | 98% |
| hITIP0056-G1T4k.one//VHn-G1T4h.one.H435R | 33 nM | 1586824 | 11% |
| | 100 nM | 7566720 | 47% |
| | 300 nM | 7679419 | 98% |
| hITIP0057-G1T4k.one//VHn-G1T4h.one.H435R | 33 nM | 4605304 | 32% |
| | 100 nM | 7485005 | 46% |
| | 300 nM | 7123475 | 91% |
| hITIP0058-G1T4k.one//VHn-G1T4h.one.H435R | 33 nM | 5163373 | 35% |
| | 100 nM | 10015503 | 62% |
| | 300 nM | 9561334 | 122% |
| cell only | 0 nM | 31290 | — |

Activity retention rate*: percentage to the signal value of
hITIP-G1T4k.one//VHn-G1T4h.one. H435R at the corresponding concentration

Example 9. Evaluation of DPPIV Cleavage Resistance of hCXCL11 Variant Fc Fusions and hITIP Variant Fc Fusions It was examined whether the hCXCL11 variant Fc fusions and the hITIP variant Fc fusions that induced cell migration in Examples 7 and 8 are cleaved by dipeptidyl peptidase IV (DPPIV). Human DPPIV (hDPPIV) (Biolegend, 764102) derived from human was used as DPPIV. Cleavage of hCXCL11 variant Fc fusions and hITIP variant Fc fusions by DPPIV was evaluated by LC/MS analysis after N-type deglycosylation and reduction treatment. After reacting hCXCL11 variant Fc fusions and hITIP variant Fc fusions at a final concentration of 0.2 mg/ml (3.3 μM) and hDPPIV at a final concentration of 200 nM in PBS for 1 hour at 37° C., LC/MS analysis was performed by a method known to those skilled in the art, and the cleavage of the hCXCL11 variant Fc fusions and hITIP variant Fc fusions was evaluated.

For hCXCL11-G1T4k.one//VHn-G1T4h.one.H435R and hITIP-G1T4k.one//VHn-G1T4h.one.H435R, DPPIV treatment reduced each of the masses of the hCXCL11 variant-containing peptide chain and the hITIP variant-containing peptide chain. The masses corresponded to the theoretical masses of the sequences of each of the hCXCL11 variant-containing peptide chain and the hITIP variant-containing peptide chain lacking the two amino acid residues from the N-terminal. This suggested that the two amino acid residues from the N-terminal of hCXCL11 and hITIP contained in hCXCL11-G1T4k.one//VHn-G1T4h.one.H435R and hITIP-G1T4k.one//VHn-G1T4h.one.H435R were cleaved by hDP-PIV.

On the other hand,
hCXCL11.0021-G1T4k.one//VHn-G1T4h.one.H435R
hCXCL11.0022-G1T4k.one//VHn-G1T4h.one.H435R,
hCXCL11.0023-G1T4k.one//VHn-G1T4h.one.H435R,
hCXCL11.0025-G1T4k.one//VHn-G1T4h.one.H435R,
hCXCL 11.0030-G1T4k.one//VHn-G1T4h.one.H435R,
hCXCL 11.0031-G1T4k.one//VHn-G1T4h.one.H435R,
hCXCL 11.0033-G1T4k.one//VHn-G1T4h.one.H435R,
hCXCL 11.0035-G1T4k.one//VHn-G1T4h.one.H435R,
hCXCL 11.0036-G1T4k.one//VHn-G1T4h.one.H435R,
hCXCL 11.0037-G1T4k.one//VHn-G1T4h.one.H435R,
hCXCL 11.0039-G1T4k.one//VHn-G1T4h.one.H435R,
hITIP0021-G1T4k.one//VHn-G1T4h.one.H435R,
hITIP0022-G1T4k.one//VHn-G1T4h.one.H435R,
hITIP0023-G1T4k.one//VHn-G1T4h.one.H435R,
hITIP0025-G1T4k.one//VHn-G1T4h.one.H435R,
hITIP0030-G1T4k.one//VHn-G1T4h.one.H435R,
hITIP0031-G1T4k.one//VHn-G1T4h.one.H435R,
hITIP0033-G1T4k.one//VHn-G1T4h.one.H435R,
hITIP0035-G1T4k.one//VHn-G1T4h.one.H435R,
hITIP0036-G1T4k.one//VHn-G1T4h.one.H435R,
hITIP0037-G1T4k.one//VHn-G1T4h.one.H435R, and
hITIP0039-G1T4k.one//VHn-G1T4h.one.H435R showed
no mass change suggestive of peptide bond cleavage by hDPPIV treatment. From this result, it was suggested that the hCXCL11 variants and hITIP contained in these hCXCL11 variant Fc fusions and hITIP variant Fc fusions show hDPPIV cleavage resistance.

Since the two amino acid residues from the N-terminal of hCXCL11 and hITIP are cleaved by hDPPIV, it was suggested that the amino acid modifications in and around the DPPIV recognition/cleavage site contained in the above hCXCL11 variants and hITIP variants that did not show a mass change due to hDPPIV treatment are useful modifications to provide DPPIV resistance to hCXCL11 and hITIP.

Although the foregoing invention has been described in some detail by way of illustration and example for purposes of clarity of understanding, the descriptions and examples should not be construed as limiting the scope of the disclosure. The disclosures of all patent and scientific literature cited herein are expressly incorporated in their entirety by reference.

INDUSTRIAL APPLICABILITY

The present disclosure is the first disclosure of CXCR3 ligands having resistance to DPPIV and also having the activity to cause migration of cells expressing CXCR3. Such CXCR3 ligands are useful for disease treatment/prevention by causing migration of cells expressing CXCR3.

---

The invention claimed is:

1. A C-X-C Motif Chemokine Receptor 3 (CXCR3) ligand, wherein the CXCR3 ligand comprises:
a human C-X-C motif chemokine 10 (CXCL10) variant derived from human CXCL10 (SEQ ID NO: 60), wherein the N-terminal sequence of the CXCL10 variant is selected from the group consisting of:
(a1) V-X1-L, wherein X1 is F, G, I, K, L, M, T, V, W, or Y and wherein V-X1-L is substituted for the N-terminal V-P-L amino acid residues of human CXCL10;
(a2) X2-V-P, wherein X2 is A, F, G, H, I, K, L, N, P, Q, R, S, T, V, W, or Y and wherein X2 is an amino acid residue added at the N-terminus of the N-terminal V-P amino acid residues of human CXCL10;
(a3) V-X3-P, wherein X3 is A, F, G, H, I, K, L, M, Q, R, S, T, V, W, or Y and wherein X3 is an amino acid residue inserted between the N-terminal V-P amino acid residues of human CXCL10; and,
(a4) P-L-S wherein the valine residue at the N-terminus of human CXCL10 is deleted; or, a human C-X-C motif chemokine 11 (CXCL11) variant derived from human CXCL11 (SEQ ID NO: 61) or a human CXCL10-human CXCL11 chimeric protein (ITIP) variant derived from ITIP (SEQ ID NO: 63), wherein the N-terminal sequence of the CXCL11 variant or the chimeric protein ITIP variant is selected from the group consisting of:
(a5) X4-F-P, wherein X4 is A, D, E, F, G, H, I, K, L, M, N, P, Q, S, T, V, W, or Y and wherein X4 is an amino acid residue added at the N-terminus of the N-terminal F-P amino acid residues of human CXCL11 or the chimeric protein ITIP;
(a6) F-X5-M, wherein X5 is A, D, E, G, H, I, M, N, Q, R, S, T, V, W, or Y and wherein X5 is an amino acid residue substitution of proline (P) at the N-terminal F-P-M amino acid residues of human CXCL11 or the chimeric protein ITIP variant; and,
(a7) F-X6-P, wherein X6 is A, D, E, F, G, H, L, M, N, P, Q, S, T, W, or Y and wherein X6 is an amino acid residue inserted between the N-terminal F-P amino acid residues of human CXCL11 or the chimeric protein ITIP variant.

2. A CXCR3 ligand comprising an N-terminal sequence according to claim 1, wherein the CXCR3 ligand has comprises a sequence at the C-terminus of the C-X-C motif selected from the group consisting of:
(c1) the sequence from the 12th amino acid to the 77th amino acid of SEQ ID NO: 60;
(c2) the sequence from the 12th amino acid to the 73rd amino acid of SEQ ID NO: 61;
(c3) the sequence from the 12th amino acid to the 103rd amino acid of SEQ ID NO: 62;
(c4) the sequence from the 12th amino acid to the 77th amino acid of SEQ ID NO: 1; and
(c5) the sequence from the 12$^{th}$ amino acid to the 77$^{th}$ amino acid of SEQ ID NO: 63.

3. A CXCR3 ligand comprising an N-terminal sequence according to claim 1, wherein a C-terminal sequence of the CXCR3 ligand comprises a sequence selected from the group consisting of:
(d1) any one of SEQ ID NOs: 2 to 49, 51 to 57, 92 to 147, and 149 to 204;
(d2) a sequence comprising 95% or more sequence identity to SEQ ID NO: 60;
(d3) a sequence comprising 95% or more sequence identity to SEQ ID NO: 61;
(d4) a sequence comprising 95% or more sequence identity to SEQ ID NO: 62;
(d5) a sequence comprising 95% or more sequence identity to SEQ ID NO: 63;
(d6) a sequence comprising 95% or more sequence identity to SEQ ID NO: 1; and
(d7) a sequence comprising 3 or less amino acid substitutions, insertions, or deletions in a sequence selected from any one of SEQ ID NOs: 1 to 49, 51 to 57, 60 to 63, 92 to 147, and 149 to 204,
wherein differences in percent sequence identity or amino acid substitutions are conservative amino acid substitutions, wherein said ligand has an activity to cause migration of cells expressing CXCR3.

4. The CXCR3 ligand according to claim 1, wherein the CXCL10 variant further comprises a substitution of arginine to alanine at amino acid position 75.

5. A fusion protein comprising the CXCR3 ligand according to claim 1.

6. A pharmaceutical composition comprising the CXCR3 ligand according to claim 1.

7. A C-X-C Motif Chemokine Receptor 3 (CXCR3) ligand, wherein the CXCR3 ligand comprises a human C-X-C motif chemokine 10 (CXCL10) variant derived from human CXCL10 (SEQ ID NO: 60) a comprising substitution of the V-P-L-S-R-T-V-R sequence at the N-terminus of human CXCL10 with a sequence selected from the group consisting of:

(b1) V-X1-L-S-R-T-V-R, wherein X1 is F, G, I, K, L, M, T, V, W, or Y (SEQ ID NO: 205);

(b2) X2-V-P-L-S-R-T-V-R, wherein X2 is A, F, G, H, I, K, L, N, P, Q, R, S, T, V, W, or Y (SEQ ID NO: 206);

(b3) V-X3-P-L-S-R-T-V-R, wherein X3 is A, F, G, H, I, K, L, M, Q, R, S, T, V, W, or Y (SEQ ID NO: 207); and, (b4) P-L-S-R-T-V-R (SEQ ID NO: 208), or a human C-X-C motif chemokine 11 (CXCL1l) variant derived from human CXCL11 (SEQ ID NO: 61) or a human CXCL10-human CXCL11 chimeric protein (ITIP) variant a derived from ITIP (SEQ ID NO: 63), wherein the F-P-M-F-K-R-G-R sequence at the N-terminus of the human CXCL11 or human CXCL10-human CXCL11 chimeric protein (ITIP) is substituted with a sequence selected from the group consisting of:

(b5) X4-F-P-M-F-K-R-G-R, wherein X4 is A, D, E, F, G, H, I, K, L, M, N, P, Q, S, T, V, W, or Y (SEQ ID NO: 209);

(b6) F-X5-M-F-K-R-G-R, wherein X5 is A, D, E, G, H, I, M, N, Q, R, S, T, V, W, or Y (SEQ ID NO: 210); and (b7) F-X6-P-M-F-K-R-G-R, wherein X6 is A, D, E, F, G, H, L, M, N, P, Q, S, T, W, or Y (SEQ ID NO: 211).

8. The CXCR3 ligand according to claim 7, wherein the CXCL10 variant further comprises a substitution of arginine to alanine at amino acid position 75.

9. A fusion protein comprising the CXCR3 ligand according to claim 7.

10. A pharmaceutical composition comprising the CXCR3 ligand according to claim 7.

* * * * *

SEQUENCE LISTING

```
<160> NUMBER OF SEQ ID NOS: 388

<210> SEQ ID NO 1
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 1

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 2
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 2

Val Ala Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45
```

-continued

```
Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 3
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 3

Val Asp Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 4
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 4

Val Glu Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 5
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 5

Val Phe Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60
```

```
Leu Lys Ala Val Ser Lys Glu Arg Ser Lys Ala Ser Pro
65                  70                  75

<210> SEQ ID NO 6
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 6

Val Gly Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 7
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 7

Val His Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 8
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 8

Val Ile Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75
```

```
<210> SEQ ID NO 9
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 9

Val Lys Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 10
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 10

Val Leu Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 11
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 11

Val Met Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 12
<211> LENGTH: 77
<212> TYPE: PRT
<213> ORGANISM: Artificial sequence
```

<220> FEATURE:
<223> OTHER INFORMATION: an artificially synthesized sequence

<400> SEQUENCE: 12

Val Asn Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 13
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 13

Val Gln Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 14
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 14

Val Arg Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 15
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 15

-continued

```
Val Ser Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Ala Ser Pro
65                  70                  75
```

<210> SEQ ID NO 16
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 16

```
Val Thr Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Ala Ser Pro
65                  70                  75
```

<210> SEQ ID NO 17
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 17

```
Val Val Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Ala Ser Pro
65                  70                  75
```

<210> SEQ ID NO 18
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 18

```
Val Trp Leu Ser Arg Thr Val Arg Cys Thr Cys Ile Ser Ile Ser Asn
1               5                   10                  15
```

-continued

---

```
Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 19
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 19

Val Tyr Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 20
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 20

Ala Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 21
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 21

Asp Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
```

-continued

```
                35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 22
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 22

Glu Val Pro Leu Ser Arg Thr Val Arg Cys Thr Cys Ile Ser Ile Ser
1               5                  10                  15

Asn Gln Pro Val Asn Pro Arg Ser Leu Glu Lys Leu Glu Ile Ile Pro
                20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 23
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 23

Phe Val Pro Leu Ser Arg Thr Val Arg Cys Thr Cys Ile Ser Ile Ser
1               5                  10                  15

Asn Gln Pro Val Asn Pro Arg Ser Leu Glu Lys Leu Glu Ile Ile Pro
                20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 24
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 24

Gly Val Pro Leu Ser Arg Thr Val Arg Cys Thr Cys Ile Ser Ile Ser
1               5                  10                  15

Asn Gln Pro Val Asn Pro Arg Ser Leu Glu Lys Leu Glu Ile Ile Pro
                20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60
```

Leu Leu Lys Ala Val Ser Lys Glu Arg Ser Lys Ala Ser Pro
65                  70                  75

<210> SEQ ID NO 25
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 25

His Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 26
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 26

Ile Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 27
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 27

Lys Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

-continued

```
<210> SEQ ID NO 28
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 28

Leu Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 29
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 29

Met Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 30
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 30

Asn Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 31
<211> LENGTH: 78
<212> TYPE: PRT
```

<213> ORGANISM: Artificial sequence
<220> FEATURE:
<223> OTHER INFORMATION: an artificially synthesized sequence

<400> SEQUENCE: 31

```
Pro Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 32
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 32

```
Gln Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 33
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 33

```
Arg Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 34
<211> LENGTH: 78
<212> TYPE: PRT
<213> ORGANISM: Artificial sequence
<220> FEATURE:
<223> OTHER INFORMATION: an artificially synthesized sequence -continued

```
<400> SEQUENCE: 34

Ser Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 35
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 35

Thr Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 36
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 36

Val Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 37
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 37

Trp Val Pro Leu Ser Arg Thr Val Arg Cys Thr Cys Ile Ser Ile Ser
1               5                   10                  15
```

-continued

```
Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
            50                  55                  60

Leu Leu Lys Ala Val Ser Lys Glu Arg Ser Lys Ala Ser Pro
65                  70                  75

<210> SEQ ID NO 38
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 38

Tyr Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
            50                  55                  60

Leu Leu Lys Ala Val Ser Lys Glu Arg Ser Lys Ala Ser Pro
65                  70                  75

<210> SEQ ID NO 39
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 39

Val Ala Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
            50                  55                  60

Leu Leu Lys Ala Val Ser Lys Glu Arg Ser Lys Ala Ser Pro
65                  70                  75

<210> SEQ ID NO 40
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 40

Val Asp Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30
```

-continued

---

```
Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

```
<210> SEQ ID NO 41
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 41
```

```
Val Glu Pro Leu Ser Arg Thr Val Arg Cys Thr Cys Ile Ser Ile Ser
1               5                  10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

```
<210> SEQ ID NO 42
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 42
```

```
Val Phe Pro Leu Ser Arg Thr Val Arg Cys Thr Cys Ile Ser Ile Ser
1               5                  10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

```
<210> SEQ ID NO 43
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 43
```

```
Val Gly Pro Leu Ser Arg Thr Val Arg Cys Thr Cys Ile Ser Ile Ser
1               5                  10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
```

-continued

```
                50              55              60

Leu Leu Lys Ala Val Ser Lys Glu Arg Ser Lys Ala Ser Pro
65                  70              75

<210> SEQ ID NO 44
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 44

Val His Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
                20              25              30

Ala Ser Gln Phe Cys Pro Arg Val Glu Ile Ile Ala Thr Met Lys Lys
            35              40              45

Lys Gly Glu Lys Arg Cys Leu Asn Pro Glu Ser Lys Ala Ile Lys Asn
        50              55              60

Leu Leu Lys Ala Val Ser Lys Glu Arg Ser Lys Ala Ser Pro
65                  70              75

<210> SEQ ID NO 45
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 45

Val Ile Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
                20              25              30

Ala Ser Gln Phe Cys Pro Arg Val Glu Ile Ile Ala Thr Met Lys Lys
            35              40              45

Lys Gly Glu Lys Arg Cys Leu Asn Pro Glu Ser Lys Ala Ile Lys Asn
        50              55              60

Leu Leu Lys Ala Val Ser Lys Glu Arg Ser Lys Ala Ser Pro
65                  70              75

<210> SEQ ID NO 46
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 46

Val Lys Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
                20              25              30

Ala Ser Gln Phe Cys Pro Arg Val Glu Ile Ile Ala Thr Met Lys Lys
            35              40              45

Lys Gly Glu Lys Arg Cys Leu Asn Pro Glu Ser Lys Ala Ile Lys Asn
        50              55              60

Leu Leu Lys Ala Val Ser Lys Glu Arg Ser Lys Ala Ser Pro
65                  70              75
```

-continued

```
<210> SEQ ID NO 47
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 47

Val Leu Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 48
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 48

Val Met Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 49
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 49

Val Asn Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 50
<211> LENGTH: 78
```

```
<212> TYPE: PRT
<213> ORGANISM: Artificial sequence
<220> FEATURE:
<223> OTHER INFORMATION: an artificially synthesized sequence

<400> SEQUENCE: 50

Val Pro Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 51
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 51

Val Gln Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 52
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 52

Val Arg Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 53
<211> LENGTH: 78
<212> TYPE: PRT
<213> ORGANISM: Artificial sequence
<220> FEATURE:
<223> OTHER INFORMATION: an artificially synthesized sequence
```

-continued

<400> SEQUENCE: 53

```
Val Ser Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 54
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 54

```
Val Thr Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 55
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 55

```
Val Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 56
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 56

```
Val Trp Pro Leu Ser Arg Thr Val Arg Cys Thr Cys Ile Ser Ile Ser
```

-continued

```
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 57
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 57

Val Tyr Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 58
<211> LENGTH: 230
<212> TYPE: PRT
<213> ORGANISM: Artificial sequence
<220> FEATURE:
<223> OTHER INFORMATION: an artificially synthesized sequence

<400> SEQUENCE: 58

Glu Pro Lys Ser Ser Asp Lys Thr His Thr Cys Pro Pro Cys Pro Ala
1               5                   10                  15

Pro Glu Leu Arg Arg Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110

Leu Pro Ser Ser Ile Glu Lys Thr Ile Ser Lys Ala Lys Gly Gln Pro
        115                 120                 125

Arg Glu Pro Gln Val Cys Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160
```

-continued

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Glu Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro
225                 230

<210> SEQ ID NO 59
<211> LENGTH: 230
<212> TYPE: PRT
<213> ORGANISM: Artificial sequence
<220> FEATURE:
<223> OTHER INFORMATION: an artificially synthesized sequence

<400> SEQUENCE: 59

Glu Pro Lys Ser Ser Asp Lys Thr His Thr Cys Pro Pro Cys Pro Ala
1               5                   10                  15

Pro Glu Leu Arg Arg Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
                100                 105                 110

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Cys Glu Met Thr
        130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
                180                 185                 190

Ser Lys Leu Thr Val Asp Lys Ser Arg Trp Gln Glu Gly Asn Val Phe
            195                 200                 205

Ser Cys Ser Val Met His Glu Ala Leu His Asn Arg Tyr Thr Gln Lys
        210                 215                 220

Ser Leu Ser Leu Ser Pro
225                 230

<210> SEQ ID NO 60
<211> LENGTH: 77
<212> TYPE: PRT
<213> ORGANISM: Homo sapiens

<400> SEQUENCE: 60

Val Pro Leu Ser Arg Thr Val Arg Cys Thr Cys Ile Ser Ile Ser Asn
```

-continued

```
1              5               10              15

Gln Pro Val Asn Pro Arg Ser Leu Glu Lys Leu Glu Ile Ile Pro Ala
            20              25              30

Ser Gln Phe Cys Pro Arg Val Glu Ile Ile Ala Thr Met Lys Lys Lys
        35              40              45

Gly Glu Lys Arg Cys Leu Asn Pro Glu Ser Lys Ala Ile Lys Asn Leu
    50              55              60

Leu Lys Ala Val Ser Lys Glu Arg Ser Lys Arg Ser Pro
65              70              75

<210> SEQ ID NO 61
<211> LENGTH: 73
<212> TYPE: PRT
<213> ORGANISM: Homo sapiens

<400> SEQUENCE: 61

Phe Pro Met Phe Lys Arg Gly Arg Cys Leu Cys Ile Gly Pro Gly Val
1              5               10              15

Lys Ala Val Lys Val Ala Asp Ile Glu Lys Ala Ser Ile Met Tyr Pro
            20              25              30

Ser Asn Asn Cys Asp Lys Ile Glu Val Ile Ile Thr Leu Lys Glu Asn
        35              40              45

Lys Gly Gln Arg Cys Leu Asn Pro Lys Ser Lys Gln Ala Arg Leu Ile
    50              55              60

Ile Lys Lys Val Glu Arg Lys Asn Phe
65              70

<210> SEQ ID NO 62
<211> LENGTH: 103
<212> TYPE: PRT
<213> ORGANISM: Homo sapiens

<400> SEQUENCE: 62

Thr Pro Val Val Arg Lys Gly Arg Cys Ser Cys Ile Ser Thr Asn Gln
1              5               10              15

Gly Thr Ile His Leu Gln Ser Leu Lys Asp Leu Lys Gln Phe Ala Pro
            20              25              30

Ser Pro Ser Cys Glu Lys Ile Glu Ile Ile Ala Thr Leu Lys Asn Gly
        35              40              45

Val Gln Thr Cys Leu Asn Pro Asp Ser Ala Asp Val Lys Glu Leu Ile
    50              55              60

Lys Lys Trp Glu Lys Gln Val Ser Gln Lys Lys Lys Gln Lys Asn Gly
65              70              75              80

Lys Lys His Gln Lys Lys Lys Val Leu Lys Val Arg Lys Ser Gln Arg
            85              90              95

Ser Arg Gln Lys Lys Thr Thr
        100

<210> SEQ ID NO 63
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 63

Phe Pro Met Phe Lys Arg Gly Arg Cys Leu Cys Ile Gly Pro Gly Val
1              5               10              15
```

-continued

```
Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 64
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 64

Gly Gly Gly Ser
1

<210> SEQ ID NO 65
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 65

Gly Gly Ser Gly
1

<210> SEQ ID NO 66
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 66

Gly Ser Gly Gly
1

<210> SEQ ID NO 67
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 67

Ser Gly Gly Gly
1

<210> SEQ ID NO 68
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 68

Gly Ser Ser Gly
1

<210> SEQ ID NO 69
```

```
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 69

Gly Gly Gly Gly Ser
1               5

<210> SEQ ID NO 70
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 70

Gly Gly Gly Ser Gly
1               5

<210> SEQ ID NO 71
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 71

Gly Gly Ser Gly Gly
1               5

<210> SEQ ID NO 72
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 72

Gly Ser Gly Gly Gly
1               5

<210> SEQ ID NO 73
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 73

Gly Ser Gly Gly Ser
1               5

<210> SEQ ID NO 74
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 74

Ser Gly Gly Gly Gly
1               5

<210> SEQ ID NO 75
<211> LENGTH: 5
```

```
<212> TYPE: PRT
<213> ORGANISM: Artificial sequence
<220> FEATURE:
<223> OTHER INFORMATION: an artificially synthesized sequence

<400> SEQUENCE: 75

Gly Ser Ser Gly Gly
1               5

<210> SEQ ID NO 76
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 76

Gly Ser Gly Ser Gly
1               5

<210> SEQ ID NO 77
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 77

Ser Gly Gly Ser Gly
1               5

<210> SEQ ID NO 78
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 78

Gly Ser Ser Ser Gly
1               5

<210> SEQ ID NO 79
<211> LENGTH: 6
<212> TYPE: PRT
<213> ORGANISM: Artificial sequence
<220> FEATURE:
<223> OTHER INFORMATION: an artificially synthesized sequence

<400> SEQUENCE: 79

Gly Gly Gly Gly Gly Ser
1               5

<210> SEQ ID NO 80
<211> LENGTH: 6
<212> TYPE: PRT
<213> ORGANISM: Artificial sequence
<220> FEATURE:
<223> OTHER INFORMATION: an artificially synthesized sequence

<400> SEQUENCE: 80

Ser Gly Gly Gly Gly Gly
1               5

<210> SEQ ID NO 81
<211> LENGTH: 7
<212> TYPE: PRT
```

-continued

<213> ORGANISM: Artificial sequence
<220> FEATURE:
<223> OTHER INFORMATION: an artificially synthesized sequence

<400> SEQUENCE: 81

Gly Gly Gly Gly Gly Gly Ser
1               5

<210> SEQ ID NO 82
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 82

Ser Gly Gly Gly Gly Gly Gly
1               5

<210> SEQ ID NO 83
<211> LENGTH: 21
<212> TYPE: PRT
<213> ORGANISM: Artificial sequence
<220> FEATURE:
<223> OTHER INFORMATION: an artificially synthesized sequence

<400> SEQUENCE: 83

Met Asn Gln Thr Ala Ile Leu Ile Cys Cys Leu Ile Phe Leu Thr Leu
1               5                   10                  15

Ser Gly Ile Gln Gly
            20

<210> SEQ ID NO 84
<211> LENGTH: 22
<212> TYPE: PRT
<213> ORGANISM: Artificial sequence
<220> FEATURE:
<223> OTHER INFORMATION: an artificially synthesized sequence

<400> SEQUENCE: 84

Met Lys Lys Ser Gly Val Leu Phe Leu Leu Gly Ile Ile Leu Leu Val
1               5                   10                  15

Leu Ile Gly Val Gln Gly
            20

<210> SEQ ID NO 85
<211> LENGTH: 21
<212> TYPE: PRT
<213> ORGANISM: Artificial sequence
<220> FEATURE:
<223> OTHER INFORMATION: an artificially synthesized sequence

<400> SEQUENCE: 85

Met Ser Val Lys Gly Met Ala Ile Ala Leu Ala Val Ile Leu Cys Ala
1               5                   10                  15

Thr Val Val Gln Gly
            20

<210> SEQ ID NO 86
<211> LENGTH: 8
<212> TYPE: PRT
<213> ORGANISM: Artificial sequence
<220> FEATURE:
<223> OTHER INFORMATION: an artificially synthesized sequence

<400> SEQUENCE: 86

-continued

Val Pro Leu Ser Arg Thr Val Arg
1               5

<210> SEQ ID NO 87
<211> LENGTH: 8
<212> TYPE: PRT
<213> ORGANISM: Artificial sequence
<220> FEATURE:
<223> OTHER INFORMATION: an artificially synthesized sequence

<400> SEQUENCE: 87

Val Ala Leu Ser Arg Thr Val Arg
1               5

<210> SEQ ID NO 88
<211> LENGTH: 368
<212> TYPE: PRT
<213> ORGANISM: Homo sapiens

<400> SEQUENCE: 88

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
                100                 105                 110

Ala Ala Val Gln Trp Val Phe Gly Ser Gly Leu Cys Lys Val Ala Gly
            115                 120                 125

Ala Leu Phe Asn Ile Asn Phe Tyr Ala Gly Ala Leu Leu Leu Ala Cys
        130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
            195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

```
Asn Cys Gly Arg Glu Ser Arg Val Asp Val Ala Lys Ser Val Thr Ser
    290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
                340                 345                 350

Arg Asp Ser Ser Trp Ser Glu Thr Ser Glu Ala Ser Tyr Ser Gly Leu
            355                 360                 365
```

<210> SEQ ID NO 89
<211> LENGTH: 53
<212> TYPE: PRT
<213> ORGANISM: Artificial sequence
<220> FEATURE:
<223> OTHER INFORMATION: an artificially synthesized sequence

<400> SEQUENCE: 89

```
Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
                20                  25                  30

Glu Ser Asp Ser Cys Cys Thr Ser Pro Pro Cys Pro Gln Asp Phe Ser
            35                  40                  45

Leu Asn Phe Asp Arg
        50
```

<210> SEQ ID NO 90
<211> LENGTH: 21
<212> TYPE: PRT
<213> ORGANISM: Artificial sequence
<220> FEATURE:
<223> OTHER INFORMATION: an artificially synthesized sequence

<400> SEQUENCE: 90

```
Asn Phe Ser Ser Ser Tyr Asp Tyr Gly Glu Asn Glu Ser Asp Ser Cys
1               5                   10                  15

Cys Thr Ser Pro Pro
            20
```

<210> SEQ ID NO 91
<211> LENGTH: 8
<212> TYPE: PRT
<213> ORGANISM: Artificial sequence
<220> FEATURE:
<223> OTHER INFORMATION: an artificially synthesized sequence

<400> SEQUENCE: 91

```
Phe Pro Met Phe Lys Arg Gly Arg
1               5
```

<210> SEQ ID NO 92
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 92

```
Phe Ala Met Phe Lys Arg Gly Arg Cys Leu Cys Ile Gly Pro Gly Val
1               5                   10                  15
```

-continued

Lys Ala Val Lys Val Ala Asp Ile Glu Lys Ala Ser Ile Met Tyr Pro
        20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 93
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 93

Phe Asp Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
        20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 94
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 94

Phe Glu Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
        20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 95
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 95

Phe Phe Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
        20                  25                  30

Ser Asn Asn Cys Asp Lys Ile Glu Val Ile Ile Thr Leu Lys Glu Asn

-continued

```
            35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 96
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 96

Phe Gly Met Phe Lys Arg Gly Arg Cys Leu Cys Ile Gly Pro Gly Val
1               5                  10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 97
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 97

Phe His Met Phe Lys Arg Gly Arg Cys Leu Cys Ile Gly Pro Gly Val
1               5                  10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 98
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 98

Phe Ile Met Phe Lys Arg Gly Arg Cys Leu Cys Ile Gly Pro Gly Val
1               5                  10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
    50                  55                  60
```

```
Ile Lys Lys Val Glu Arg Lys Asn Phe
65                  70

<210> SEQ ID NO 99
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 99

Phe Lys Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 100
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 100

Phe Leu Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 101
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 101

Phe Met Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70
```

```
<210> SEQ ID NO 102
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 102

Phe Asn Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 103
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 103

Phe Gln Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 104
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 104

Phe Arg Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 105
<211> LENGTH: 73
<212> TYPE: PRT
```

-continued

<213> ORGANISM: Artificial sequence
<220> FEATURE:
<223> OTHER INFORMATION: an artificially synthesized sequence

<400> SEQUENCE: 105

```
Phe Ser Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70
```

<210> SEQ ID NO 106
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 106

```
Phe Thr Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70
```

<210> SEQ ID NO 107
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 107

```
Phe Val Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70
```

<210> SEQ ID NO 108
<211> LENGTH: 73
<212> TYPE: PRT
<213> ORGANISM: Artificial sequence
<220> FEATURE:
<223> OTHER INFORMATION: an artificially synthesized sequence -continued

<400> SEQUENCE: 108

Phe Trp Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 109
<211> LENGTH: 73
<212> TYPE: PRT
<213> ORGANISM: Artificial sequence
<220> FEATURE:
<223> OTHER INFORMATION: an artificially synthesized sequence

<400> SEQUENCE: 109

Phe Tyr Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 110
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 110

Ala Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 111
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 111

Asp Phe Pro Met Phe Lys Arg Gly Arg Cys Leu Cys Ile Gly Pro Gly
1               5                   10                  15

-continued

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 112
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 112

Glu Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 113
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 113

Phe Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 114
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 114

Gly Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

```
Pro Ser Asn Asn Cys Asp Lys Ile Glu Val Ile Ile Thr Leu Lys Glu
    35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

```
<210> SEQ ID NO 115
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 115

His Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
    35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

```
<210> SEQ ID NO 116
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 116

Ile Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
    35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

```
<210> SEQ ID NO 117
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 117

Lys Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
    35                  40                  45

Asn Lys Gly Gln Arg Cys Leu Asn Pro Lys Ser Lys Gln Ala Arg Leu
```

-continued

```
        50              55              60

Ile Ile Lys Lys Val Glu Arg Lys Asn Phe
65                  70

<210> SEQ ID NO 118
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 118

Leu Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 119
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 119

Met Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 120
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 120

Asn Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

```
<210> SEQ ID NO 121
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 121

Pro Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 122
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 122

Gln Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 123
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 123

Arg Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 124
<211> LENGTH: 74
```

```
<212> TYPE: PRT
<213> ORGANISM: Artificial sequence
<220> FEATURE:
<223> OTHER INFORMATION: an artificially synthesized sequence

<400> SEQUENCE: 124

Ser Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 125
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 125

Thr Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 126
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 126

Val Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 127
<211> LENGTH: 74
<212> TYPE: PRT
<213> ORGANISM: Artificial sequence
<220> FEATURE:
<223> OTHER INFORMATION: an artificially synthesized sequence
```

<400> SEQUENCE: 127

Trp Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 128
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 128

Tyr Phe Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 129
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 129

Phe Ala Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
                20                  25                  30

Pro Ser Asn Asn Cys Asp Lys Ile Glu Val Ile Ile Thr Leu Lys Glu
            35                  40                  45

Asn Lys Gly Gln Arg Cys Leu Asn Pro Lys Ser Lys Gln Ala Arg Leu
        50                  55                  60

Ile Ile Lys Lys Val Glu Arg Lys Asn Phe
65                  70

<210> SEQ ID NO 130
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 130

Phe Asp Pro Met Phe Lys Arg Gly Arg Cys Leu Cys Ile Gly Pro Gly

-continued

```
1                5                10               15

Val Lys Ala Val Lys Val Ala Asp Ile Glu Lys Ala Ser Ile Met Tyr
                20               25               30

Pro Ser Asn Asn Cys Asp Lys Ile Glu Val Ile Ile Thr Leu Lys Glu
        35               40               45

Asn Lys Gly Gln Arg Cys Leu Asn Pro Lys Ser Lys Gln Ala Arg Leu
    50               55               60

Ile Ile Lys Lys Val Glu Arg Lys Asn Phe
65               70
```

<210> SEQ ID NO 131
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 131

```
Phe Glu Pro Met Phe Lys Arg Gly Arg Cys Leu Cys Ile Gly Pro Gly
1                5                10               15

Val Lys Ala Val Lys Val Ala Asp Ile Glu Lys Ala Ser Ile Met Tyr
                20               25               30

Pro Ser Asn Asn Cys Asp Lys Ile Glu Val Ile Ile Thr Leu Lys Glu
        35               40               45

Asn Lys Gly Gln Arg Cys Leu Asn Pro Lys Ser Lys Gln Ala Arg Leu
    50               55               60

Ile Ile Lys Lys Val Glu Arg Lys Asn Phe
65               70
```

<210> SEQ ID NO 132
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 132

```
Phe Phe Pro Met Phe Lys Arg Gly Arg Cys Leu Cys Ile Gly Pro Gly
1                5                10               15

Val Lys Ala Val Lys Val Ala Asp Ile Glu Lys Ala Ser Ile Met Tyr
                20               25               30

Pro Ser Asn Asn Cys Asp Lys Ile Glu Val Ile Ile Thr Leu Lys Glu
        35               40               45

Asn Lys Gly Gln Arg Cys Leu Asn Pro Lys Ser Lys Gln Ala Arg Leu
    50               55               60

Ile Ile Lys Lys Val Glu Arg Lys Asn Phe
65               70
```

<210> SEQ ID NO 133
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 133

```
Phe Gly Pro Met Phe Lys Arg Gly Arg Cys Leu Cys Ile Gly Pro Gly
1                5                10               15

Val Lys Ala Val Lys Val Ala Asp Ile Glu Lys Ala Ser Ile Met Tyr
                20               25               30
```

```
Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 134
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 134

Phe His Pro Met Phe Lys Arg Gly Arg Cys Leu Cys Ile Gly Pro Gly
1               5                  10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 135
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 135

Phe Ile Pro Met Phe Lys Arg Gly Arg Cys Leu Cys Ile Gly Pro Gly
1               5                  10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 136
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 136

Phe Lys Pro Met Phe Lys Arg Gly Arg Cys Leu Cys Ile Gly Pro Gly
1               5                  10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45
```

-continued

```
Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

<210> SEQ ID NO 137
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 137

```
Phe Leu Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

<210> SEQ ID NO 138
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 138

```
Phe Met Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

<210> SEQ ID NO 139
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 139

```
Phe Asn Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
```

```
65                   70

<210> SEQ ID NO 140
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 140

Phe Pro Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 141
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 141

Phe Gln Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 142
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 142

Phe Arg Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 143
```

-continued

<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 143

Phe Ser Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 144
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 144

Phe Thr Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 145
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 145

Phe Val Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70

<210> SEQ ID NO 146
<211> LENGTH: 74
<212> TYPE: PRT
<213> ORGANISM: Artificial sequence
<220> FEATURE:

<223> OTHER INFORMATION: an artificially synthesized sequence

<400> SEQUENCE: 146

```
Phe Trp Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

<210> SEQ ID NO 147
<211> LENGTH: 74
<212> TYPE: PRT
<213> ORGANISM: Artificial sequence
<220> FEATURE:
<223> OTHER INFORMATION: an artificially synthesized sequence

<400> SEQUENCE: 147

```
Phe Tyr Pro Met Phe Lys Arg Gly Arg Cys Leu Cys Ile Gly Pro Gly
1               5                   10                  15

Val Lys Ala Val Lys Val Ala Asp Ile Glu Lys Ala Ser Ile Met Tyr
            20                  25                  30

Pro Ser Asn Asn Cys Asp Lys Ile Glu Val Ile Ile Thr Leu Lys Glu
        35                  40                  45

Asn Lys Gly Gln Arg Cys Leu Asn Pro Lys Ser Lys Gln Ala Arg Leu
    50                  55                  60

Ile Ile Lys Lys Val Glu Arg Lys Asn Phe
65                  70
```

<210> SEQ ID NO 148
<211> LENGTH: 19
<212> TYPE: PRT
<213> ORGANISM: Artificial sequence
<220> FEATURE:
<223> OTHER INFORMATION: an artificially synthesized sequence

<400> SEQUENCE: 148

```
Met Gly Trp Ser Cys Ile Ile Leu Phe Leu Val Ala Thr Ala Thr Gly
1               5                   10                  15

Val His Ser
```

<210> SEQ ID NO 149
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 149

```
Phe Ala Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
```

-continued

```
                50                  55                  60

Leu Lys Ala Val Ser Lys Glu Arg Ser Lys Ala Ser Pro
65                  70                  75

<210> SEQ ID NO 150
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 150

Phe Asp Met Phe Lys Arg Gly Arg Cys Leu Cys Ile Gly Pro Gly Val
1                   5                  10                  15

Lys Ala Val Lys Val Ala Asp Ile Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Ala Ser Pro
65                  70                  75

<210> SEQ ID NO 151
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 151

Phe Glu Met Phe Lys Arg Gly Arg Cys Leu Cys Ile Gly Pro Gly Val
1                   5                  10                  15

Lys Ala Val Lys Val Ala Asp Ile Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Ala Ser Pro
65                  70                  75

<210> SEQ ID NO 152
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 152

Phe Phe Met Phe Lys Arg Gly Arg Cys Leu Cys Ile Gly Pro Gly Val
1                   5                  10                  15

Lys Ala Val Lys Val Ala Asp Ile Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Ala Ser Pro
65                  70                  75
```

-continued

```
<210> SEQ ID NO 153
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 153

Phe Gly Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 154
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 154

Phe His Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 155
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 155

Phe Ile Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 156
<211> LENGTH: 77
```

<212> TYPE: PRT
<213> ORGANISM: Artificial sequence
<220> FEATURE:
<223> OTHER INFORMATION: an artificially synthesized sequence

<400> SEQUENCE: 156

Phe Lys Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 157
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 157

Phe Leu Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 158
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 158

Phe Met Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 159
<211> LENGTH: 77
<212> TYPE: PRT
<213> ORGANISM: Artificial sequence
<220> FEATURE:
<223> OTHER INFORMATION: an artificially synthesized sequence

```
<400> SEQUENCE: 159

Phe Asn Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 160
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 160

Phe Gln Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 161
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 161

Phe Arg Met Phe Lys Arg Gly Arg Cys Leu Cys Ile Gly Pro Gly Val
1               5                   10                  15

Lys Ala Val Lys Val Ala Asp Ile Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Ala Ser Pro
65                  70                  75

<210> SEQ ID NO 162
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 162

Phe Ser Met Phe Lys Arg Gly Arg Cys Leu Cys Ile Gly Pro Gly Val
```

-continued

```
1               5               10              15

Lys Ala Val Lys Val Ala Asp Ile Glu Lys Leu Glu Ile Ile Pro Ala
            20              25              30

Ser Gln Phe Cys Pro Arg Val Glu Ile Ile Ala Thr Met Lys Lys Lys
        35              40              45

Gly Glu Lys Arg Cys Leu Asn Pro Glu Ser Lys Ala Ile Lys Asn Leu
    50              55              60

Leu Lys Ala Val Ser Lys Glu Arg Ser Lys Ala Ser Pro
65              70              75
```

```
<210> SEQ ID NO 163
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 163

Phe Thr Met Phe Lys Arg Gly Arg Cys Leu Cys Ile Gly Pro Gly Val
1               5               10              15

Lys Ala Val Lys Val Ala Asp Ile Glu Lys Leu Glu Ile Ile Pro Ala
            20              25              30

Ser Gln Phe Cys Pro Arg Val Glu Ile Ile Ala Thr Met Lys Lys Lys
        35              40              45

Gly Glu Lys Arg Cys Leu Asn Pro Glu Ser Lys Ala Ile Lys Asn Leu
    50              55              60

Leu Lys Ala Val Ser Lys Glu Arg Ser Lys Ala Ser Pro
65              70              75
```

```
<210> SEQ ID NO 164
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 164

Phe Val Met Phe Lys Arg Gly Arg Cys Leu Cys Ile Gly Pro Gly Val
1               5               10              15

Lys Ala Val Lys Val Ala Asp Ile Glu Lys Leu Glu Ile Ile Pro Ala
            20              25              30

Ser Gln Phe Cys Pro Arg Val Glu Ile Ile Ala Thr Met Lys Lys Lys
        35              40              45

Gly Glu Lys Arg Cys Leu Asn Pro Glu Ser Lys Ala Ile Lys Asn Leu
    50              55              60

Leu Lys Ala Val Ser Lys Glu Arg Ser Lys Ala Ser Pro
65              70              75
```

```
<210> SEQ ID NO 165
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 165

Phe Trp Met Phe Lys Arg Gly Arg Cys Leu Cys Ile Gly Pro Gly Val
1               5               10              15

Lys Ala Val Lys Val Ala Asp Ile Glu Lys Leu Glu Ile Ile Pro Ala
            20              25              30
```

```
Ser Gln Phe Cys Pro Arg Val Glu Ile Ile Ala Thr Met Lys Lys Lys
        35              40              45

Gly Glu Lys Arg Cys Leu Asn Pro Glu Ser Lys Ala Ile Lys Asn Leu
    50              55              60

Leu Lys Ala Val Ser Lys Glu Arg Ser Lys Ala Ser Pro
65                  70              75

<210> SEQ ID NO 166
<211> LENGTH: 77
<212> TYPE: PRT
<213> ORGANISM: Artificial sequence
<220> FEATURE:
<223> OTHER INFORMATION: an artificially synthesized sequence

<400> SEQUENCE: 166

Phe Tyr Met Phe Lys Arg Gly Arg Cys Leu Cys Ile Gly Pro Gly Val
1               5               10              15

Lys Ala Val Lys Val Ala Asp Ile Glu Lys Leu Glu Ile Ile Pro Ala
        20              25              30

Ser Gln Phe Cys Pro Arg Val Glu Ile Ile Ala Thr Met Lys Lys Lys
        35              40              45

Gly Glu Lys Arg Cys Leu Asn Pro Glu Ser Lys Ala Ile Lys Asn Leu
    50              55              60

Leu Lys Ala Val Ser Lys Glu Arg Ser Lys Ala Ser Pro
65                  70              75

<210> SEQ ID NO 167
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 167

Ala Phe Pro Met Phe Lys Arg Gly Arg Cys Leu Cys Ile Gly Pro Gly
1               5               10              15

Val Lys Ala Val Lys Val Ala Asp Ile Glu Lys Leu Glu Ile Ile Pro
        20              25              30

Ala Ser Gln Phe Cys Pro Arg Val Glu Ile Ile Ala Thr Met Lys Lys
        35              40              45

Lys Gly Glu Lys Arg Cys Leu Asn Pro Glu Ser Lys Ala Ile Lys Asn
    50              55              60

Leu Leu Lys Ala Val Ser Lys Glu Arg Ser Lys Ala Ser Pro
65                  70              75

<210> SEQ ID NO 168
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 168

Asp Phe Pro Met Phe Lys Arg Gly Arg Cys Leu Cys Ile Gly Pro Gly
1               5               10              15

Val Lys Ala Val Lys Val Ala Asp Ile Glu Lys Leu Glu Ile Ile Pro
        20              25              30

Ala Ser Gln Phe Cys Pro Arg Val Glu Ile Ile Ala Thr Met Lys Lys
        35              40              45
```

-continued

```
Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 169
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 169

Glu Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 170
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 170

Phe Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 171
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 171

Gly Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
```

```
65              70              75

<210> SEQ ID NO 172
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 172

His Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 173
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 173

Ile Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 174
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 174

Lys Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 175
```

```
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 175

Leu Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 176
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 176

Met Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 177
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 177

Asn Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 178
<211> LENGTH: 78
<212> TYPE: PRT
<213> ORGANISM: Artificial sequence
<220> FEATURE:
```

-continued

<223> OTHER INFORMATION: an artificially synthesized sequence

<400> SEQUENCE: 178

```
Pro Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
        50                  55                  60

Leu Leu Lys Ala Val Ser Lys Glu Arg Ser Lys Ala Ser Pro
65                  70                  75
```

<210> SEQ ID NO 179
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 179

```
Gln Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
        50                  55                  60

Leu Leu Lys Ala Val Ser Lys Glu Arg Ser Lys Ala Ser Pro
65                  70                  75
```

<210> SEQ ID NO 180
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 180

```
Arg Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
        50                  55                  60

Leu Leu Lys Ala Val Ser Lys Glu Arg Ser Lys Ala Ser Pro
65                  70                  75
```

<210> SEQ ID NO 181
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 181

-continued

```
Ser Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 182
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 182

Thr Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 183
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 183

Val Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 184
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 184

Trp Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
```

-continued

```
               20              25              30

Ala Ser Gln Phe Cys Pro Arg Val Glu Ile Ile Ala Thr Met Lys Lys
        35              40              45

Lys Gly Glu Lys Arg Cys Leu Asn Pro Glu Ser Lys Ala Ile Lys Asn
    50              55              60

Leu Leu Lys Ala Val Ser Lys Glu Arg Ser Lys Ala Ser Pro
65              70              75

<210> SEQ ID NO 185
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 185

Tyr Phe Pro Met Phe Lys Arg Gly Arg Cys Leu Cys Ile Gly Pro Gly
1               5              10              15

Val Lys Ala Val Lys Val Ala Asp Ile Glu Lys Leu Glu Ile Ile Pro
        20              25              30

Ala Ser Gln Phe Cys Pro Arg Val Glu Ile Ile Ala Thr Met Lys Lys
        35              40              45

Lys Gly Glu Lys Arg Cys Leu Asn Pro Glu Ser Lys Ala Ile Lys Asn
    50              55              60

Leu Leu Lys Ala Val Ser Lys Glu Arg Ser Lys Ala Ser Pro
65              70              75

<210> SEQ ID NO 186
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 186

Phe Ala Pro Met Phe Lys Arg Gly Arg Cys Leu Cys Ile Gly Pro Gly
1               5              10              15

Val Lys Ala Val Lys Val Ala Asp Ile Glu Lys Leu Glu Ile Ile Pro
        20              25              30

Ala Ser Gln Phe Cys Pro Arg Val Glu Ile Ile Ala Thr Met Lys Lys
        35              40              45

Lys Gly Glu Lys Arg Cys Leu Asn Pro Glu Ser Lys Ala Ile Lys Asn
    50              55              60

Leu Leu Lys Ala Val Ser Lys Glu Arg Ser Lys Ala Ser Pro
65              70              75

<210> SEQ ID NO 187
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 187

Phe Asp Pro Met Phe Lys Arg Gly Arg Cys Leu Cys Ile Gly Pro Gly
1               5              10              15

Val Lys Ala Val Lys Val Ala Asp Ile Glu Lys Leu Glu Ile Ile Pro
        20              25              30

Ala Ser Gln Phe Cys Pro Arg Val Glu Ile Ile Ala Thr Met Lys Lys
        35              40              45
```

-continued

```
Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 188
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 188

Phe Glu Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 189
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 189

Phe Phe Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 190
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 190

Phe Gly Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
    50                  55                  60
```

```
Leu Leu Lys Ala Val Ser Lys Glu Arg Ser Lys Ala Ser Pro
65                  70                  75

<210> SEQ ID NO 191
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 191

Phe His Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
        50                  55                  60

Leu Leu Lys Ala Val Ser Lys Glu Arg Ser Lys Ala Ser Pro
65                  70                  75

<210> SEQ ID NO 192
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 192

Phe Ile Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
        50                  55                  60

Leu Leu Lys Ala Val Ser Lys Glu Arg Ser Lys Ala Ser Pro
65                  70                  75

<210> SEQ ID NO 193
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 193

Phe Lys Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
                20                  25                  30

Ala Ser Gln Phe Cys Pro Arg Val Glu Ile Ile Ala Thr Met Lys Lys
            35                  40                  45

Lys Gly Glu Lys Arg Cys Leu Asn Pro Glu Ser Lys Ala Ile Lys Asn
        50                  55                  60

Leu Leu Lys Ala Val Ser Lys Glu Arg Ser Lys Ala Ser Pro
65                  70                  75
```

```
<210> SEQ ID NO 194
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 194

Phe Leu Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 195
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 195

Phe Met Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 196
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 196

Phe Asn Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 197
<211> LENGTH: 78
<212> TYPE: PRT
<213> ORGANISM: Artificial sequence
```

```
<220> FEATURE:
<223> OTHER INFORMATION: an artificially synthesized sequence

<400> SEQUENCE: 197

Phe Pro Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 198
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 198

Phe Gln Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 199
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 199

Phe Arg Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75

<210> SEQ ID NO 200
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 200
```

-continued

```
Phe Ser Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

```
<210> SEQ ID NO 201
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 201
```

```
Phe Thr Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

```
<210> SEQ ID NO 202
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 202
```

```
Phe Val Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

```
<210> SEQ ID NO 203
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 203
```

```
Phe Trp Pro Met Phe Lys Arg Gly Arg Cys Leu Cys Ile Gly Pro Gly
1               5                   10                  15
```

-continued

```
Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 204
<211> LENGTH: 78
<212> TYPE: PRT
<213> ORGANISM: Artificial sequence
<220> FEATURE:
<223> OTHER INFORMATION: an artificially synthesized sequence

<400> SEQUENCE: 204

```
Phe Tyr Pro Met Phe Lys Arg Gly Arg Cys Leu Cys Ile Gly Pro Gly
1               5                   10                  15

Val Lys Ala Val Lys Val Ala Asp Ile Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Ala Ser Pro
65                  70                  75
```

<210> SEQ ID NO 205
<211> LENGTH: 8
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (2)..(2)
<223> OTHER INFORMATION: Xaa is F, G, I, K, L, M, T, V, W, or Y

<400> SEQUENCE: 205

```
Val Xaa Leu Ser Arg Thr Val Arg
1               5
```

<210> SEQ ID NO 206
<211> LENGTH: 9
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (1)..(1)
<223> OTHER INFORMATION: Xaa is A, F, G, H, I, K, L, M, N, P, Q, R, S,
      T, V, W, or Y

<400> SEQUENCE: 206

```
Xaa Val Pro Leu Ser Arg Thr Val Arg
1               5
```

<210> SEQ ID NO 207
<211> LENGTH: 9
<212> TYPE: PRT
<213> ORGANISM: Artificial sequence
<220> FEATURE:
<223> OTHER INFORMATION: an artificially synthesized sequence

```
<220> FEATURE:
<221> NAME/KEY: SITE
<222> LOCATION: (2)..(2)
<223> OTHER INFORMATION: Xaa is A, F, G, H, I, K, L, M, P, Q, R, S, T,
      V, W, or Y

<400> SEQUENCE: 207

Val Xaa Pro Leu Ser Arg Thr Val Arg
1               5

<210> SEQ ID NO 208
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 208

Pro Leu Ser Arg Thr Val Arg
1               5

<210> SEQ ID NO 209
<211> LENGTH: 9
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (1)..(1)
<223> OTHER INFORMATION: Xaa is A, D, E, F, G, H, I, K, L, M, N, P, Q,
      S, T, V, W, or Y

<400> SEQUENCE: 209

Xaa Phe Pro Met Phe Lys Arg Gly Arg
1               5

<210> SEQ ID NO 210
<211> LENGTH: 8
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (2)..(2)
<223> OTHER INFORMATION: Xaa is A, D, E, G, H, I, M, N, Q, R, S, T, V,
      W, or Y

<400> SEQUENCE: 210

Phe Xaa Met Phe Lys Arg Gly Arg
1               5

<210> SEQ ID NO 211
<211> LENGTH: 9
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (2)..(2)
<223> OTHER INFORMATION: Xaa is A, D, E, F, G, H, L, M, N, P, Q, S, T,
      W, or Y

<400> SEQUENCE: 211

Phe Xaa Pro Met Phe Lys Arg Gly Arg
1               5
```

```
<210> SEQ ID NO 212
<211> LENGTH: 8
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (2)..(2)
<223> OTHER INFORMATION: Xaa is F, G, I, L, M, T, V, W, or Y

<400> SEQUENCE: 212

Val Xaa Leu Ser Arg Thr Val Arg
1               5

<210> SEQ ID NO 213
<211> LENGTH: 9
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (1)..(1)
<223> OTHER INFORMATION: Xaa is A, G, I, L, N, Q, S, T, or W

<400> SEQUENCE: 213

Xaa Val Pro Leu Ser Arg Thr Val Arg
1               5

<210> SEQ ID NO 214
<211> LENGTH: 9
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (2)..(2)
<223> OTHER INFORMATION: Xaa is A, F, G, I, M, P, T, or V

<400> SEQUENCE: 214

Val Xaa Pro Leu Ser Arg Thr Val Arg
1               5

<210> SEQ ID NO 215
<211> LENGTH: 9
<212> TYPE: PRT
<213> ORGANISM: Artificial sequence
<220> FEATURE:
<223> OTHER INFORMATION: an artificially synthesized sequence
<220> FEATURE:
<221> NAME/KEY: SITE
<222> LOCATION: (1)..(1)
<223> OTHER INFORMATION: Xaa is A, D, E, G, M, N, Q, S, T, V, or Y

<400> SEQUENCE: 215

Xaa Phe Pro Met Phe Lys Arg Gly Arg
1               5

<210> SEQ ID NO 216
<211> LENGTH: 18
<212> TYPE: PRT
<213> ORGANISM: Artificial sequence
<220> FEATURE:
<223> OTHER INFORMATION: an artificially synthesized sequence

<400> SEQUENCE: 216

Phe Leu Thr Leu Ser Gly Ile Gln Gly Val Pro Leu Ser Arg Thr Val
1               5                   10                  15
```

-continued

Arg Cys

<210> SEQ ID NO 217
<211> LENGTH: 18
<212> TYPE: PRT
<213> ORGANISM: Artificial sequence
<220> FEATURE:
<223> OTHER INFORMATION: an artificially synthesized sequence

<400> SEQUENCE: 217

Val Ala Thr Ala Thr Gly Val His Ser Phe Pro Met Phe Lys Arg Gly
1               5                   10                  15

Arg Cys

<210> SEQ ID NO 218
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 218

Val Pro Leu Ser
1

<210> SEQ ID NO 219
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 219

Val Ala Leu Ser
1

<210> SEQ ID NO 220
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 220

Val Asp Leu Ser
1

<210> SEQ ID NO 221
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 221

Val Glu Leu Ser
1

<210> SEQ ID NO 222
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 222

-continued

Val Phe Leu Ser
1

<210> SEQ ID NO 223
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 223

Val Gly Leu Ser
1

<210> SEQ ID NO 224
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 224

Val His Leu Ser
1

<210> SEQ ID NO 225
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 225

Val Ile Leu Ser
1

<210> SEQ ID NO 226
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 226

Val Lys Leu Ser
1

<210> SEQ ID NO 227
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 227

Val Leu Leu Ser
1

<210> SEQ ID NO 228
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 228

-continued

```
Val Met Leu Ser
1

<210> SEQ ID NO 229
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 229

Val Asn Leu Ser
1

<210> SEQ ID NO 230
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 230

Val Gln Leu Ser
1

<210> SEQ ID NO 231
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 231

Val Arg Leu Ser
1

<210> SEQ ID NO 232
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 232

Val Ser Leu Ser
1

<210> SEQ ID NO 233
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 233

Val Thr Leu Ser
1

<210> SEQ ID NO 234
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 234

Val Val Leu Ser
```

-continued

1

```
<210> SEQ ID NO 235
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 235

Val Trp Leu Ser
1

<210> SEQ ID NO 236
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 236

Val Tyr Leu Ser
1

<210> SEQ ID NO 237
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 237

Ala Val Pro Leu
1

<210> SEQ ID NO 238
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 238

Asp Val Pro Leu
1

<210> SEQ ID NO 239
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 239

Glu Val Pro Leu
1

<210> SEQ ID NO 240
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 240

Phe Val Pro Leu
1
```

```
<210> SEQ ID NO 241
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 241

Gly Val Pro Leu
1

<210> SEQ ID NO 242
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 242

His Val Pro Leu
1

<210> SEQ ID NO 243
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 243

Ile Val Pro Leu
1

<210> SEQ ID NO 244
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 244

Lys Val Pro Leu
1

<210> SEQ ID NO 245
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 245

Leu Val Pro Leu
1

<210> SEQ ID NO 246
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 246

Met Val Pro Leu
1
```

```
<210> SEQ ID NO 247
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 247

Asn Val Pro Leu
1

<210> SEQ ID NO 248
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 248

Pro Val Pro Leu
1

<210> SEQ ID NO 249
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 249

Gln Val Pro Leu
1

<210> SEQ ID NO 250
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 250

Arg Val Pro Leu
1

<210> SEQ ID NO 251
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 251

Ser Val Pro Leu
1

<210> SEQ ID NO 252
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 252

Thr Val Pro Leu
1
```

-continued

```
<210> SEQ ID NO 253
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 253

Val Val Pro Leu
1

<210> SEQ ID NO 254
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 254

Trp Val Pro Leu
1

<210> SEQ ID NO 255
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 255

Tyr Val Pro Leu
1

<210> SEQ ID NO 256
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 256

Val Ala Pro Leu
1

<210> SEQ ID NO 257
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 257

Val Asp Pro Leu
1

<210> SEQ ID NO 258
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 258

Val Glu Pro Leu
1

<210> SEQ ID NO 259
```

```
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 259

Val Phe Pro Leu
1

<210> SEQ ID NO 260
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 260

Val Gly Pro Leu
1

<210> SEQ ID NO 261
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 261

Val His Pro Leu
1

<210> SEQ ID NO 262
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 262

Val Ile Pro Leu
1

<210> SEQ ID NO 263
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 263

Val Lys Pro Leu
1

<210> SEQ ID NO 264
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 264

Val Leu Pro Leu
1

<210> SEQ ID NO 265
<211> LENGTH: 4
```

```
<212> TYPE: PRT
<213> ORGANISM: Artificial sequence
<220> FEATURE:
<223> OTHER INFORMATION: an artificially synthesized sequence

<400> SEQUENCE: 265

Val Met Pro Leu
1

<210> SEQ ID NO 266
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 266

Val Asn Pro Leu
1

<210> SEQ ID NO 267
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 267

Val Pro Pro Leu
1

<210> SEQ ID NO 268
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 268

Val Gln Pro Leu
1

<210> SEQ ID NO 269
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 269

Val Arg Pro Leu
1

<210> SEQ ID NO 270
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 270

Val Ser Pro Leu
1

<210> SEQ ID NO 271
<211> LENGTH: 4
<212> TYPE: PRT
```

```
<213> ORGANISM: Artificial sequence
<220> FEATURE:
<223> OTHER INFORMATION: an artificially synthesized sequence

<400> SEQUENCE: 271

Val Thr Pro Leu
1

<210> SEQ ID NO 272
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 272

Val Val Pro Leu
1

<210> SEQ ID NO 273
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 273

Val Trp Pro Leu
1

<210> SEQ ID NO 274
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 274

Val Tyr Pro Leu
1

<210> SEQ ID NO 275
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 275

Phe Pro Met Phe
1

<210> SEQ ID NO 276
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 276

Phe Ala Met Phe
1

<210> SEQ ID NO 277
<211> LENGTH: 4
<212> TYPE: PRT
<213> ORGANISM: Artificial sequence
```

-continued

```
<220> FEATURE:
<223> OTHER INFORMATION: an artificially synthesized sequence

<400> SEQUENCE: 277

Phe Asp Met Phe
1

<210> SEQ ID NO 278
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 278

Phe Glu Met Phe
1

<210> SEQ ID NO 279
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 279

Phe Phe Met Phe
1

<210> SEQ ID NO 280
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 280

Phe Gly Met Phe
1

<210> SEQ ID NO 281
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 281

Phe His Met Phe
1

<210> SEQ ID NO 282
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 282

Phe Ile Met Phe
1

<210> SEQ ID NO 283
<211> LENGTH: 4
<212> TYPE: PRT
<213> ORGANISM: Artificial sequence
<220> FEATURE:
```

<223> OTHER INFORMATION: an artificially synthesized sequence

<400> SEQUENCE: 283

Phe Lys Met Phe
1

<210> SEQ ID NO 284
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 284

Phe Leu Met Phe
1

<210> SEQ ID NO 285
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 285

Phe Met Met Phe
1

<210> SEQ ID NO 286
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 286

Phe Asn Met Phe
1

<210> SEQ ID NO 287
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 287

Phe Gln Met Phe
1

<210> SEQ ID NO 288
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 288

Phe Arg Met Phe
1

<210> SEQ ID NO 289
<211> LENGTH: 4
<212> TYPE: PRT
<213> ORGANISM: Artificial sequence
<220> FEATURE:
<223> OTHER INFORMATION: an artificially synthesized sequence -continued

```
<400> SEQUENCE: 289

Phe Ser Met Phe
1

<210> SEQ ID NO 290
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 290

Phe Thr Met Phe
1

<210> SEQ ID NO 291
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 291

Phe Val Met Phe
1

<210> SEQ ID NO 292
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 292

Phe Trp Met Phe
1

<210> SEQ ID NO 293
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 293

Phe Tyr Met Phe
1

<210> SEQ ID NO 294
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 294

Ala Phe Pro Met
1

<210> SEQ ID NO 295
<211> LENGTH: 4
<212> TYPE: PRT
<213> ORGANISM: Artificial sequence
<220> FEATURE:
<223> OTHER INFORMATION: an artificially synthesized sequence
```

-continued

```
<400> SEQUENCE: 295

Asp Phe Pro Met
1

<210> SEQ ID NO 296
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 296

Glu Phe Pro Met
1

<210> SEQ ID NO 297
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 297

Phe Phe Pro Met
1

<210> SEQ ID NO 298
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 298

Gly Phe Pro Met
1

<210> SEQ ID NO 299
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 299

His Phe Pro Met
1

<210> SEQ ID NO 300
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 300

Ile Phe Pro Met
1

<210> SEQ ID NO 301
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 301
```

```
Lys Phe Pro Met
1

<210> SEQ ID NO 302
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 302

Leu Phe Pro Met
1

<210> SEQ ID NO 303
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 303

Met Phe Pro Met
1

<210> SEQ ID NO 304
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 304

Asn Phe Pro Met
1

<210> SEQ ID NO 305
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 305

Pro Phe Pro Met
1

<210> SEQ ID NO 306
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 306

Gln Phe Pro Met
1

<210> SEQ ID NO 307
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 307
```

-continued

Arg Phe Pro Met
1

<210> SEQ ID NO 308
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 308

Ser Phe Pro Met
1

<210> SEQ ID NO 309
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 309

Thr Phe Pro Met
1

<210> SEQ ID NO 310
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 310

Val Phe Pro Met
1

<210> SEQ ID NO 311
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 311

Trp Phe Pro Met
1

<210> SEQ ID NO 312
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 312

Tyr Phe Pro Met
1

<210> SEQ ID NO 313
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 313

Phe Ala Pro Met

```
1

<210> SEQ ID NO 314
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 314

Phe Asp Pro Met
1

<210> SEQ ID NO 315
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 315

Phe Glu Pro Met
1

<210> SEQ ID NO 316
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 316

Phe Phe Pro Met
1

<210> SEQ ID NO 317
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 317

Phe Gly Pro Met
1

<210> SEQ ID NO 318
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 318

Phe His Pro Met
1

<210> SEQ ID NO 319
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 319

Phe Ile Pro Met
1
```

-continued

```
<210> SEQ ID NO 320
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 320

Phe Lys Pro Met
1

<210> SEQ ID NO 321
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 321

Phe Leu Pro Met
1

<210> SEQ ID NO 322
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 322

Phe Met Pro Met
1

<210> SEQ ID NO 323
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 323

Phe Asn Pro Met
1

<210> SEQ ID NO 324
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 324

Phe Pro Pro Met
1

<210> SEQ ID NO 325
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 325

Phe Gln Pro Met
1
```

```
<210> SEQ ID NO 326
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 326

Phe Arg Pro Met
1

<210> SEQ ID NO 327
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 327

Phe Ser Pro Met
1

<210> SEQ ID NO 328
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 328

Phe Thr Pro Met
1

<210> SEQ ID NO 329
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 329

Phe Val Pro Met
1

<210> SEQ ID NO 330
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 330

Phe Trp Pro Met
1

<210> SEQ ID NO 331
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 331

Phe Tyr Pro Met
1
```

```
<210> SEQ ID NO 332
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 332

Phe Pro Met Phe
1

<210> SEQ ID NO 333
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 333

Phe Ala Met Phe
1

<210> SEQ ID NO 334
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 334

Phe Asp Met Phe
1

<210> SEQ ID NO 335
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 335

Phe Glu Met Phe
1

<210> SEQ ID NO 336
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 336

Phe Phe Met Phe
1

<210> SEQ ID NO 337
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 337

Phe Gly Met Phe
1

<210> SEQ ID NO 338
```

-continued

```
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 338

Phe His Met Phe
1

<210> SEQ ID NO 339
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 339

Phe Ile Met Phe
1

<210> SEQ ID NO 340
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 340

Phe Lys Met Phe
1

<210> SEQ ID NO 341
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 341

Phe Leu Met Phe
1

<210> SEQ ID NO 342
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 342

Phe Met Met Phe
1

<210> SEQ ID NO 343
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 343

Phe Asn Met Phe
1

<210> SEQ ID NO 344
<211> LENGTH: 4
```

```
<212> TYPE: PRT
<213> ORGANISM: Artificial sequence
<220> FEATURE:
<223> OTHER INFORMATION: an artificially synthesized sequence

<400> SEQUENCE: 344

Phe Gln Met Phe
1

<210> SEQ ID NO 345
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 345

Phe Arg Met Phe
1

<210> SEQ ID NO 346
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 346

Phe Ser Met Phe
1

<210> SEQ ID NO 347
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 347

Phe Thr Met Phe
1

<210> SEQ ID NO 348
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 348

Phe Val Met Phe
1

<210> SEQ ID NO 349
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 349

Phe Trp Met Phe
1

<210> SEQ ID NO 350
<211> LENGTH: 4
<212> TYPE: PRT
```

-continued

```
<213> ORGANISM: Artificial sequence
<220> FEATURE:
<223> OTHER INFORMATION: an artificially synthesized sequence

<400> SEQUENCE: 350

Phe Tyr Met Phe
1

<210> SEQ ID NO 351
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 351

Ala Phe Pro Met
1

<210> SEQ ID NO 352
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 352

Asp Phe Pro Met
1

<210> SEQ ID NO 353
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 353

Glu Phe Pro Met
1

<210> SEQ ID NO 354
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 354

Phe Phe Pro Met
1

<210> SEQ ID NO 355
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 355

Gly Phe Pro Met
1

<210> SEQ ID NO 356
<211> LENGTH: 4
<212> TYPE: PRT
<213> ORGANISM: Artificial sequence
```

-continued

```
<220> FEATURE:
<223> OTHER INFORMATION: an artificially synthesized sequence

<400> SEQUENCE: 356

His Phe Pro Met
1

<210> SEQ ID NO 357
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 357

Ile Phe Pro Met
1

<210> SEQ ID NO 358
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 358

Lys Phe Pro Met
1

<210> SEQ ID NO 359
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 359

Leu Phe Pro Met
1

<210> SEQ ID NO 360
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 360

Met Phe Pro Met
1

<210> SEQ ID NO 361
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 361

Asn Phe Pro Met
1

<210> SEQ ID NO 362
<211> LENGTH: 4
<212> TYPE: PRT
<213> ORGANISM: Artificial sequence
<220> FEATURE:
```

-continued

```
<223> OTHER INFORMATION: an artificially synthesized sequence

<400> SEQUENCE: 362

Pro Phe Pro Met
1

<210> SEQ ID NO 363
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 363

Gln Phe Pro Met
1

<210> SEQ ID NO 364
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 364

Arg Phe Pro Met
1

<210> SEQ ID NO 365
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 365

Ser Phe Pro Met
1

<210> SEQ ID NO 366
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 366

Thr Phe Pro Met
1

<210> SEQ ID NO 367
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 367

Val Phe Pro Met
1

<210> SEQ ID NO 368
<211> LENGTH: 4
<212> TYPE: PRT
<213> ORGANISM: Artificial sequence
<220> FEATURE:
<223> OTHER INFORMATION: an artificially synthesized sequence
```

```
<400> SEQUENCE: 368

Trp Phe Pro Met
1

<210> SEQ ID NO 369
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 369

Tyr Phe Pro Met
1

<210> SEQ ID NO 370
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 370

Phe Ala Pro Met
1

<210> SEQ ID NO 371
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 371

Phe Asp Pro Met
1

<210> SEQ ID NO 372
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 372

Phe Glu Pro Met
1

<210> SEQ ID NO 373
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 373

Phe Phe Pro Met
1

<210> SEQ ID NO 374
<211> LENGTH: 4
<212> TYPE: PRT
<213> ORGANISM: Artificial sequence
<220> FEATURE:
<223> OTHER INFORMATION: an artificially synthesized sequence
```

-continued

```
<400> SEQUENCE: 374

Phe Gly Pro Met
1

<210> SEQ ID NO 375
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 375

Phe His Pro Met
1

<210> SEQ ID NO 376
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 376

Phe Ile Pro Met
1

<210> SEQ ID NO 377
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 377

Phe Lys Pro Met
1

<210> SEQ ID NO 378
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 378

Phe Leu Pro Met
1

<210> SEQ ID NO 379
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 379

Phe Met Pro Met
1

<210> SEQ ID NO 380
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 380
```

-continued

Phe Asn Pro Met
1

<210> SEQ ID NO 381
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 381

Phe Pro Pro Met
1

<210> SEQ ID NO 382
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 382

Phe Gln Pro Met
1

<210> SEQ ID NO 383
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 383

Phe Arg Pro Met
1

<210> SEQ ID NO 384
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 384

Phe Ser Pro Met
1

<210> SEQ ID NO 385
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 385

Phe Thr Pro Met
1

<210> SEQ ID NO 386
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 386

```
Phe Val Pro Met
1

<210> SEQ ID NO 387
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 387

Phe Trp Pro Met
1

<210> SEQ ID NO 388
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 388

Phe Tyr Pro Met
1
```